(12) United States Patent
Esfandyarpour et al.

(10) Patent No.: US 9,399,217 B2
(45) Date of Patent: *Jul. 26, 2016

(54) CHAMBER FREE NANOREACTOR SYSTEM

(75) Inventors: Hesaam Esfandyarpour, Redwood City, CA (US); Kosar B. Parizi, Redwood City, CA (US); Mark F. Oldham, Emerald Hills, CA (US)

(73) Assignee: GENAPSYS, INC., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/481,858

(22) Filed: May 27, 2012

(65) Prior Publication Data
US 2013/0034880 A1 Feb. 7, 2013
US 2016/0108469 A9 Apr. 21, 2016

Related U.S. Application Data

(63) Continuation-in-part of application No. PCT/US2011/054769, filed on Oct. 4, 2011.

(60) Provisional application No. 61/389,490, filed on Oct. 4, 2010, provisional application No. 61/389,484, filed on Oct. 4, 2010, provisional application No. 61/443,167, filed on Feb. 15, 2011, provisional application No. 61/491,081, filed on May 27, 2011.

(51) Int. Cl.
| | | |
|---|---|---|
| C12Q 1/68 | (2006.01) | |
| B01L 3/00 | (2006.01) | |
| B03C 1/28 | (2006.01) | |
| B03C 5/00 | (2006.01) | |
| B03C 5/02 | (2006.01) | |
| B01L 7/00 | (2006.01) | |

(52) U.S. Cl.
CPC ............ *B01L 3/502761* (2013.01); *B03C 1/288* (2013.01); *B03C 5/005* (2013.01); *B03C 5/026* (2013.01); *B01L 7/52* (2013.01); *B01L 2200/0668* (2013.01); *B01L 2300/089* (2013.01); *B01L 2300/0816* (2013.01); *B01L 2400/043* (2013.01); *B01L 2400/0415* (2013.01); *B01L 2400/0418* (2013.01); *B01L 2400/0421* (2013.01); *B01L 2400/0427* (2013.01); *B01L 2400/0655* (2013.01); *B03C 2201/26* (2013.01)

(58) Field of Classification Search
CPC . C12Q 1/686; C12Q 2565/607; C12Q 1/6869
USPC .......................... 435/6.12, 91.2; 204/557, 660
See application file for complete search history.

(56) References Cited

U.S. PATENT DOCUMENTS

| | | |
|---|---|---|
| 2,014,761 A | 9/1935 | Faust |
| 5,602,042 A | 2/1997 | Farber |
| 5,612,181 A | 3/1997 | Fourmentin-Guilbert |
| 5,795,782 A | 8/1998 | Church et al. |
| 5,834,197 A | 11/1998 | Parton |
| 6,046,097 A | 4/2000 | Hsieh et al. |
| 6,087,095 A | 7/2000 | Rosenthal et al. |
| 6,210,891 B1 | 4/2001 | Nyren et al. |
| 6,327,410 B1 | 12/2001 | Walt et al. |
| 6,632,655 B1 | 10/2003 | Mehta et al. |
| 6,833,246 B2 | 12/2004 | Balasubramanian |
| 6,953,958 B2 | 10/2005 | Baxter et al. |
| 7,081,192 B1 | 7/2006 | Wang et al. |
| 7,223,540 B2 | 5/2007 | Pourmand et al. |
| 7,242,241 B2 | 7/2007 | Toumazou et al. |
| 7,270,981 B2 | 9/2007 | Armes et al. |
| 7,282,370 B2 | 10/2007 | Bridgham et al. |
| 7,291,496 B2 | 11/2007 | Holm-Kennedy |
| 7,312,085 B2 | 12/2007 | Chou et al. |
| 7,317,216 B2 | 1/2008 | Holm-Kennedy |
| 7,323,305 B2 | 1/2008 | Leamon et al. |
| 7,361,466 B2 | 4/2008 | Korlach et al. |

(Continued)

FOREIGN PATENT DOCUMENTS

| | | |
|---|---|---|
| CN | 1337580 A | 2/2002 |
| CN | 101120098 A | 2/2008 |

(Continued)

OTHER PUBLICATIONS

Sabounchi P, Morales AM, Ponce P, Lee LP, Simmons BA, Davalos RV. Sample concentration and impedance detection on a microfluidic polymer chip. Biomed Microdevices. Oct. 2008; 10(5):661-70.*
Manickam, A.; Chevalier, A.; McDermott, M.; Ellington, A.D.; Hassibi, A. A CMOS electrochemical impedance spectroscopy (EIS) biosensor array. IEEE Trans. Biomed. Circuits Syst. Apr. 2010, 379-390.*
Cagnin S, Caraballo M, Guiducci C, Martini P, Ross M, Santaana M, Danley D, West T, Lanfranchi G. Overview of electrochemical DNA biosensors: new approaches to detect the expression of life. Sensors (Basel). 2009;9(4):3122-48. Epub Apr. 24, 2009.*
U.S. Appl. No. 13/397,581, filed Feb. 15, 2012, Esfandyarpour et al.
U.S. Appl. No. 13/824,129, filed Mar. 15, 2013, Esfandyarpour et al.
U.S. Appl. No. 13/838,816, filed Mar. 15, 2013, Esfandyarpour et al.
Esfandyarpour, et al. 3D modeling of impedance spectroscopy for protein detection in nanoneedle biosensors. Proceedings of the COMSOL Conference 2007, Boston.

(Continued)

*Primary Examiner* — Samuel Woolwine
*Assistant Examiner* — Olayinka Oyeyemi
(74) *Attorney, Agent, or Firm* — Wilson Sonsini Goodrich & Rosati

(57) ABSTRACT

Aspects of the invention include methods for improving the accuracy and read length of sequencing reactions by utilizing unlabeled unincorporable nucleotides, or by rephasing colony based sequencing reactions. Other aspects include systems and devices for improved measurement of biological reactions associated with bead which may be removed, utilizing current measurement methods through the counter ions associated with said beads due to the presence of reactants bound or associated with said bead, wherein electrodes for generating and measuring said current may be within the Debye length of said bead. Other aspects of the invention include methods for determining concentrations of input samples, means for reuse of an array, methods and apparatus for separating beads with different charge levels from each other.

21 Claims, 38 Drawing Sheets

(56) References Cited

U.S. PATENT DOCUMENTS

| | | |
|---|---|---|
| 7,399,590 B2 | 7/2008 | Piepenburg et al. |
| 7,435,561 B2 | 10/2008 | Piepenburg et al. |
| 7,485,428 B2 | 2/2009 | Armes et al. |
| 7,615,382 B2 | 11/2009 | Wang et al. |
| 7,645,596 B2 | 1/2010 | Williams et al. |
| 7,649,358 B2 | 1/2010 | Toumazou et al. |
| 7,666,598 B2 | 2/2010 | Piepenburg et al. |
| 7,682,837 B2 | 3/2010 | Jain et al. |
| 7,686,929 B2 | 3/2010 | Toumazou et al. |
| 7,692,219 B1 | 4/2010 | Holm-Kennedy |
| 7,695,907 B2 | 4/2010 | Miyahara et al. |
| 7,763,427 B2 | 7/2010 | Piepenburg et al. |
| 7,824,890 B2 | 11/2010 | Hoser et al. |
| 7,875,440 B2 | 1/2011 | Williams et al. |
| 7,888,013 B2 | 2/2011 | Miyahara et al. |
| 7,932,034 B2 | 4/2011 | Esfandyarpour et al. |
| 7,948,015 B2 | 5/2011 | Rothberg et al. |
| 8,030,000 B2 | 10/2011 | Piepenburg et al. |
| 8,062,848 B2 | 11/2011 | Goldstein et al. |
| 8,062,850 B2 | 11/2011 | Piepenburg et al. |
| 8,071,308 B2 | 12/2011 | Piepenburg et al. |
| 8,114,591 B2 | 2/2012 | Toumazou et al. |
| 8,128,796 B2 | 3/2012 | Ishige et al. |
| 8,129,118 B2 | 3/2012 | Weindel et al. |
| 8,137,569 B2 | 3/2012 | Harnack et al. |
| 8,152,991 B2 | 4/2012 | Briman et al. |
| 8,173,401 B2 | 5/2012 | Chang et al. |
| 8,179,296 B2 | 5/2012 | Kelly et al. |
| 8,257,925 B2 | 9/2012 | Brown et al. |
| 8,426,134 B2 | 4/2013 | Piepenburg et al. |
| 8,460,875 B2 | 6/2013 | Armes et al. |
| 8,518,670 B2 | 8/2013 | Goldstein et al. |
| 8,574,846 B2 | 11/2013 | Piepenburg et al. |
| 8,580,507 B2 | 11/2013 | Piepenburg et al. |
| 8,585,973 B2 | 11/2013 | Esfandyarpour |
| 8,637,253 B2 | 1/2014 | Piepenburg et al. |
| 8,673,560 B2 | 3/2014 | Leamon et al. |
| 8,969,002 B2 | 3/2015 | Esfandyarpour et al. |
| 9,150,915 B2 | 10/2015 | Esfandyarpour et al. |
| 9,187,783 B2 | 11/2015 | Esfandyarpour et al. |
| 9,274,077 B2 | 3/2016 | Esfandyarpour et al. |
| 2002/0132245 A1 | 9/2002 | Boles et al. |
| 2003/0209432 A1 | 11/2003 | Choong et al. |
| 2004/0014201 A1 | 1/2004 | Kim et al. |
| 2004/0033492 A1 | 2/2004 | Chen |
| 2005/0009022 A1 | 1/2005 | Weiner et al. |
| 2005/0019784 A1 | 1/2005 | Su et al. |
| 2006/0008824 A1 | 1/2006 | Ronaghi et al. |
| 2006/0105373 A1 | 5/2006 | Pourmand et al. |
| 2006/0222569 A1 | 10/2006 | Barten et al. |
| 2007/0132043 A1 | 6/2007 | Bradley et al. |
| 2007/0184463 A1 | 8/2007 | Molho et al. |
| 2007/0275375 A1 | 11/2007 | Van Eijk |
| 2008/0009420 A1 | 1/2008 | Schroth et al. |
| 2008/0032295 A1 | 2/2008 | Toumazou et al. |
| 2008/0161200 A1 | 7/2008 | Yu et al. |
| 2008/0166727 A1 | 7/2008 | Esfandyarpour et al. |
| 2008/0171325 A1 | 7/2008 | Brown et al. |
| 2008/0176817 A1 | 7/2008 | Zhou et al. |
| 2008/0241841 A1 | 10/2008 | Murakawa et al. |
| 2008/0286762 A1 | 11/2008 | Miyahara et al. |
| 2008/0302732 A1 | 12/2008 | Soh et al. |
| 2008/0318243 A1* | 12/2008 | Haga et al. ............ 435/6 |
| 2009/0026082 A1 | 1/2009 | Rothberg et al. |
| 2009/0029385 A1 | 1/2009 | Christians et al. |
| 2009/0032401 A1* | 2/2009 | Ronaghi et al. ......... 204/549 |
| 2009/0048124 A1 | 2/2009 | Leamon et al. |
| 2009/0127589 A1 | 5/2009 | Rothberg et al. |
| 2009/0166221 A1 | 7/2009 | Ishige et al. |
| 2009/0170716 A1 | 7/2009 | Su et al. |
| 2009/0170724 A1 | 7/2009 | Balasubramanian et al. |
| 2009/0181385 A1 | 7/2009 | McKernan et al. |
| 2009/0191594 A1* | 7/2009 | Ohashi ................ 435/91.2 |
| 2010/0035252 A1 | 2/2010 | Rothberg et al. |
| 2010/0072080 A1 | 3/2010 | Karhanek et al. |
| 2010/0078325 A1 | 4/2010 | Oliver |
| 2010/0112588 A1 | 5/2010 | Farinas et al. |
| 2010/0137143 A1 | 6/2010 | Rothberg et al. |
| 2010/0151479 A1 | 6/2010 | Toumazou et al. |
| 2010/0159461 A1 | 6/2010 | Toumazou et al. |
| 2010/0163414 A1 | 7/2010 | Gillies et al. |
| 2010/0167938 A1 | 7/2010 | Su et al. |
| 2010/0188073 A1 | 7/2010 | Rothberg et al. |
| 2010/0197507 A1 | 8/2010 | Rothberg et al. |
| 2010/0209922 A1 | 8/2010 | Williams et al. |
| 2010/0255595 A1 | 10/2010 | Toumazou et al. |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2010/0317531 A1 | 12/2010 | Balasubramanian et al. |
| 2010/0330570 A1 | 12/2010 | Vander Horn et al. |
| 2011/0039266 A1 | 2/2011 | Williams et al. |
| 2011/0117026 A1 | 5/2011 | Tseng et al. |
| 2011/0118139 A1 | 5/2011 | Mehta et al. |
| 2011/0123991 A1 | 5/2011 | Hoser |
| 2011/0171655 A1 | 7/2011 | Esfandyarpour et al. |
| 2011/0177498 A1 | 7/2011 | Clark et al. |
| 2011/0183321 A1 | 7/2011 | Williams et al. |
| 2011/0195253 A1 | 8/2011 | Hinz et al. |
| 2011/0195459 A1 | 8/2011 | Hinz et al. |
| 2011/0201506 A1 | 8/2011 | Hinz et al. |
| 2011/0217697 A1 | 9/2011 | Rothberg et al. |
| 2011/0230375 A1 | 9/2011 | Rothberg et al. |
| 2011/0241081 A1 | 10/2011 | Rothberg et al. |
| 2011/0247933 A1 | 10/2011 | Rothberg et al. |
| 2011/0248319 A1 | 10/2011 | Rothberg et al. |
| 2011/0248320 A1 | 10/2011 | Rothberg et al. |
| 2011/0259745 A1 | 10/2011 | Dehlinger et al. |
| 2011/0263463 A1 | 10/2011 | Rothberg et al. |
| 2011/0287432 A1 | 11/2011 | Wong et al. |
| 2011/0287945 A1 | 11/2011 | Rothberg et al. |
| 2011/0294115 A1 | 12/2011 | Williams et al. |
| 2011/0311979 A1 | 12/2011 | Brown |
| 2012/0013392 A1 | 1/2012 | Rothberg et al. |
| 2012/0021918 A1 | 1/2012 | Bashir et al. |
| 2012/0034607 A1 | 2/2012 | Rothberg et al. |
| 2012/0037961 A1 | 2/2012 | Rothberg et al. |
| 2012/0040844 A1 | 2/2012 | Rothberg et al. |
| 2012/0045844 A1 | 2/2012 | Rothberg et al. |
| 2012/0055811 A1 | 3/2012 | Rothberg et al. |
| 2012/0055813 A1 | 3/2012 | Rothberg et al. |
| 2012/0061255 A1 | 3/2012 | Rothberg et al. |
| 2012/0061256 A1 | 3/2012 | Rothberg et al. |
| 2012/0061733 A1 | 3/2012 | Rothberg et al. |
| 2012/0065093 A1 | 3/2012 | Rothberg et al. |
| 2012/0071363 A1 | 3/2012 | Rothberg et al. |
| 2012/0085660 A1 | 4/2012 | Rothberg et al. |
| 2012/0088682 A1 | 4/2012 | Rothberg et al. |
| 2012/0094871 A1 | 4/2012 | Hinz et al. |
| 2012/0129173 A1 | 5/2012 | Piepenburg et al. |
| 2012/0129703 A1 | 5/2012 | Rothberg et al. |
| 2012/0129728 A1 | 5/2012 | Rothberg et al. |
| 2012/0129732 A1 | 5/2012 | Rothberg et al. |
| 2012/0135870 A1 | 5/2012 | Rothberg et al. |
| 2012/0135893 A1 | 5/2012 | Drmanac et al. |
| 2012/0138460 A1 | 6/2012 | Baghbani-Parizi et al. |
| 2012/0156728 A1 | 6/2012 | Li et al. |
| 2012/0157322 A1 | 6/2012 | Myllykangas et al. |
| 2012/0173159 A1 | 7/2012 | Davey et al. |
| 2012/0175252 A1 | 7/2012 | Toumazou et al. |
| 2012/0222496 A1 | 9/2012 | Mamigonians |
| 2012/0258456 A1 | 10/2012 | Armes et al. |
| 2012/0258499 A1 | 10/2012 | Piepenburg et al. |
| 2012/0264617 A1 | 10/2012 | Pettit |
| 2012/0295819 A1 | 11/2012 | Leamon et al. |
| 2012/0302454 A1 | 11/2012 | Esfandyarpour et al. |
| 2012/0322113 A1 | 12/2012 | Erlander et al. |
| 2013/0005613 A1 | 1/2013 | Leamon et al. |
| 2013/0023011 A1 | 1/2013 | Leamon et al. |
| 2013/0059290 A1 | 3/2013 | Armes et al. |
| 2013/0059762 A1 | 3/2013 | Leamon et al. |
| 2013/0090860 A1 | 4/2013 | Sikora et al. |

(56) References Cited

U.S. PATENT DOCUMENTS

| | | | |
|---|---|---|---|
| 2013/0096013 | A1 | 4/2013 | Esfandyarpour et al. |
| 2013/0225421 | A1 | 8/2013 | Li et al. |
| 2013/0231254 | A1 | 9/2013 | Kawashima et al. |
| 2013/0281307 | A1 | 10/2013 | Li et al. |
| 2014/0045701 | A1 | 2/2014 | Esfandyarpour et al. |
| 2014/0057339 | A1 | 2/2014 | Esfandyarpour et al. |
| 2014/0073531 | A1 | 3/2014 | Esfandyarpour |
| 2014/0099674 | A1 | 4/2014 | Piepenburg et al. |
| 2014/0235457 | A1 | 8/2014 | Esfandyarpour et al. |
| 2014/0329699 | A1 | 11/2014 | Esfandyarpour |
| 2015/0148264 | A1 | 5/2015 | Esfandyarpour et al. |
| 2015/0344943 | A1 | 12/2015 | Oberstrass |
| 2015/0368707 | A1 | 12/2015 | Esfandyarpour et al. |
| 2015/0376692 | A1 | 12/2015 | Esfandyarpour et al. |

FOREIGN PATENT DOCUMENTS

| | | | |
|---|---|---|---|
| CN | 101848757 A | 9/2010 | |
| CN | 102980922 A | 3/2013 | |
| EP | 1499738 B1 | 7/2008 | |
| EP | 1992706 A2 | 11/2008 | |
| EP | 2290096 A2 | 3/2011 | |
| EP | 2336361 A2 | 6/2011 | |
| EP | 2428588 A2 | 3/2012 | |
| EP | 2287341 B1 | 2/2013 | |
| EP | 1759012 B1 | 5/2013 | |
| EP | 2660336 A1 | 11/2013 | |
| GB | WO2010008480 * | 1/2010 | ............... C12Q 1/68 |
| JP | 2006512583 A | 4/2006 | |
| JP | 2008525822 A | 7/2008 | |
| WO | WO 01/18246 A1 | 3/2001 | |
| WO | WO-0137958 A2 | 5/2001 | |
| WO | WO 01/42508 A2 | 6/2001 | |
| WO | WO-0227909 A2 | 4/2002 | |
| WO | WO 02/061146 A1 | 8/2002 | |
| WO | WO 2005/008450 A2 | 1/2005 | |
| WO | WO 2005/108612 A2 | 11/2005 | |
| WO | WO 2005/121363 A2 | 12/2005 | |
| WO | WO-2007041619 A2 | 4/2007 | |
| WO | WO 2007/098049 A2 | 8/2007 | |
| WO | WO 2008/076406 A2 | 6/2008 | |
| WO | WO 2009/012112 A2 | 1/2009 | |
| WO | WO2009052348 * | 4/2009 | ............. G01N 27/26 |
| WO | WO-2009074926 A1 | 6/2009 | |
| WO | WO 2009/122159 A2 | 10/2009 | |
| WO | WO 2009/150467 A1 | 12/2009 | |
| WO | WO 2010/075188 A2 | 1/2010 | |
| WO | WO-2010026488 A2 | 3/2010 | |
| WO | WO 2010/037085 A1 | 4/2010 | |
| WO | WO2010047804 * | 4/2010 | ........... G01N 27/416 |
| WO | WO 2010/138187 A1 | 12/2010 | |
| WO | WO 2010/141940 A1 | 12/2010 | |
| WO | WO 2011/106556 A2 | 9/2011 | |
| WO | WO 2012/047889 A2 | 4/2012 | |
| WO | WO-2013188582 A1 | 12/2013 | |
| WO | WO 2014/012107 A2 | 1/2014 | |
| WO | WO 2014/043143 A1 | 3/2014 | |

OTHER PUBLICATIONS

Finn, et al. Efficient incorporation of positively charged 2′, 3′-dideoxynucleoside-5′-triphosphates by DNA polymerases and their application in 'direct-load' DNA sequencing. Nucleic Acids Res. Aug. 15, 2003;31(16):4769-78.

Hollis, et al. Structure of the gene 2.5 protein, a single-stranded DNA binding protein encoded by bacteriophage T7. Proc Natl Acad Sci U S A. Aug. 14, 2001;98(17):9557-62. Epub Jul. 31, 2001.

International search report and written opinion dated Feb. 26, 2013 for PCT/US2012/039880.

International search report and written opinion dated Mar. 19, 2013 for PCT/US2012/067645.

International search report and written opinion dated Apr. 13, 2012 for PCT/US2011/054769.

Kitano, et al. Molecular structure of RNA polymerase and its complex with DNA. J Biochem. Jan. 1969;65(1):1-16.

Office action dated Nov. 5, 2013 for U.S. Appl. No. 13/632,513.

Ren, et al. Rapid and sensitive detection of hepatitis B virus 1762T/1764A double mutation from hepatocellular carcinomas using LNA-mediated PCR clamping and hybridization probes. Journal of Virological Methods. 2009; 158:24-29.

Senapati, et al. A nonamembrane-based nucleic acid sensing platform for portable diagnostics. Topics in Current Chemistry. 2011; 304:153-169.

Voelkerding, et al. Next generation sequencing: from basic research to diagnostics. Clin. Chem. 2009; 55(4):641-658.

U.S. Appl. No. 14/119,859, filed Nov. 22, 2013, Esfandyarpour et al.

Office action dated Jan. 28, 2014 for U.S. Appl. No. 13/838,816.

Daniels, et al. Label-Free Impedance Biosensors: Opportunities and Challenges. Electroanalysis. May 16, 2007;19(12):1239-1257.

Daniels, et al. Simultaneous Measurement of Nonlinearity and Electrochemical Impedance for Protein Sensing Using Two-Tone Excitation. 30th Annual International IEEE EMBS Conference. Vancouver, British Columbia, Canada, Aug. 20-24, 2008. 5753-5756.

European search report and search opinion dated Mar. 12, 2014 for EP Application No. 11831452.5.

Piepenburg, et al. DNA detection using recombination proteins. PLoS Biol. Jul. 2006;4(7):e204.

U.S. Appl. No. 14/361,902, filed May 30, 2014, Esfandyarpour.

Notice of allowance dated Nov. 21, 2014 for U.S. Appl. No. 13/632,513.

U.S. Appl. No. 14/596,111, filed Jan. 13, 2015, Esfandyarpour et al.

Esfandyarpour, et al. A Novel Nanoneedle Biosensor for DNA Sequencing (abstract). Dec. 31, 2008. Available at http://www.nsti.org/Nanotech2008/showabstract.html?absno=1522.

European search report and search opinion dated Jan. 5, 2015 for EP Application No. 12792216.9.

Margulies, et al. Genome sequencing in microfabricated high-density picolitre reactors. Nature. Sep. 15, 2005;437(7057):376-80. Epub Jul. 31, 2005.

Office action dated Dec. 19, 2014 for U.S. Appl. No. 13/838,816.

Office action dated Jul. 23, 2014 for U.S. Appl. No. 13/824,129.

International search report and written opinion dated Aug. 21, 2014 for PCT Application No. PCT/US2014/027544.

Javanmard, et al. A microfluidic platform for electrical detection of DNA hybridization. Sens Actuators B Chem. May 20, 2011;154(1):22-27. Epub Mar. 30, 2010.

Office action dated Sep. 2, 2014 for U.S. Appl. No. 13/632,513.

Office action dated May 1, 2015 for U.S. Appl. No. 13/824,129.

Co-pending U.S. Appl. No. 14/688,764, filed Apr. 16, 2015.

Notice of allowance dated Jun. 3, 2015 for U.S. Appl. No. 14/596,111.

Co-pending U.S. Appl. No. 14/653,230, filed Jun. 17, 2015.

Notice of allowance dated Jul. 1, 2015 for U.S. Appl. No. 13/824,129.

Notice of allowance dated Jul. 13, 2015 for U.S. Appl. No. 14/596,111.

Co-pending U.S. Appl. No. 14/835,070, filed Aug. 25, 2015.

Co-pending U.S. Appl. No. 14/859,725, filed Sep. 21, 2015.

Edman; et al., "Electric field directed nucleic acid hybridization on microchips.", Dec. 15, 1997, 25(24), 4907-14.

"Notice of allowance dated Aug. 25, 2015 for U.S. Appl. No. 14/596,111.".

"Notice of allowance dated Sep. 1, 2015 for U.S. Appl. No. 14/596,111.".

"Office action dated Oct. 7, 2015 for U.S. Appl. No. 13/838,816.".

Sosnowski; et al., "Rapid determination of single base mismatch mutations in DNA hybrids by direct electric field control.", Feb. 18, 1997, 94(4), 1119-23.

Zhang; et al., "Dielectrophoresis for manipulation of micro/nano particles in microfluidic systems.", Jan. 2010, 396(1), 401-20.

(56) References Cited

OTHER PUBLICATIONS

Didion; et al., "Invaders: Recognition of Double-Stranded DNA by Using Duplexes Modified with Interstrand Zippers of 2'-O-(Pyren-1-yl)methyl-ribonucleotides.", doi: 10.1002/cbic.201300414. Epub Aug. 23, 2013, Sep. 2, 2013, 14(13), 1534-1538.

International search report and written opinion dated Oct. 26, 2015 for PCT/US2015/026135.

Notice of allowance dated Dec. 3, 2015 for U.S. Appl. No. 13/838,816.

Lee, et al. Ion-sensitive field-effect transistor for biological sensing. Sensors (Basel). 2009;9(9):7111-31. doi: 10.3390/s90907111. Epub Sep. 7, 2009.

Office action dated Apr. 9, 2015 for U.S. Appl. No. 14/596,111.

Notice of allowance dated Dec. 15, 2015 for U.S. Appl. No. 13/838,816.

Office action dated Dec. 17, 2015 for U.S. Appl. No. 14/835,070.

Office action dated Apr. 6, 2016 for U.S. Appl. No. 14/835,070.

\* cited by examiner

500

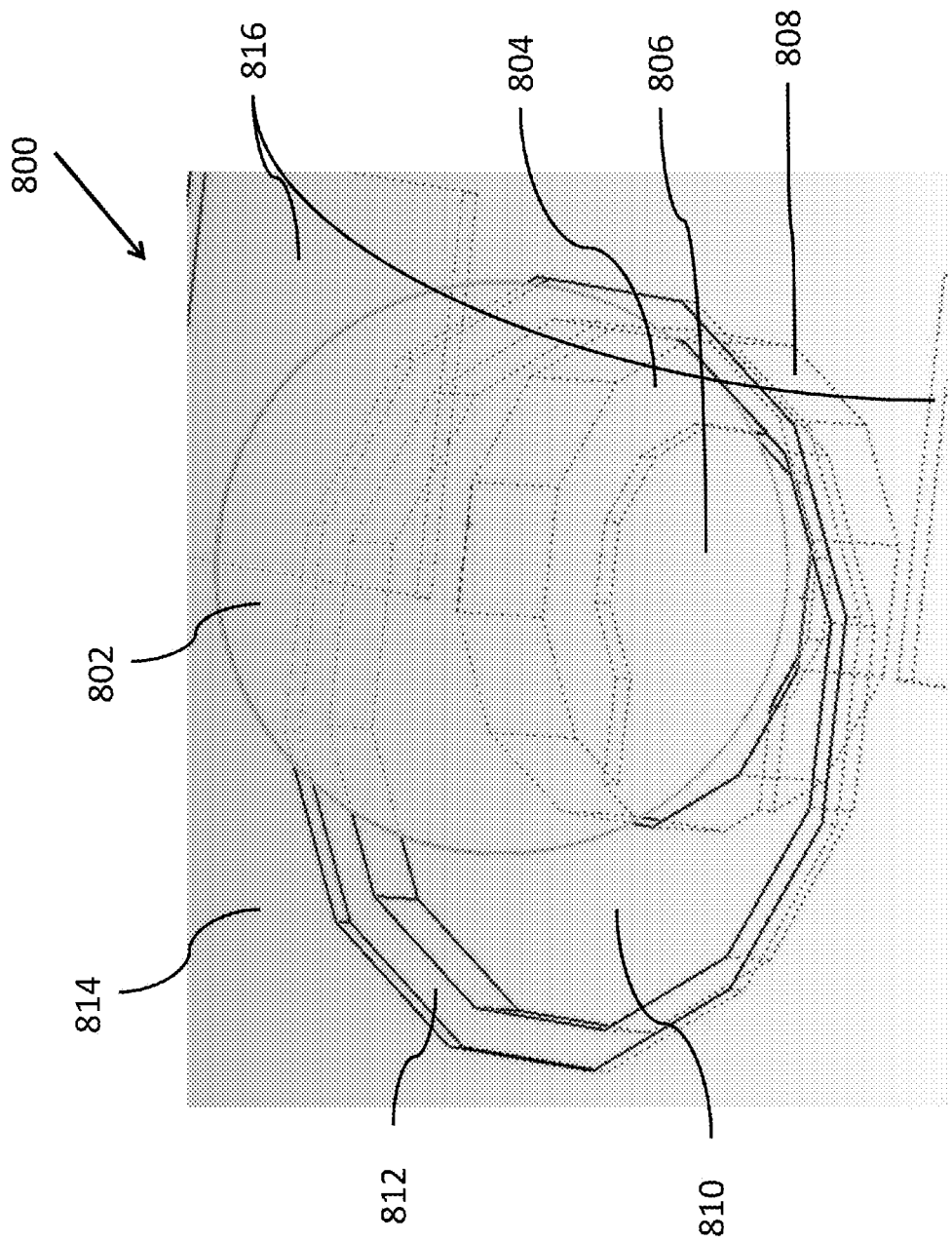

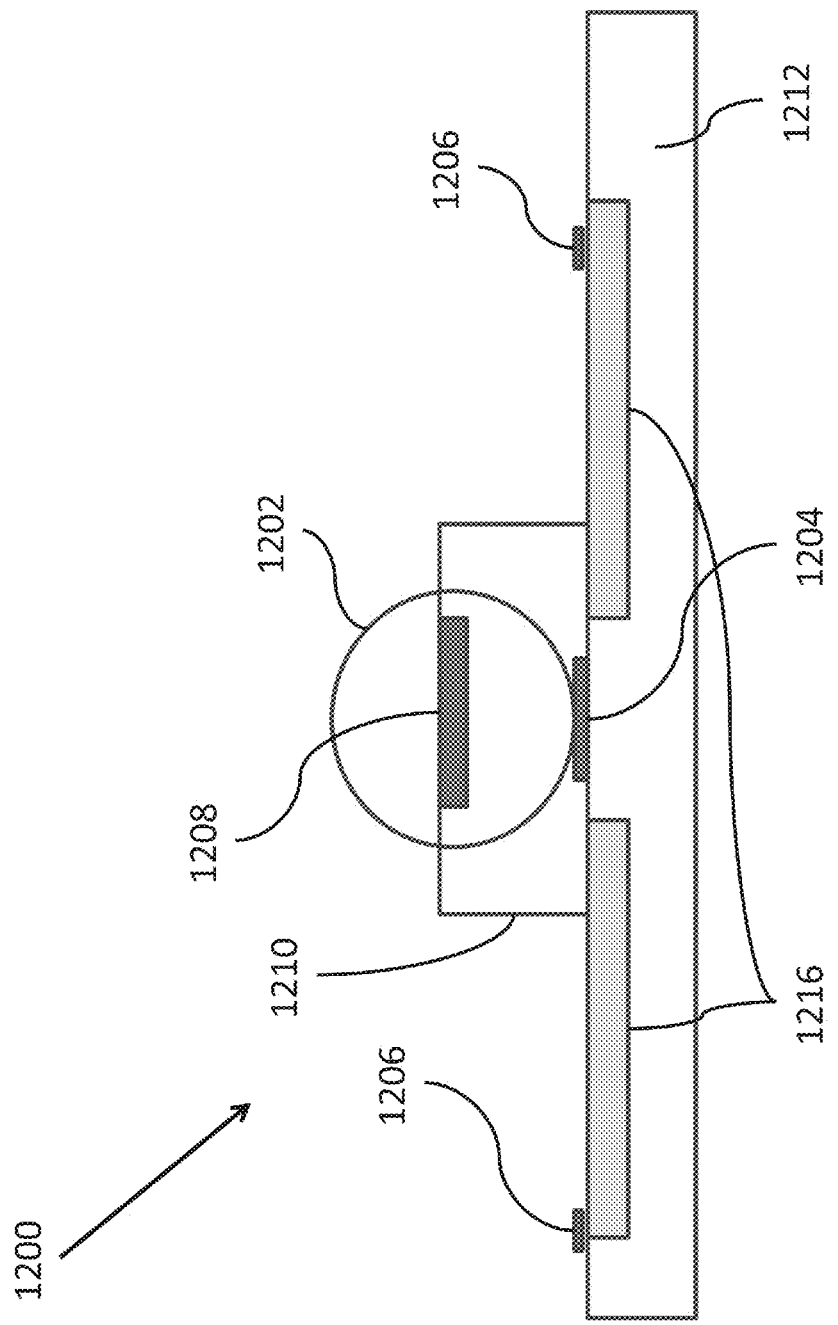

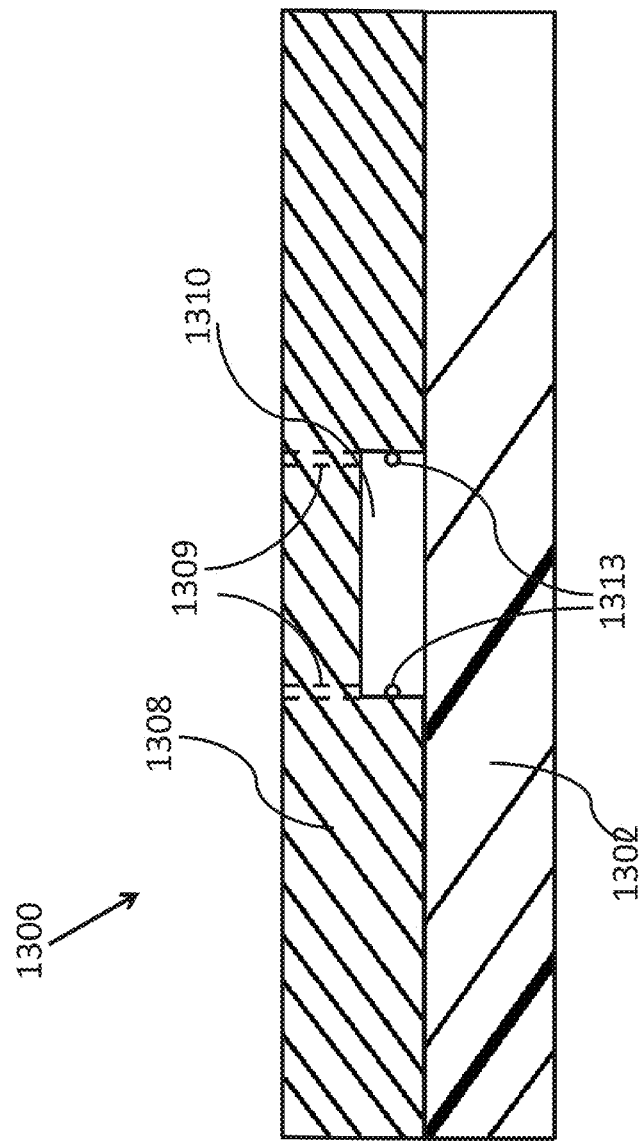

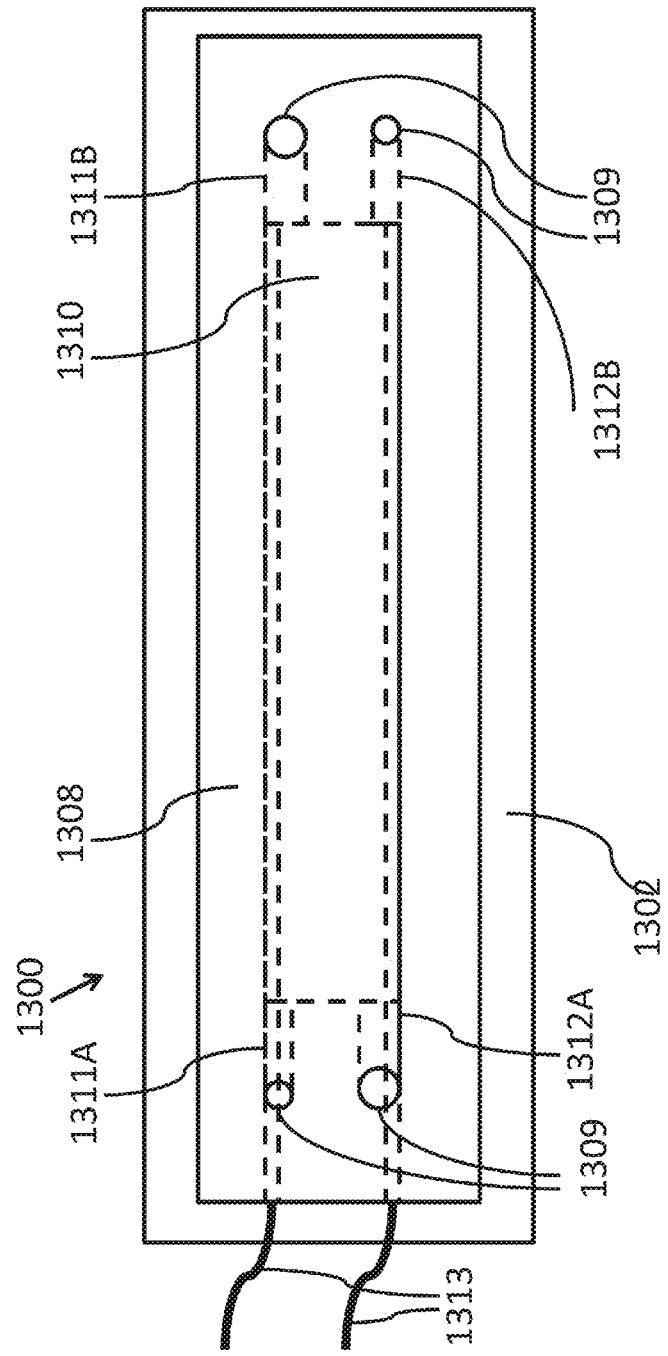

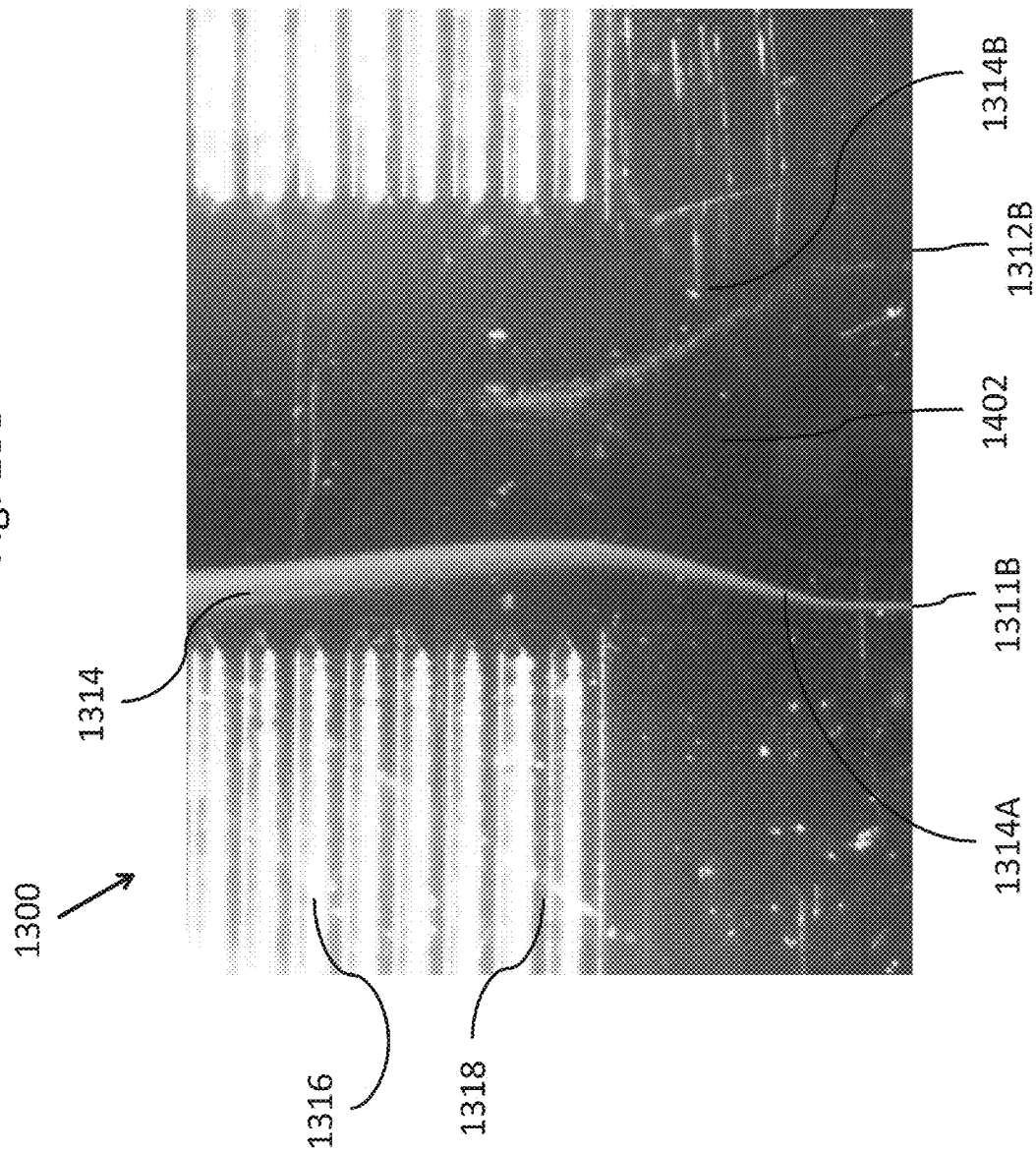

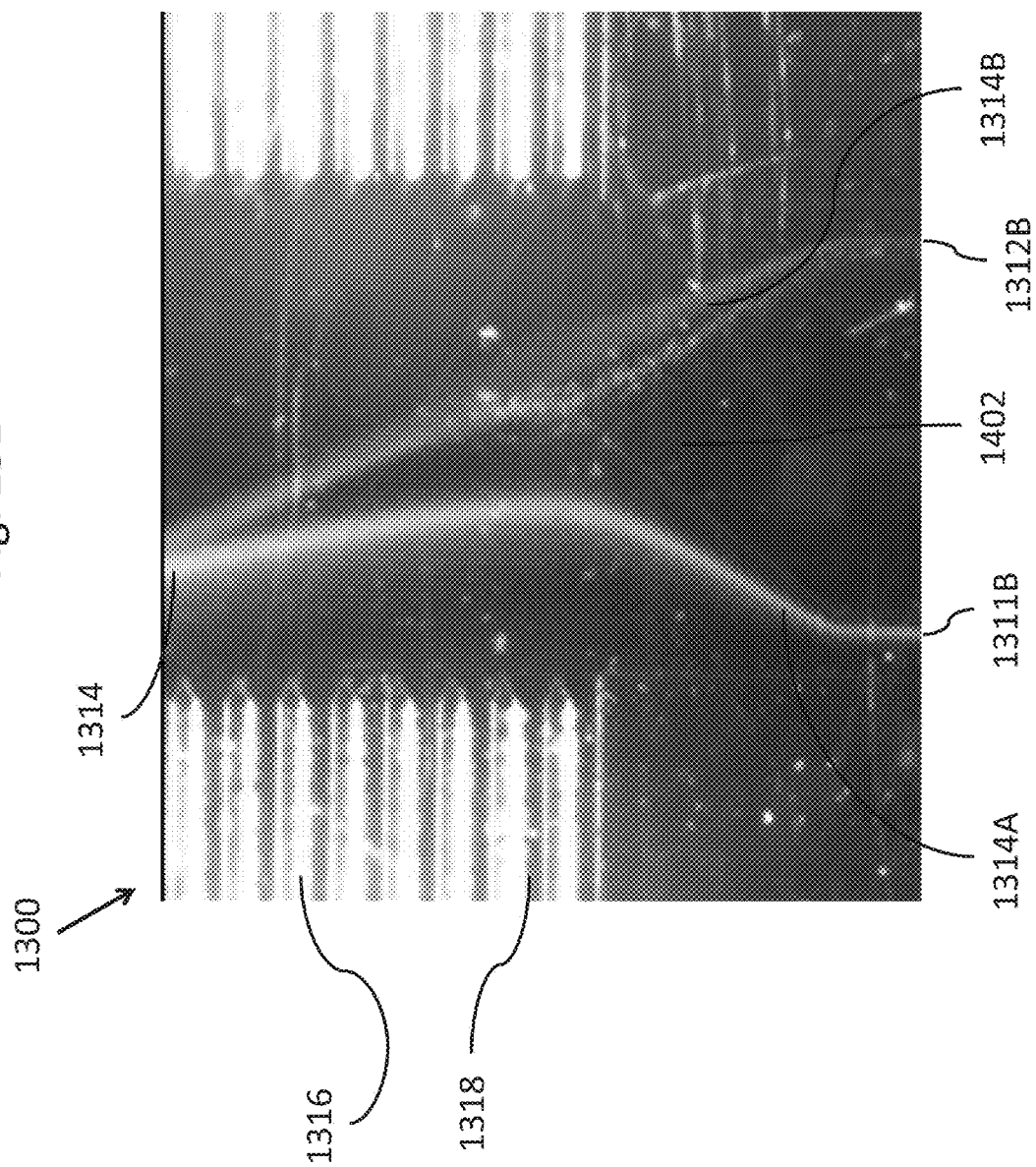

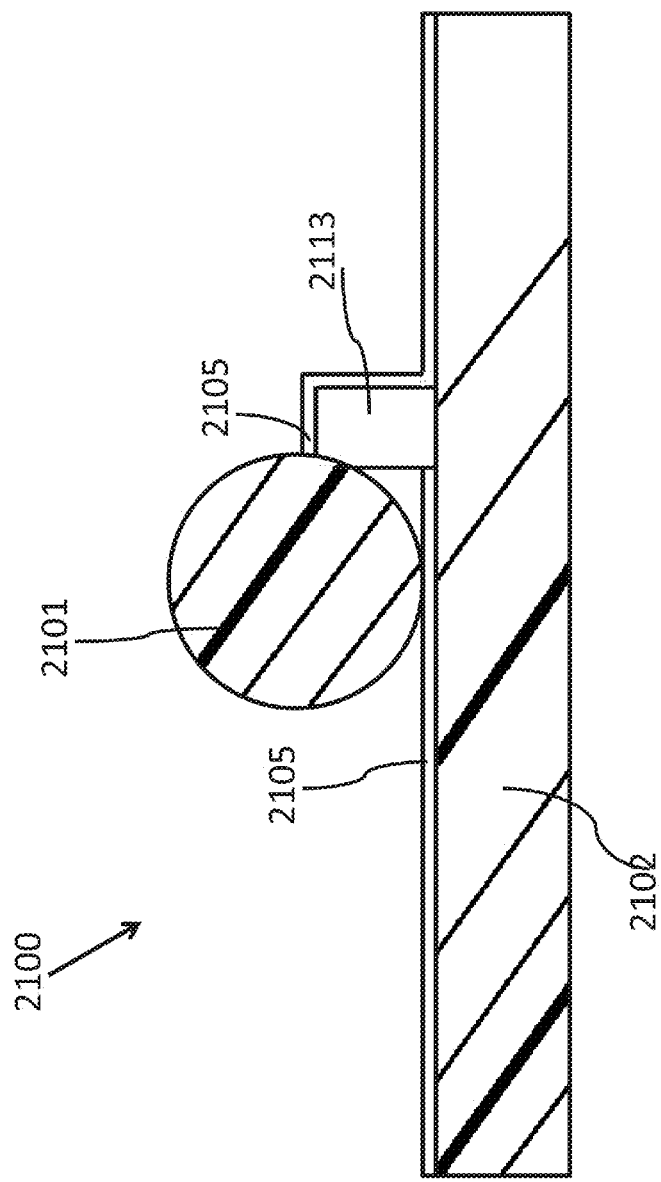

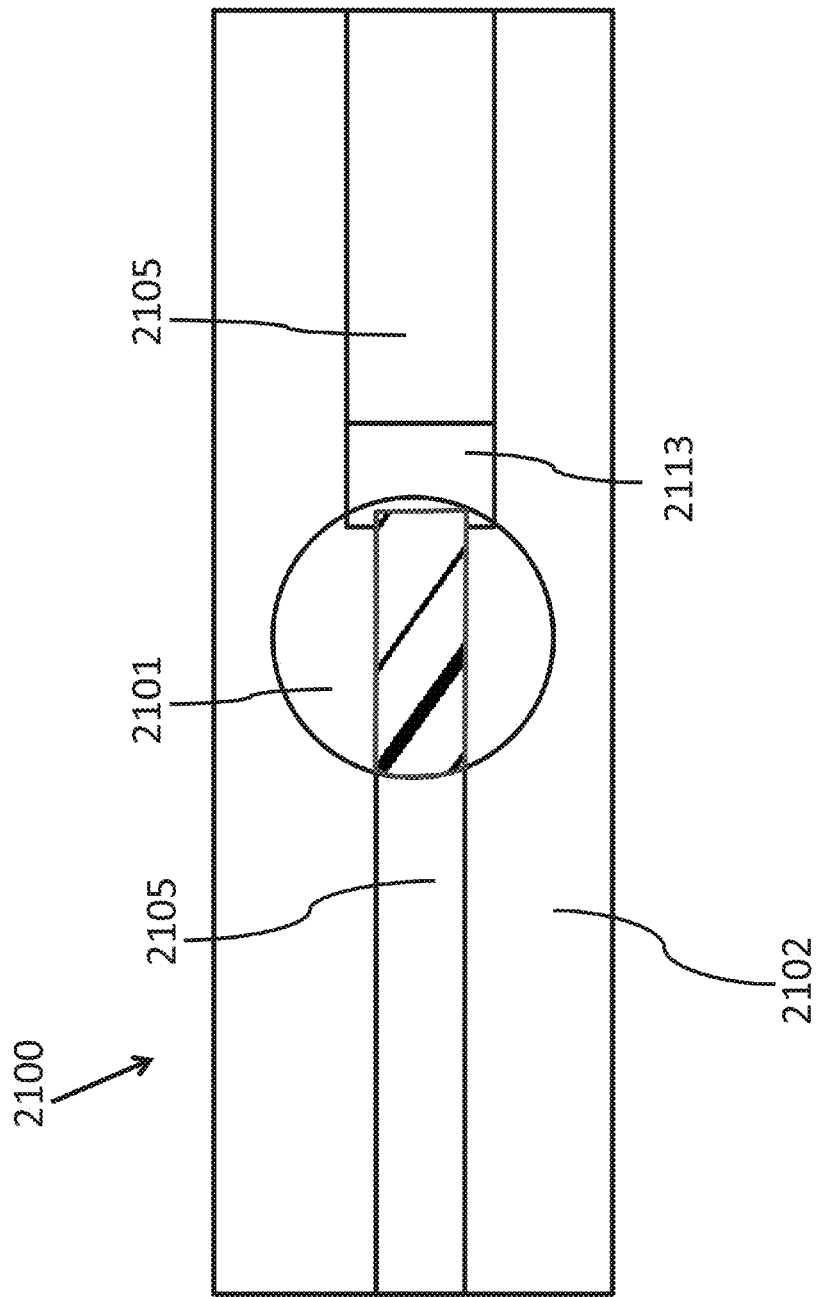

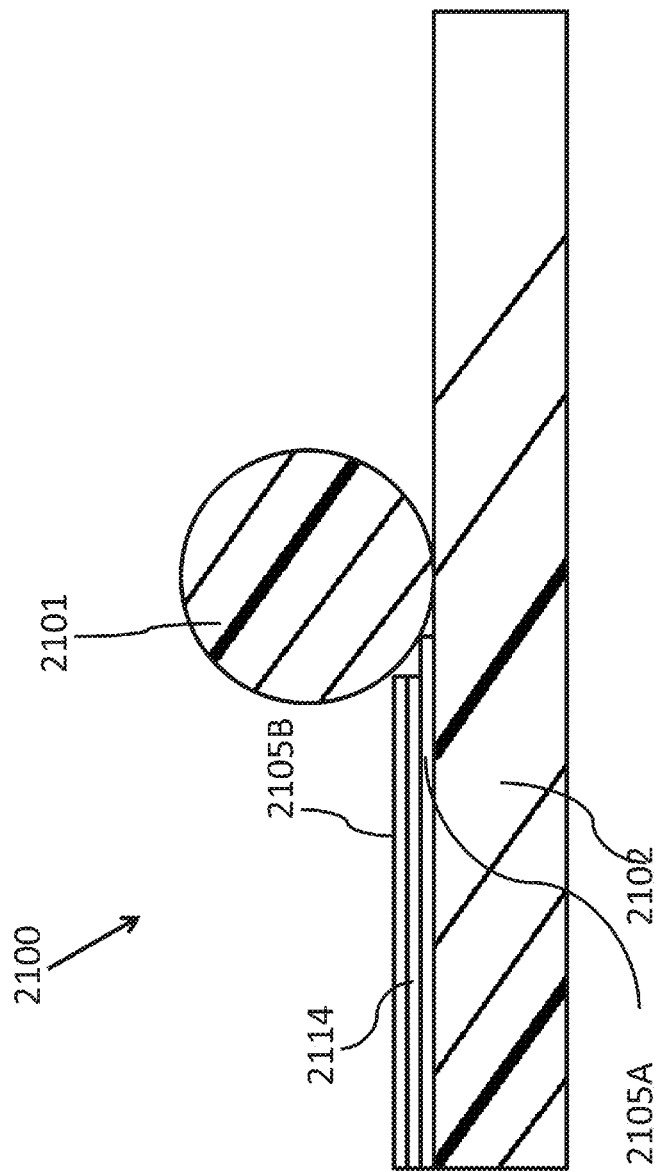

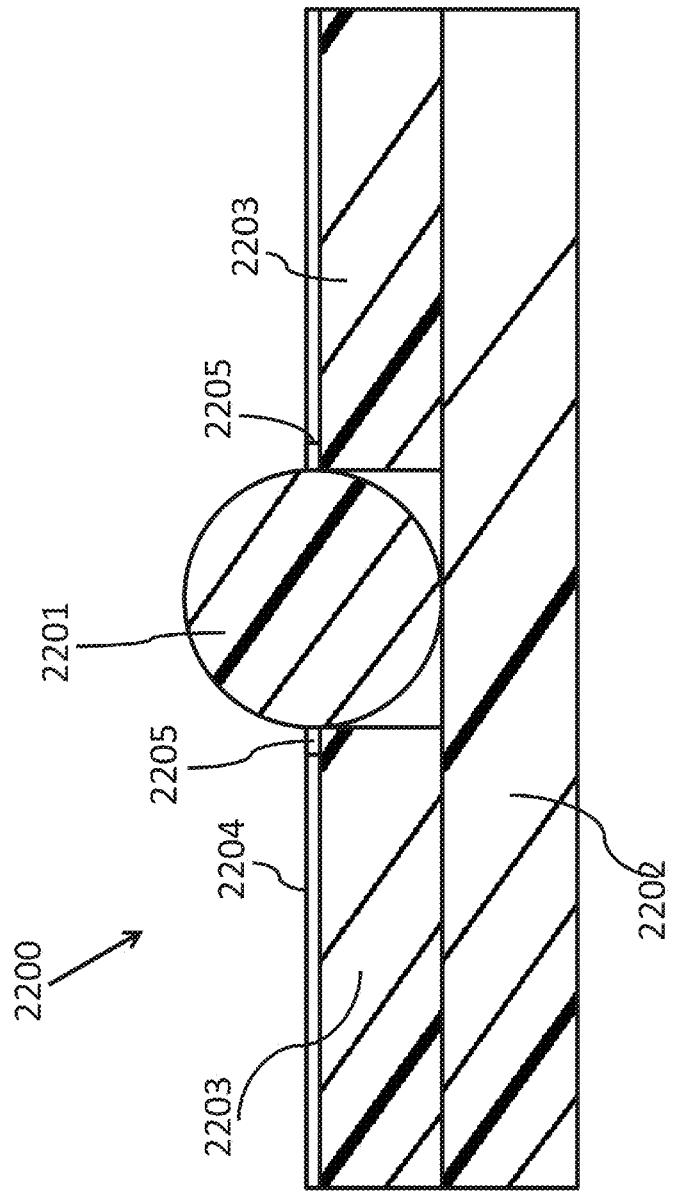

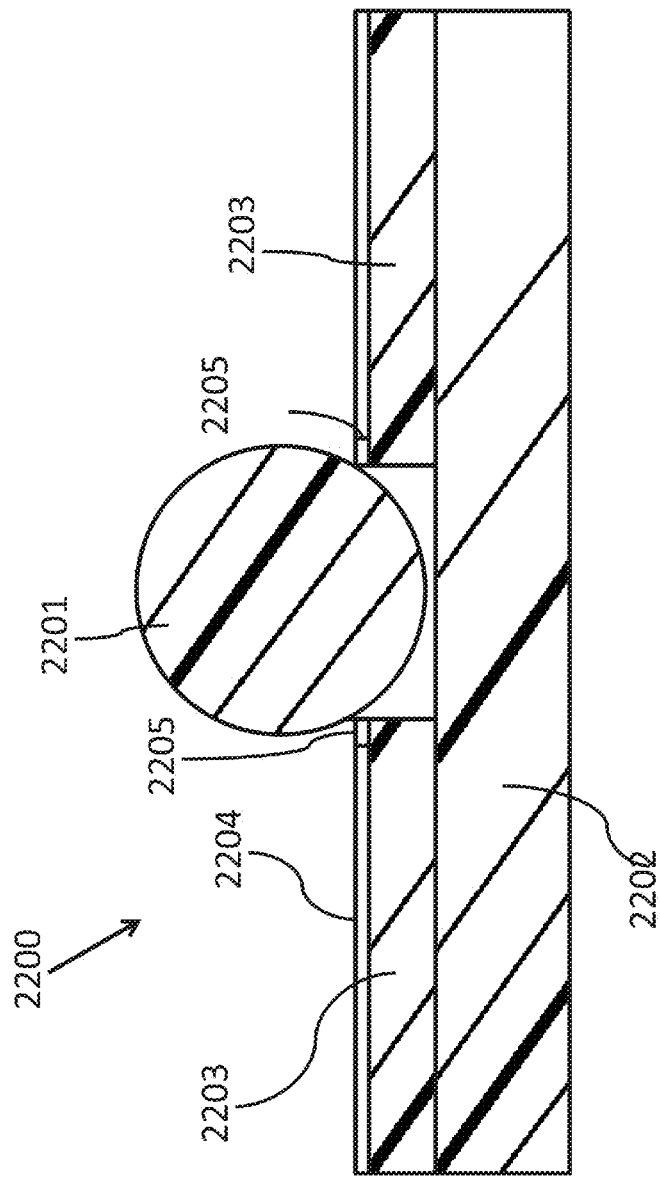

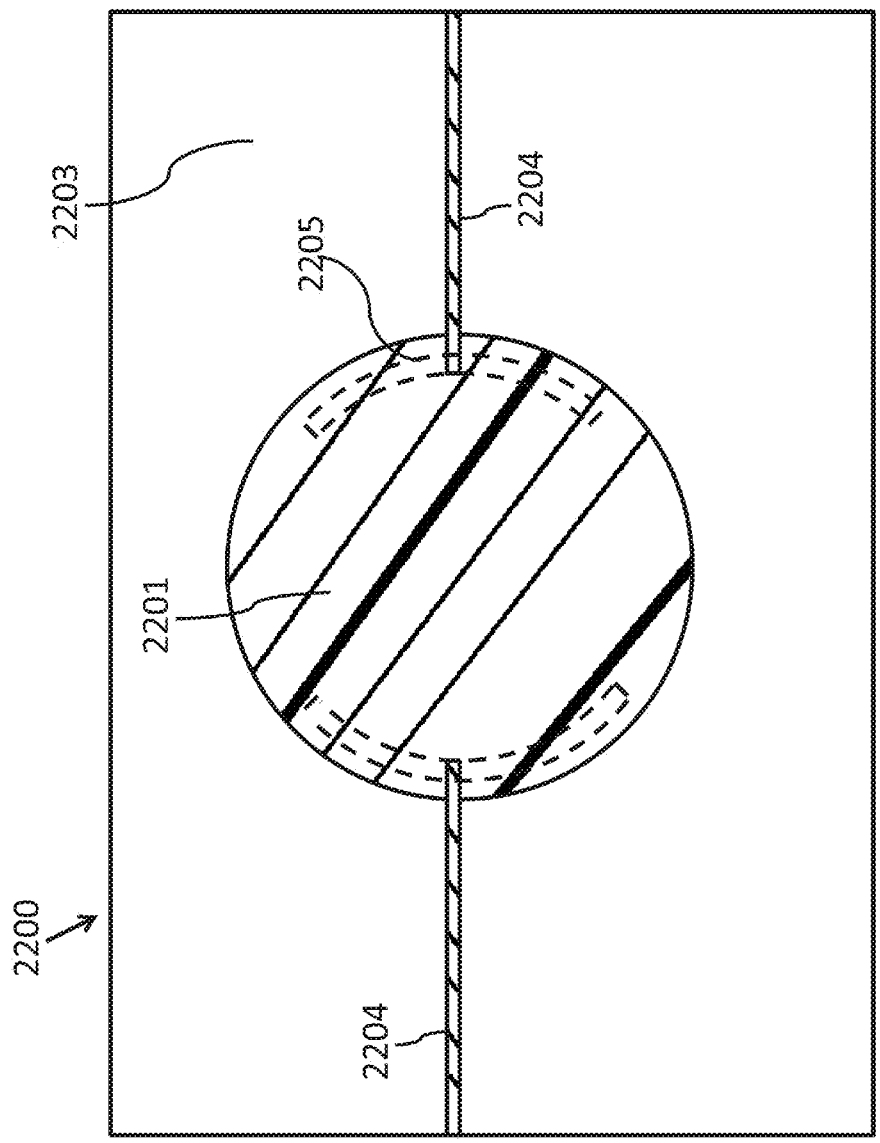

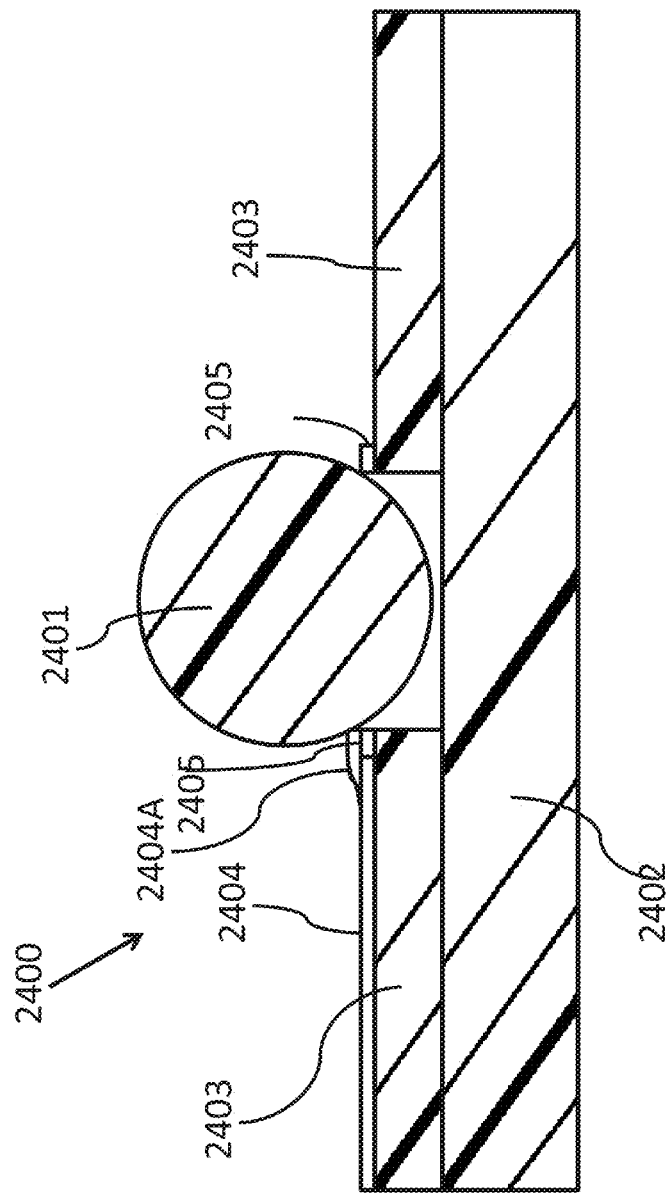

CHAMBER FREE NANOREACTOR SYSTEM

RELATED APPLICATIONS

This application is a continuation-in-part of PCT International Application Serial No. PCT/US2011/054769, filed Oct. 4, 2011, which claims the benefit of U.S. Provisional Patent Application Ser. No. 61/443,167 filed Feb. 15, 2011 and U.S. Provisional Patent Application Ser. No. 61/491,081 filed May 27, 2011 each of which applications is incorporated by reference in its entirety for all purposes. Application PCT/US2011/054769 also claims the benefit of U.S. Provisional Patent Application Ser. No. 61/389,490 filed Oct. 10, 2010 and U.S. Provisional Patent Application Ser. No. 61/389,484 filed Oct. 4, 2010.

STATEMENT REGARDING FEDERALLY SPONSORED RESEARCH AND DEVELOPMENT

This invention was made with government support under grant "Qualifying Therapeutic Discovery" grant awarded by IRS. The U.S. government may have certain rights in the invention.

The NanoNeedle may function as a pH sensor, as described in U.S. Provisional Application 61/389,490 titled "Integrated system and methods for polynucleotide extraction amplification and sequencing" which is hereby incorporated by reference in its entirety.

The system may utilize magnetic arrays, as described in U.S. Provisional Application 61/389,484 titled "MAGNETIC ARRAYS FOR EMULSION-FREE POLYNUCLEOTIDE AMPLIFICATION AND SEQUENCING, which is hereby incorporated by reference in its entirety.

The sensors may function in a virtual array, as described in U.S. Provisional Application 61/443,167 titled "CHAMBER-FREE GENE ELECTRONIC SEQUENCING TECHNOLOGIES", which is hereby incorporated by reference in its entirety.

The NanoBridge may function as a pH sensor, as described in U.S. application Ser. No. 13/252,315 titled "Integrated Biosensor Devices, Systems and Methods Therefor", which is hereby incorporated by reference in its entirety.

The magnetic array may be utilized in a manner similar to that described in U.S. Pat. No. 7,682,837 entitled "Devices and methods to form a randomly ordered array of magnetic beads and uses thereof", which is hereby incorporated by reference in its entirety.

The sensors may be used for detection of transient properties associated with incorporation events as described in U.S. Pat. No. 7,932,034 entitled "Heat and PH Measurement for Sequencing of DNA", which is hereby incorporated by reference in its entirety.

FIELD OF INVENTION

The present invention provides for methods and systems for Electronic DNA sequencing, single molecule DNA sequencing, and combinations of the above, providing low cost and convenient sequencing.

BACKGROUND OF THE INVENTION

Methods for quick and cost effective DNA sequencing (e.g., at high-throughput) remain an important aspect of advancing personalized medicine and diagnostic testing. Some known systems for DNA sequencing require that DNA samples be transferred between various subsystems (e.g., between the nucleic acid isolation subsystem and the amplification subsystem), thus resulting in inefficiencies and potential contamination. Some known methods for DNA sequencing employ optical detection, which can be cumbersome, expensive, and can limit throughput. Other systems utilize some forms of electronic sensing, but the sensor and sequencing flow cell may be one-time use disposables, which substantially increase the cost to the user, and limits the complexity of the sensor which may be cost effectively manufactured, as it will be thrown out after a single use. Some systems utilize amplification methods within the same flow cell, in which the sequencing is performed, binding the amplified directly to the flow cell, preventing reuse. Other systems utilize emulsion PCR, wherein beads and samples may be mixed into small emulsions utilizing low concentrations. Due to Poisson distribution, most of the beads and sample do not come together in an emulsion with a single bead and a single sample, and may be thus lost. The cost of the beads and amplification is a substantial portion of the cost of the sequencing, and most of that cost is thrown away without ever generating any useful data. The current system enables utilization of virtually all of the sample, thus reducing the cost to the user.

Current DNA sequencing systems typically need whole genome amplification in order to have sufficient sample, as the sample is very inefficiently utilized. Such whole genome amplification methods typically introduce significant amounts of bias in amplification in different portions of the genome, and require higher levels of coverage to overcome said bias. Methods for localizing samples, and reagents into a volume wherein a desired reaction or binding may occur is another aspect which is envisioned for the system, which may eliminate or reduce the need for whole genome amplification, and thus reduce the coverage needed.

Some systems exist for isolation of cells in flow through systems, such as described in US2011/0259745, but such systems utilize dielectrophoresis instead of electrophoresis to separate particles, and may be described as being able to differentiate between particles of similar size with different quantities of charge of the same sign associated therewith.

Thus, a need exists for improved systems and methods for extracting, amplifying and sequencing polynucleotides.

BRIEF SUMMARY OF THE INVENTION

The embodiments described herein relate to systems and methods for sequencing polynucleotides. In some embodiments the polynucleotides to be sequenced may be individual double or single stranded polynucleotides, as opposed to clonal polynucleotides.

BRIEF DESCRIPTION OF THE DRAWINGS

FIG. 8 shows an embodiment for a combined NanoNeedle sensor and magnetic array element.

FIG. 12 schematically illustrates a combined magnetic, virtual well, and NanoNeedle array element with a bead.

FIGS. 13A-13E show drawings, illustrations, and photomicrographs of various enrichment module embodiments.

FIGS. 21A-C schematically depicts an element of an array of a single side contact NanoNeedles.

FIGS. 22A-D schematically and diagrammatically show an element of an array of a double sided contact NanoNeedle.

FIGS. 24A-C schematically depicts views of a ring NanoBridge.

DETAILED DESCRIPTION OF THE INVENTION

Figure 1A:
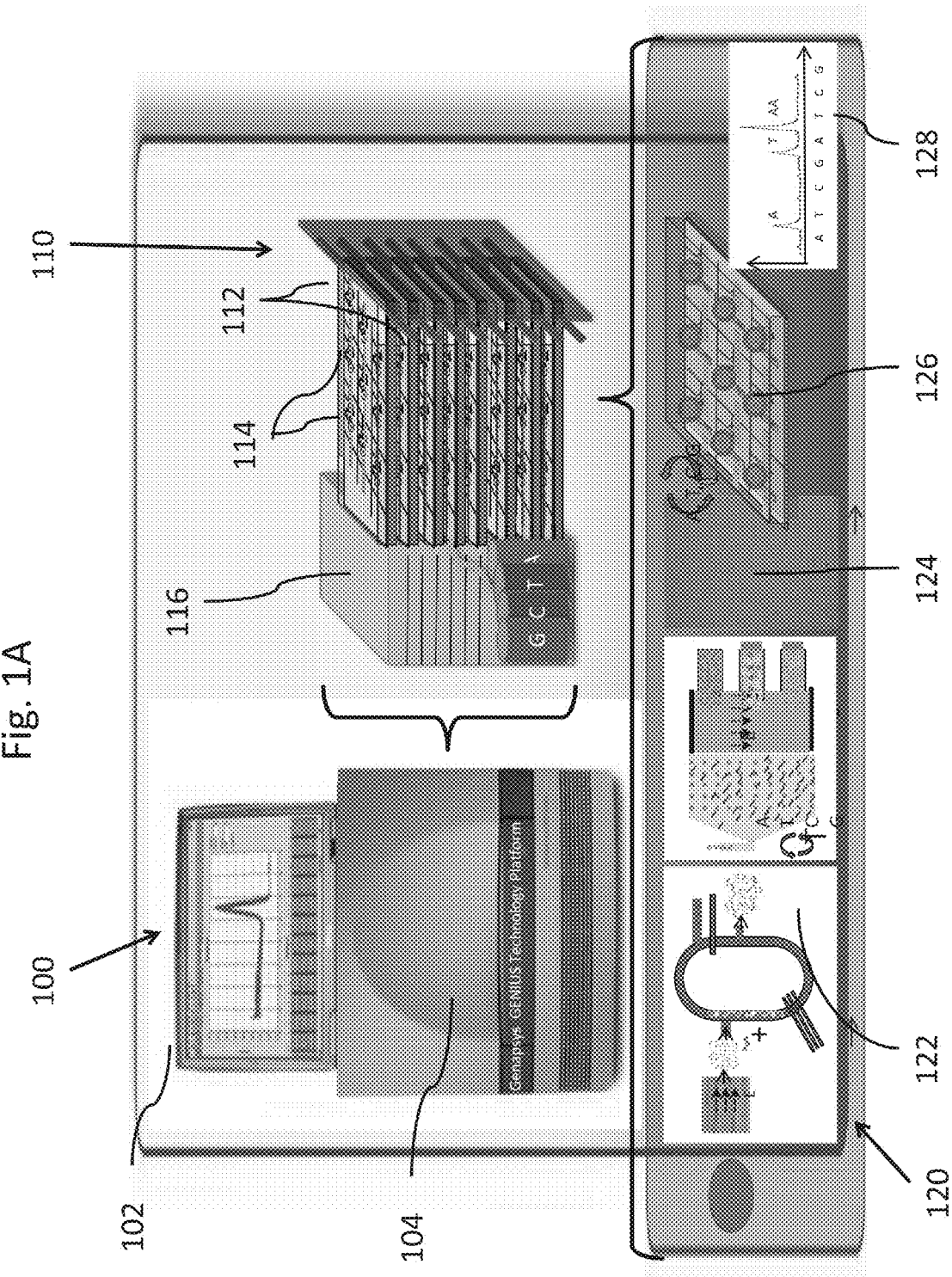
FIG. 1a shows a complete integrated system, along with schematic details of some subsystems.

As used herein, "bead" may mean beads, moieties or particles that may be spherical or non-spherical, wherein said beads, moieties or particles may be porous or solid or a mixture of solid and porous, and can include magnetic beads that may be may be paramagnetic, super-paramagnetic, diamagnetic, or ferromagnetic.

As used herein, "bead capture features" may mean features that can temporarily hold a single bead in a fixed position relative to the sensor and can include local magnetic structures on the substrate, depressions which may utilize an external magnet, local magnetic structures, Van der Waals forces, or gravity as forces that fix the position of a bead. Optionally, the bead may be bound in place using covalent or non-covalent binding.

As used herein, "clonal" may mean that substantially all of the populations of a bead or particle may be of the same nucleic acid sequence. In some embodiments there may be two populations associated with a single sample DNA fragment, as would be desired for "mate pairs," "paired ends", or other similar methodologies; the populations may be present in roughly similar numbers on the bead or particle, and may be randomly distributed over the bead or particle.

As used herein, "confinement" may mean when a molecule generated (such as DNA) at one bead or particle stays associated with the same bead or particle so as to substantially maintain the clonal nature of the beads or particles.

As used herein "isolate" may mean the prevention of migration, diffusion, flow, or other movement, from one virtual well to another virtual well as necessary to maintain the clonal nature of the beads or particles.

As used herein, "localized magnetic feature" may mean a magnetic feature created on a substantially planar substrate to hold individual beads on said substantially planar substrate.

As used herein, "localized magnetic field" may mean a magnetic field that substantially exists in the volume between the north pole of a first magnetic region and the south pole of a second magnetic region or substantially exists in the volume between the north and south poles of a single magnetic region.

As used herein, "nanosensor" may mean a sensor designed to detect beads or particles less than one of 0.1, 1, 5, 10 or 20 micrometers as measured on the diameter or the long axis for non spherical beads or particles. Alternatively, the sensor may be sensitive to moieties associated with said beads or particles, or with reaction products or byproducts wherein the reaction includes a moiety associated with said bead or particle. Said moieties may include DNA fragments, hydrogen ions, or other ions which may be counter ions and thus associated with said beads or particles or moieties bound or associated with said beads or particles. Nanosensors can include "NanoBridge, "NanoNeedle or ISFET sensors.

As used herein, "particle" can mean a non bead moiety such as a molecule, an aggregation of molecules, molecules bound to a solid particle, or particles, and other forms known in the art.

As used herein, "single phase liquid" is a liquid with relatively uniform physical properties throughout, including such properties as density, index of refraction, specific gravity, and can include aqueous, miscible aqueous and organic mixtures but does not include non miscible liquids such as oil and water. Among the physical properties not considered to potentially cause a liquid to not be considered a single phase liquid includes local variations in pH, charge density, and ionic concentration or temperature.

As used herein, "Substantially planar" shall allow small pedestals, raised sections, holes, depressions, or asperity which does not exceed 40 μm relative to the local plane of the device. Variations due to warpage, twist, cupping or other planar distortions may be not considered to constitute a portion of the permitted offset. Protrusions or depressions which may be not essential for the uses as described herein but which exceed 40 μm do not preclude a device from being considered substantially planar. Fluidic channels and or structures to generate said fluidic channels which have dimensions of greater than 40 μm also do not preclude a device from being considered substantially planar.

As used herein, "virtual wells" refers to local electric field or local magnetic field confinement zones where the species or set of species of interest, typically DNA or beads, generally does not migrate into neighboring "virtual wells" during a period of time necessary for a desired reaction or interaction.

As used herein, "NanoNeedle" refers to an impedance measuring sensor including two electrodes situated to measure the conductivity of the local environment in the active area between the electrodes.

As used herein, "NanoBridge" refers to a resistive device which may include a sensor which may respond to charge proximate to the active area of said resistive device, and wherein said resistive device may further be a semiconductor device.

As used herein, "electrode" is defined as any structure used for creating or applying the electric or magnetic force in such array. Such a structure may be used for isolation or manipulation in the delivery of a biomolecule to a special region in the array (e.g. the middle region of an element in the confinement or isolation array) at a time of interest resulting from turning on and off of the fields or forces.

As used herein, "phase error" is defined as the error wherein some fragments may be extended more or less than the consensus state of the bead. For fragments wherein a base is added where it shouldn't be added relative to the consensus, this phase error may be considered to be "leading". For other fragments wherein a base is not added where it should be added relative to consensus the fragment may be considered to be "lagging".

Integrated System

In some embodiments, the DNA sequencer may be part of a larger system, wherein more portions of the workflow may be automated. These portions of the workflow which may be automated may include cell lysis, DNA purification, DNA amplification, DNA library preparation, colony generation, sequencing, primary analysis and base calling, mapping of sequences to a reference, and determination of whether a genetic disease or other genetic characteristic is present. In some embodiments, the system may have more functionality, including a means to sort cells, such as cancer cells from blood, utilizing a flow cytometer or affinity pullout of desired or undesired cells.

FIG. 1A depicts a complete sequencing system 100, which may comprise an external computing device 102, and an integrated system 104. The integrated system may comprise a rack module 110, which may further comprise a fluidics interface subsystem 116, a set of sequencing/sample prep cards 112, and individual sequencing subsystems 114 on each sequencing/sample prep card 112. Schematic of sequencing/sample prep 120 includes library prep 122, re-useable magnetic arrays 124, which may further comprise sequence detectors 126, which result in sequencing data 128. In some embodiments of the current invention, a charge or pH sensitive detector may be used to determine the sequence of a DNA colony. A colony may be generated on a bead, the bead may be transferred to a sensor location, provided with primers, polymerase, and dNTPs whilst observing the change in charge or pH due to the incorporation of dNTPs utilizing said sensors. There may be a one to one correspondence between a sensor location and a colony.

Library Prep

Figure 1B:
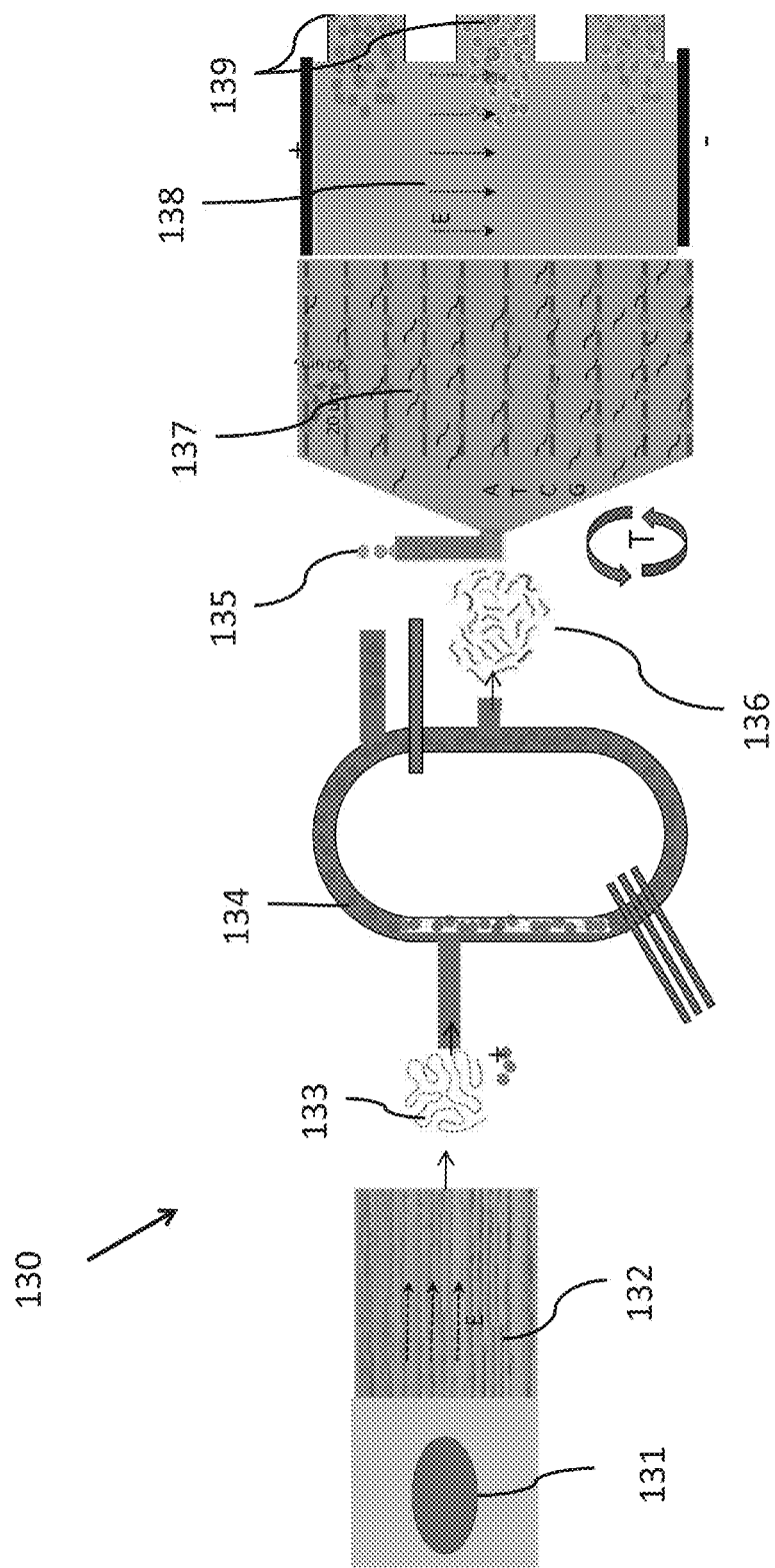
FIG. 1b shows schematic details of a sample and library prep subsystem.

FIG. 1B depicts a complete library prep subsystem 130, which includes sample cell input 131, cellular lysis and protein removal 132 resulting in un-fragmented genomic DNA 133, which may be input to a fragmentation and separation subsystem 134, which may thence output fragmented genomic DNA 136, which may be transported along with a set of beads 135, to a virtual well array 137 for amplification, and thence said beads may be separated utilizing a field 138 in an bead enrichment module 139 into sets of beads with amplification from set of beads without amplification.

Figure 1C:
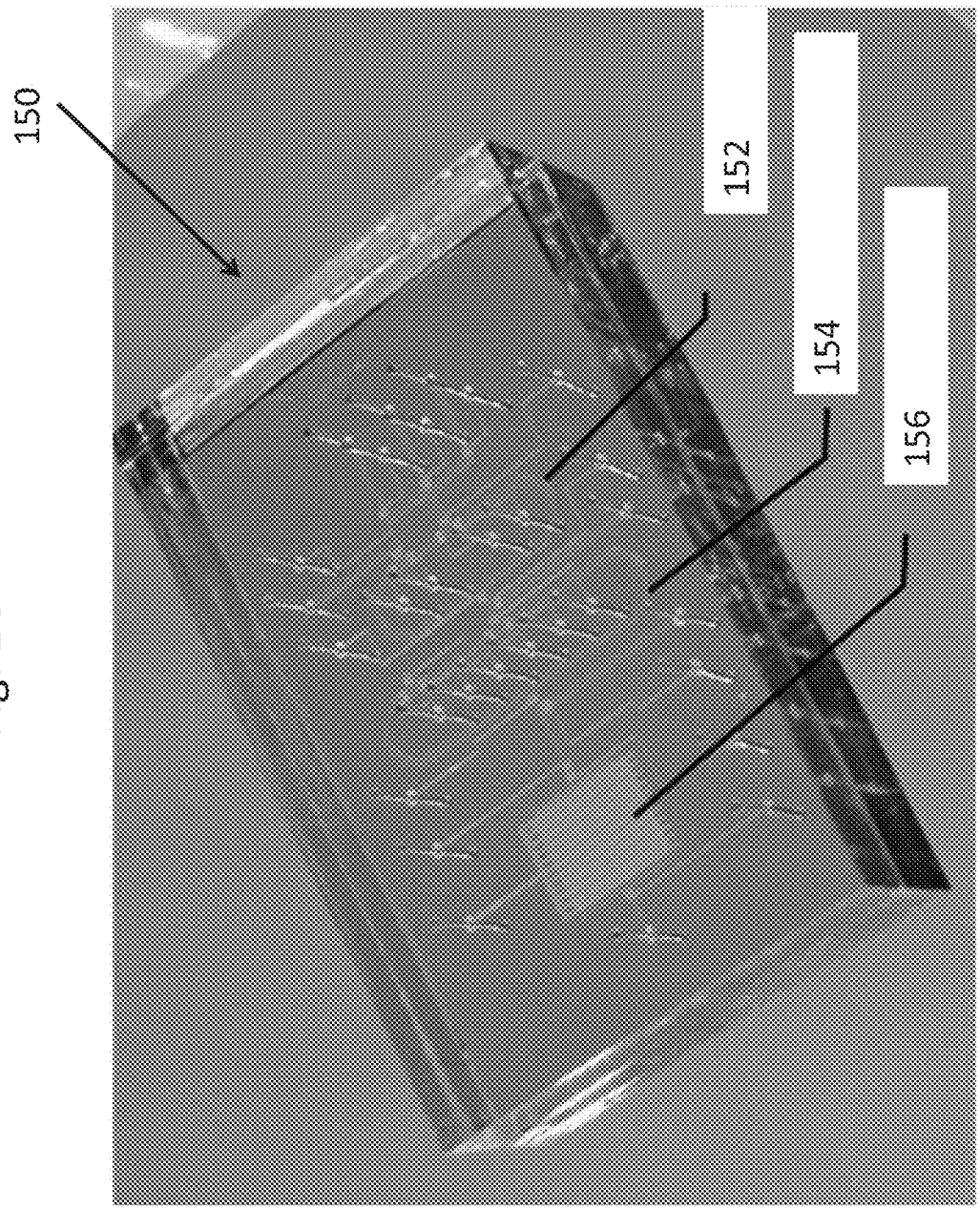
FIG. 1C shows a PDMS library preparation subsystem.

FIG. 1C shows an embodiment of a PDMS library preparation module 150 which includes a lysis section 152, a protein removal section 154, and an amplification section 156.

Sample Input

It may be desirable to process multiple samples in a single chip, since many projects do not require the full capacity of a chip. Other projects may have a single sample that would exceed the capacity of the chip. In some embodiments one or more samples could be introduced into the instrument in individual tubes, tube strips, 96-well plates, 384-well plates, etc. In some embodiments the sample wells could be sealed to prolong life on the instrument. In other embodiments the plates may be cooled to increase sample life. In other embodiments the samples could be accessed in a software selectable manner by a robotic pipettor.

Sample Concentration Determination

Prior to amplification the beads will need to be loaded with a single DNA fragment in order to create monoclonal beads. Typically the DNA concentration is determined and then it is introduced to beads in a dilute form so that on average less than 1 fragment will bind to each bead. Many beads have zero DNA fragments, fewer have a single fragment and a small number have 2 or more fragments. The steps needed for quantitation often require a separate instrument and separate processing.

In one embodiment a target concentration is created by a hybridization based pullout. A solid support such as pull-out beads may be functionalized with a controlled number of binding sites. In some embodiments these could be DNA primer compliments. The unamplified sample may have known primers ligated on each end. In some embodiments the primers may hybridize to the DNA on the pull-out beads. After the hybridization sites are fully occupied residual DNA may be washed away, and the DNA bound to the beads may subsequently be denatured releasing a known quantity of DNA.

In another embodiment the primers ligated to each DNA fragment may be bound to the primer compliment and detected using fluorescence detection of an intercalating dye. Since the primers are of a known length, the signal level will be proportional to the number of fragments. In another embodiment polymerase and associated dNTPs could be introduced creating full length double stranded DNA. When combined with the information from the primer signal the full length intercalating dye signal level would then allow determination of the mean fragment length.

In another embodiment dielectrophoresis could be used to concentrate DNA. During or after concentration the electrical current could be measured to determine the DNA concentration. In another embodiment the concentrated DNA could be quantitated by the use of intercalating dyes as described above.

In another embodiment, the concentration of said DNA may be determined directly by optical absorbance. Said optical absorbance determination may, for example, utilize an optical source which produces light at 260 nm.

In one embodiment the sample may be made very dilute and/or a small volume of sample reagent and loaded onto beads. DNA would bind to some of the beads and then be amplified in the virtual reactors creating beads with DNA. The sequencing primer may be made shorter than the compliment ligated to the sample DNA. Since the sequence is known, the correct dNTPs could be added and detected. In one embodiment multiple dNTPs may be simultaneously added. For example, if all dNTPs are added the polymerase would extend to the end of the fragment generating a large signal. Said large signal could be generated as a part of the amplification process. This may allow the detection and counting of the number of beads that have DNA even if the beads had minimal amplification. Knowing how many beads have signal may allow calculation of the proper dilution to generate the ideal number of monoclonal beads.

Similarly, measurements made using electrical current, optical signals, or other signals which indicate the concentration of DNA in the sample may be utilized to determine the dilution level, if any, needed to optimally utilize the DNA in the system.

In some embodiments, dilution may be needed to properly generate colonies in a system which generates colonies. Similarly dilution may be needed to for a nanopore system in order to prevent pore clogging, and conversely, to optimize the duty cycle whereby a pore may be occupied with a DNA strand. Dilution may be effectualized as part of a system which may improve the utilization of an emulsion PCR system utilized for generating clones, a bridge PCR system utilized for generating clones, a nanopore sequencing system, or a single molecule optical system, In other embodiments, concentration may be implemented as part of system, and may be effectuated by dielectrophoresis, hybridization, ethanol precipitation or other methods, and may be utilized to increase the concentration of DNA to improve the utilization of an emulsion PCR system utilized for generating clones, a bridge PCR system utilized for generating clones, a nanopore sequencing system, or a single molecule optical system.

A primary system may determine the concentration of template DNA using software or hardware to make said determination, and may then either concentrate or dilute as needed prior to utilizing said template DNA in the next appropriate step said system, which may be amplification or sequencing. Said determination step may also make use of a prior calibration step, which may utilize standard comprising DNA of a known concentration, or may utilize DNA which may be of an initially unknown concentration, wherein the concentration may be determined utilizing a separate system, and whereby the determined concentration of said DNA may be entered transferred, or otherwise communicated to said primary system. Said primary system may store any values needed for calibration locally in the said primary system, or may store it in a part of a larger system, or in a separate computer, or in a data base. Said calibration information which is stored may also include additional information, such as the time of calibration, the operator, the sample or standard utilized for calibration, or other information as may be determined to be relevant.

Sample Concentration Onto Amplification Regions

Many current systems currently utilize whole genome amplification of their sample in order to get have sufficient DNA sample at a high enough concentration for their protocol. Typical amplification methods may utilize degenerate primers and PCR, random hexamers and isothermal amplification or other methods for amplification of genomic DNA. Said amplification may amplify genomic DNA by a thousand fold or more. This amplification can introduce bias and is an additional cost in time and resources. The ability to reduce or eliminate the need to amplify the sample is desirable. In one embodiment the beads to be loaded are located in a flow cell, where in said beads may be retained by a magnetic field, and sample is pumped such that said sample may interact and bind with said beads. The sample can be pumped through the bead bed multiple times to provide additional opportunities for the sample to bind. The high surface area to volume should allow minimal sample to be used. The beads can subsequently be moved into a flow cell whereby they may be held in place by a magnetic array, and local colonies may be created on the beads by PCR or isothermal amplification.

In another embodiment the sample may be concentrated in the amplification region using the existing electrodes of the emulsion free nano-reactor. In one embodiment electrodes may be established on a single plane. In another embodiment electrodes may be added to a second plane parallel to the plane of the virtual reactors. In other embodiments mixtures of AC and DC voltage inputs are anticipated, and said voltages may be continuous or pulsed.

In other embodiments, whole genome amplification or targeted amplification, such as amplification which targets the exome, the conserved regions of the genome, a cancer panel, or other targets of interest may be implemented as part of a subsystem within an integrated system. Said targeted amplification may also incorporate barcodes for different samples as a part of the said amplification process. Said amplified DNA may then have its concentration determined as explained herein, prior to undergoing clonal amplification for subsequent sequencing utilizing a clonal sequencing subsystem and method which may be a part of said integrated system, or sequencing directly utilizing a single molecule sequencing subsystem and method which may be a part of said integrated system.

Loading Multiple Samples

Since many projects may not require the full use of a sequencing chip or flow cell it may be desirable to load multiple samples into different portions or areas of a single chip or flow cell. In one embodiment, samples are directed into separate zones separated by walls on the chip or flow cell using valves integrated into the chip or flow cell assembly. Such valves may be PDMS valves integrated into the fluidic path. In another embodiment there may be separate zones with separate inputs and outputs. In another embodiment samples may be directed into separate zones on a chip or flow cell using a local electric field. A positive field may be applied to attract DNA to desired regions, while a negative field may be applied to repel DNA from undesired regions. In another embodiment samples may be directed into separate zones using electromagnets to control the positioning of magnetic or paramagnetic beads. In another embodiment samples may be delivered into individual lanes using self sealing ports. Self sealing ports can include rubber septa and needles.

In another embodiment samples can be injected at different time points and new beads and bead locations can be distinguished utilizing sensor signals relative to that previously determined for said sensors wherein said bead locations where previously empty.

In a further embodiment, electro-wetting or opto-electrowetting may be utilized to deliver samples to distinct and separate regions of a chip or flow cell.

Reagent Storage

Reagent Cooling

In some embodiments of the current invention containers for the reagents may be cooled as needed, for example, regents which contain samples, polymerase, phosphatase, or other enzymes may need cooling, for instance, to about four Celsius.

In some embodiments of the current invention, the amount of reagent contained in the lines leading from the reagent containers to the valve manifold may contain a volume which is significant relative to that which is needed to perform a sequencing reaction. In order to prevent needing to discard this reagent, for example, at the beginning of a new sequencing run, it may be desirable to cool the lines from where they interface with the reagent containers, up to, or close to, where they enter the valving manifold. In some embodiments, where the valving manifold is sufficiently separated from where reagents enter the flow cell where sequencing or another reaction occurs to permit the flow cell and the valving manifold to operate at different temperatures, for example, about four Celsius and 20 to 40 Celsius respectively, it may be desirable to cool the valving manifold as well.

Virtual Well

The a virtual well or "chamber-free array", may detect or manipulate particles (e.g., beads, cells, DNA, RNA, proteins, ligands, biomolecules, other particulate moieties, or combinations thereof) in an array wherein said array captures, holds, confines, isolates or moves the particles through an electrical, magnetic or electromagnetic force and may be used for a reaction and or detection of the particles and or a reaction involving said particles. Said "virtual well" may provide a powerful tool for capturing/holding/manipulating of beads, cells, other biomolecules, or their carriers and may subsequently concentrate, confine, or isolate moieties in different pixels or regions of the array from other pixels or regions in said array utilizing electrical, magnetic, or electromagnetic force(s). In one embodiment the array is in a fluidic environment. Sensing may be done by measurement of charge, pH, current, voltage, heat, optical or other methods.

Figure 2:
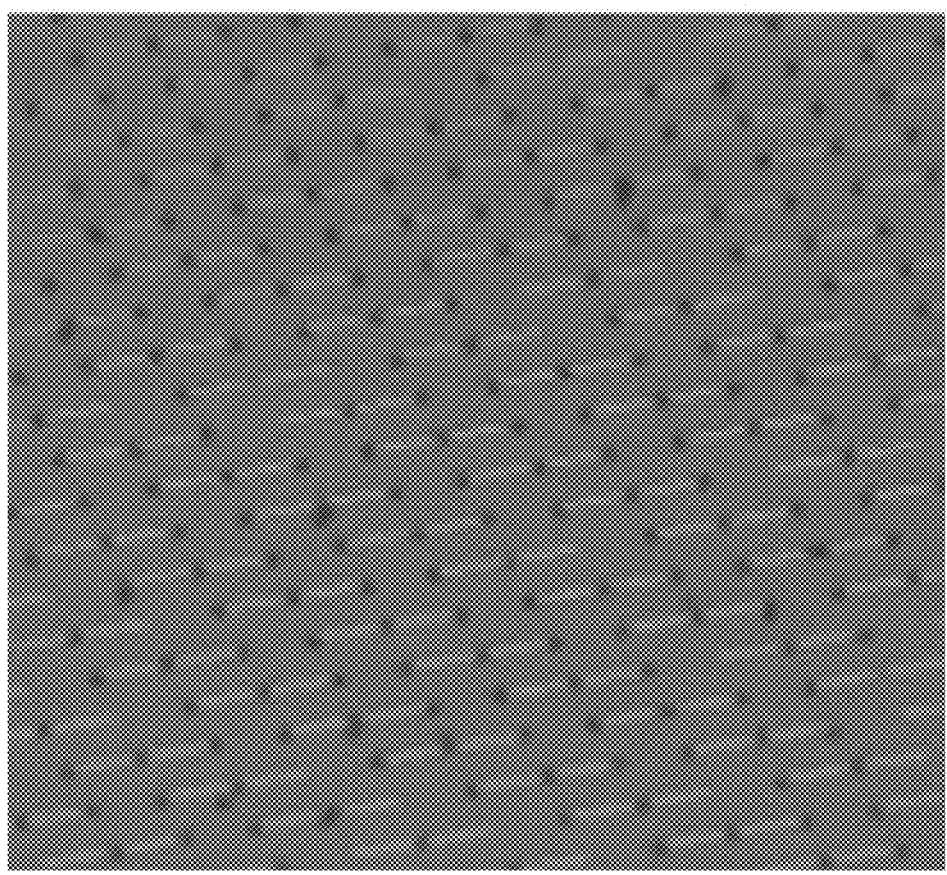
FIG. 2 shows a magnetic and virtual confinement array.

FIG. 2 is a photomicrograph of a combined virtual well and magnetic array according to various embodiments as described herein. Most positions in said array have a single bead in the position between the magnets at the point wherein the virtual well structure is located. Some locations have more than a single bead. Most of the ends of the magnets also have beads located thereupon.

Various different molecular biology applications utilizing said "chamber free" array or "virtual" wells are envisioned. Said array may be used as a tool, for example, as a cell sorter, and subsequently said array may additionally perform molecular biology on said cells, which may include sorting, measurement or manipulation for one or more biochemical events or reactions of interest (e.g. drug screening, or biomolecular detection) may be done. Said virtual well array may be used for cell monitoring and analysis, for example, the system may measure the electrical signature of a cell wherein said cell is captured in said array and or adjacent to sensing elements associated with said virtual well. Said array may be used for screening of rare cells, for example, for detection of reactions in drug screening for drug development, or for selection and testing of cancerous cells.

Figure 3:
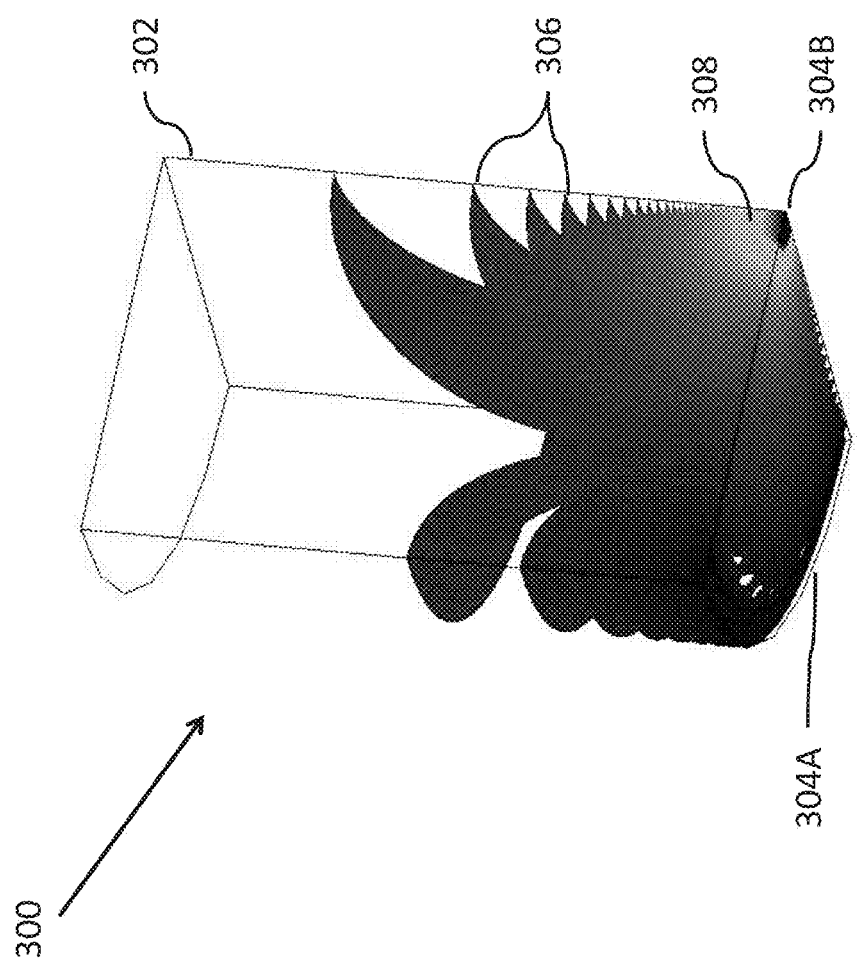
FIG. 3 shows a Comsol simulation the electric fields for a virtual well.

FIG. 3 is a graphical representation resulting from a Comsol simulation, depicting the 3D equipotential field strength curves 306, of one fourth of a cylindrical structure 300 that result from a field being applied to the electrodes 304A and 304B. As a result of the substantial radial asymmetry of the field, the volume wherein the field gradient is most concentrated 308 near the center electrode 304 B, which is the point wherein a bead may be held by a magnetic array as shown in FIG. 2.

Other Electrical Concentration Uses

In other embodiments, the virtual well(s) may be utilized for and or combined with multiple steps in a biomolecular process, for example, bead enrichment of particle(s) moving in an electric field, microfluidic sample-prep and library prep such as on-chip extraction of DNA, shearing of DNA, on-chip normalization of DNA concentration, emulsion-free amplification, sensing, which may include sensing utilizing dual-sensing or multi-sensing sequencing detectors, which may utilize transient and or steady state electronic sequencing and rephasing methods for extending the length of read of a sequencing process, wherein said multiple steps may result in a fully integrated electronic genomic analyzer system.

In some embodiments, multiple arrays of virtual wells may be utilized, wherein said different arrays of virtual wells may be utilized for different biological reactions, processes or methods. In some embodiments, one array or set of arrays may be utilized for extraction of DNA, wherein different arrays in said set of arrays or different members within a set may retain cells from different samples, or may retain different types of cells from a single sample, or a combination thereof. For example, different samples may be held in different arrays, and different types of cancer cells from a single sample tumor may be retained within different areas of a single array. The different cell types may be sorted a segregated, or the cell type may be determined as a result data derived from the individual cells after said cells are captured and retained in individual locations on said array of virtual nanoreactor.

In some embodiments, several biological reactions, processes or methods may be performed on a single sample or moiety while it is retained in position within a virtual well. In other embodiments, one or more biological reactions, processes or methods may be performed on a sample(s) or moiety(s) in a position(s) in a virtual well array(s) prior to the transfer or movement of said sample(s) or moiety(s) to another position(s) in another virtual well array(s).

In some embodiments, the array of electrical concentration and confinement virtual wells may be used for purposes other than the capture/isolation of nucleic acids as otherwise described herein for sequencing and amplification of said nucleic acids. In some embodiments, the electrical concentration and confinement may be used with any charged moiety, wherein the time period, moiety concentration, mobility, concentration, local viscosity, cross-linking percentage of local polymers, or concentration of the charged moiety(s) may influence the spacing of electrical confinement structures, and or field strength utilized, and or magnitude of field gradient in order to maintain sufficient confinement within individual virtual wells. The level of cross contamination between different virtual wells which may be tolerated may vary for different applications, and at different steps in a biological reaction, process or method. For example, if a nucleic acid amplification reaction process was performed on different samples in adjacent virtual wells, cross contamination may be problematic during early thermal cycles of a PCR reaction, while cross contamination during later cycles of a PCR reaction may not be particular concern, as primers may be largely consumed, preventing significant amplification of the cross contaminating nucleotides from other virtual wells.

In some embodiments, a polymer may be utilized to reduce the migration rate of nucleotides or other moieties; said polymer may be a partially entangled polymer such as POP-6™, PEG, PMMA or an agarose, polyacrylamide, or starch gel. The concentration and or percentage of cross linking may be varied as needed for various mobilities of different moieties for which confinement in said virtual well is desired. Said polymer may be introduced to the volume of the virtual well before the introduction of sample moieties or other moieties used in said biological reaction, process, or method to said virtual well, or may be introduced into said volume of said virtual well with said sample moieties or other moieties used in said biological reaction, process, or method, or may be introduced into said volume of said virtual well after the introduction of said sample moieties or other moieties used in said biological reaction, process or method into said volume of said virtual well.

In some embodiments assays or detection targets include cell biology, drug screening and monitoring for specific cell types, detection of DNA, RNA (nucleic acids), proteins, charged small molecules, ligands, or other biomolecules.

In some embodiments, the electrical concentration and confinement may be utilized to capture moieties to which other biomolecules or biological moieties have been bound, for example beads with charge to which antibodies may be bound, and wherein said beads may be subsequently used to capture proteins, and wherein said beads further may be subsequently captured utilizing said electrical concentration and confinement array.

In some embodiments, the virtual wells may be used for several different applications in addition to sequencing, for example said virtual wells may be utilized as a hybridization array (similar to an Affymetrix or Agilent DNA micro array) wherein the DNA is on beads, and said beads may be held in place by the virtual well. In other embodiments, the virtual nonreactors may be utilized for digital PCR, wherein said beads may be introduced into the array; detection may be done with an electronic sensor array associated with each element of said array, or detection may utilize optical means, to detect the presence or quantity of a particular nucleic acid. Digital PCR may be utilized to quantitate the concentration of targets within a sample in a relativistic manner.

In some embodiments concentration of sample into the virtual wells as described herein may allow quantitation with greater sensitivity. In some embodiments, utilizing concentration in some areas of the array and not in others may allow for a greater concentration quantitation dynamic range. In further embodiments, DC concentration fields may be inverted so as to partly "push" sample moieties away from said virtual wells. In some embodiments, combinations of concentration, no concentration, and pushing away of sample moieties ion different areas of said array of virtual wells may be utilized to further extend the dynamic range of said digital PCR, or of any other desired biological reaction, process, or method. Beads with different primers may introduced into different areas of the virtual well array as described herein, allowing simultaneous digital PCR reactions for several targets.

In some embodiments pulsed field gel electrophoresis may be utilized, wherein a non sinusoidal AC waveform may be used wherein a higher positive voltage may be balanced by a longer but shorter negative voltage such that the average voltage is substantially zero. The higher positive voltage may be utilized with a polymer concentration could be such that repetition of the DNA occurs in the polymer solution. Said polymer solution may effectively cause a lower migration of DNA the direction of the lower field compared to the migration in the higher strength electric field which may thereby increase the mobility of said DNA. In this manner the DNA may migrate more in the desired direction while other molecules such as Mg may move freely back and forth due to the balanced nature of the AC waveform. Said migrational variance may also be frequency dependant, so that different sizes of DNA may be captured. Said pulsed field gel electrophoresis may be 1D or 2D, and may utilize contour clamped electric field, transverse alternating field electrophoresis, or rotating gel electrophoresis, any of which may be utilized with either a gel, an entangled polymer, or another sieving matrix.

In some embodiments, the virtual wells may be utilized for full extension reactions of DNA bound to primers bound to said bead. In a further embodiment, said virtual well may be used for ligation reaction detection.

In some embodiments, said system may use electromagnets, permanent magnets, or electrodes or other different subsystems to generate electromagnetic fields for transient or part-time isolation, or holding or concentration of the biomolecules or other moieties of interest (e.g. DNA, cells, proteins) or the carrier of the biomolecule or other moiety of interest (e.g. beads, particles, or other moieties). Said electromagnetic fields may be magnetic fields, electric fields, or a combination of the two. Said electric fields may be DC fields, AC fields, pulsed DC fields, non-sinusoidal AC fields, pulsed AC fields, or a combination thereof. The nanoreactors with virtual walls (or fences) may be used or created with electric or magnetic fields to hold, capture, concentrate, isolate, or manipulate the biomolecules or its carrier.

In some embodiments, wherein two or more sets of electrode structures may be utilized, virtual walls or isolation walls or fences may be turned on or off, or modified as to the magnitude, shape or period of the electromagnetic field at a desired time, which may be a fixed time, or may be in response to a change from a sensor associated with a specific member of said array of electrode structures, wherein said turning on or off, or modifying as to the magnitude, shape or period of the electromagnetic field may be utilized for controlling the manipulation, and movement of the particles, beads, cells, biomolecules or other moieties of interest which are concentrated, confined, or isolated in said array of electrode structures, as well as the biomolecules or other moieties of interest which may be used as in a reaction, such as an antigen or secondary antibody in protein detection, or nucleotides in DNA or RNA sequencing, or secondary cell in cellular interactions, or drugs or cells in drug screening and monitoring. This feature may be used to provide easy access and flexible manipulation, and or mixing.

Normalization

In some embodiments, the virtual well array may be used for normalization of the amount and or concentration of DNA, other biomolecules, other charged moieties, or the carriers of DNA, other biomolecules or other moieties input into the system, and may generate a feedback and or control to the entry, which may be utilized to control the amount and or the concentration of said DNA, other biomolecules other charged moieties, or the carriers of DNA, other biomolecules or other moieties input into the system as described herein. Said system may be further utilized for the purpose of real-time normalization of the detection or sequencing array.

B-Cells on Beads

In some embodiments, the electrical concentration and confinement array may be utilized to capture charged beads to which other B-cells have been bound, for example magnetic beads to which proteins, polysaccharides, or other immunogens may be bound, and wherein said charged beads may be subsequently used to capture said B-cells, and wherein said charged beads further may be subsequently captured utilizing said electrical concentration and confinement array.

Carbohydrates or Gycolipids on Beads

In some embodiments, the electrical concentration and confinement array may be utilized to capture charged beads to which other carbohydrates or glycolipids have been bound, for example charged beads to which proteins or peptides which comprise carbohydrate binding modules may be bound, and wherein said charged beads may be subsequently used to capture carbohydrates or glycolipids, and wherein said charged beads further may be subsequently captured utilizing said electrical concentration and confinement array. Such a carbohydrate or glycolipid binding moiety may comprise a carbohydrate active enzyme, such as a glycosidic hydrolase, a lectin, a galectin, a intelectin, a pentraxin, a selectin, an adhesion, or a hyaluronan.

Drug Screening

In some embodiments, said array may be used for chemical screening applications and non-biomolecules can be tested or monitored or measured with the system.

For example, in use for drug screening, wherein measurement of the effect of a drug is desired, the system may utilize, for example, 100, 1000, 10,000, or 1,000,000 different drug candidates each on their own beads, wherein said beads may be captured and hold in the "virtual well" array, and wherein the system may subsequently allow interactions and measurements of said interactions between said beads and a cell or set of cells of interest, wherein the electrical confinement can be used for isolation of the pixels in the array, providing a high throughput and fast drug screening system.

In some embodiments, the electrical concentration and confinement array may be utilized to capture a combined set of charged beads to which multiple different types of biomolecules have been bound, wherein said combined set of charged beads may comprise multiple sets of charged beads, wherein said multiple different types of biomolecules or biological moieties have been bound, wherein there may be one type of binding moiety which may bind one biomolecules or biological moiety on a set of charged beads, and a different type of binding moiety which may bind a different biomolecules or biological moiety on a different set of beads. Said combined set of charged beads may also comprise sets of charged beads wherein the set of charged beads may comprise charged beads to which multiple binding moieties are bound.

In further embodiments, said combined sets of beads may further comprise a label, wherein said label may be utilized to differentiate between different sets of beads. Said label may be an optical label, such as a fluorescent dye, a biochemical label such as DNA, metal particle labels, any other type of label, or a combination of different types of labels. Said labels may be utilized to determine which type of bead may be at each element of the array electrical concentration and confinement features.

In some embodiments, different methods of detection of said beads and the interactions that result from various biomolecular reactions may be observed as a result of the detection of said beads. Said detection may effectualized as a result of a NanoNeedle sensor, a NanoBridge sensor, a ChemFET sensor, an ISFET detector, an optical sensor, such as for example a fluorescence detector, a SERS detector, an absorption detector, a PH detector, a conductance detector, a mass resonance detector, a calorimeter detector, or any other type of detector suitable for detection of biomolecular reactions, or of other types of reactions, wherein moieties bound to said beads may not be biomolecules or biomolecular moieties, and or the moieties with which said moieties bound to said beads may not be biomolecules or biomolecular moieties. In some embodiments, said sensors may be combined at each position in the array with an electrical concentration and confinement feature.

In some embodiments, the electrical concentration and confinement may be utilized to directly capture charged moieties and wherein said charged moieties may be bound to other biomolecules or biological moieties. For example antibodies or antibodies bound to proteins may be concentrated or confined and wherein said antibodies or antibodies bound to proteins may be subsequently used to capture proteins or additional antibodies.

B-Cell Direct Capture

In some embodiments, the electrical concentration and confinement array may be utilized to capture other B-cells, for example B-cells to which proteins, polysaccharides, or other immunogens may be bound, and wherein said B-cells may be subsequently used to capture said proteins, polysaccharides, or other immunogens, and wherein said charged B-cells further may be subsequently captured utilizing said electrical concentration and confinement array.

Carbohydrates and Glycolipids Direct Capture

In some embodiments, the electrical concentration and confinement array may be utilized to capture carbohydrates or glycolipids, for example carbohydrates or glycolipids to which proteins or peptides which comprise carbohydrate binding modules may be bound, and wherein said carbohydrates or glycolipids may be subsequently used to capture carbohydrates or glycolipids, and wherein said charged beads further may be subsequently captured utilizing said electrical concentration and confinement array. Such a carbohydrate or glycolipid binding moiety may comprise a carbohydrate active enzyme, such as a glycosidic hydrolase, a lectin, a galectin, a intelectin, a pentraxin, a selectin, an adhesion, or a hyaluronan.

Multiple Moiety Capture

In some embodiments, the electrical concentration and confinement array may be utilized to capture a combined set of charged moieties to which multiple different types of biomolecules have been bound, wherein said combined set of charged beads may comprise multiple sets of charged moieties, wherein said multiple different types moieties may have multiple binding sites, wherein there may be one type of binding region which may bind one biomolecules or biological moiety on a set of charged moieties, and a different type of binding moiety which may bind a different biomolecule or biological moiety on a different set of binding sites. Said combined set of charged beads may also comprise sets of charged beads wherein the set of charged beads may comprise multiple binding moieties which may be bound to multiple other moieties.

In further embodiments, said combined sets of charged moieties may further comprise a label, wherein said label may be utilized to differentiate between different sets of charged moieties. Said label may be an optical label, such as a fluorescent dye, a biochemical label such as DNA, metal particle labels, any other type of label, or a combination of different types of labels. Said labels may be utilized to determine which type of moiety may be at each element of the array of magnetic array features.

In some embodiments, different methods of detection of said charged moieties and the interactions that result from various biomolecular reactions may be observed as a result of the detection of said charged moieties. Said detection may effectualized as a result of a NanoNeedle sensor, a NanoBridge sensor, a ChemFET sensor, an ISFET detector, an optical sensor, such as for example a fluorescence detector, a SERS detector, an absorption detector, a PH detector, a conductance detector, a mass resonance detector, a calorimeter detector, or any other type of detector suitable for detection of biomolecular reactions, or of other types of reactions, wherein moieties bound to said charged moieties may not be biomolecules or biomolecular moieties, and or the charged moieties with which said moieties bound to said charged moieties may not be biomolecules or biomolecular moieties.

In some embodiments, the "virtual well" array may increase the reaction rate by concentrating biomolecules of interest, such as DNA, RNA, or other moieties can for more efficient synthesis, as said virtual well may increase the concentration of the molecules, especially the concentration of shorter length DNAs or molecules through a synthesis process.

Valve System

Thus in one embodiment of the current invention it may be desirable to integrate a valving device with the flow cell. Such a valving configuration may include various inputs, which may include inputs for the four dNTPs, which may also contain buffer, salts, enzyme and any other moieties required for incorporation of nucleotides, various buffers and wash reagents, polymerase containing buffers, which may also contain salts and any other moieties needed for polymerization, reagents needed to strip any coatings from the flow cell, reagents which may be needed to re-coat the flow cell, buffers which also include a phosphatase, or other reagents.

In one embodiment of the current invention, the valving device may be fabricated of PDMS. In another embodiment the valving device may be fabricated from glass with magnetically or pneumatically activated elastomeric valves.

PDMS Valve

In some embodiments of the current invention, it may be desirable to bond said valving and fluidics PDMS manifold to a silicon device. It may be desirable to increase the bonding strength between said PDMS and said silicon device.

In one embodiment of the current invention, it may be desirable to utilize plasma activated PDMS to improve the bond strength. As a plasma treatment which has too much power or too much pressure may actually decrease the bond strength of PDMS to silicon, it may be important to utilize lower power levels and pressures. Tang et al describe appropriate power and pressure levels in 2006 J. Phys.: Conf. Ser. 34 155. In one embodiment it may be appropriate to utilize a pressure between 500 militorr and 30 militorr and a power level between 10 and 60 watts while utilizing, for example, a 790 series Plasma-Therm.

Purging Valve System

One embodiment of the current invention permits purging of air or other contaminants in each input line up to each input port control valve; so that when each input port is activated, appropriate reagents may be introduced to the system. For example, to clear the dATP line, the dATP control line, and the Waste one Upper Control line may be activated, causing air and any unwanted reagents in the dATP lines to flow through the dATP valve and out Waste one. In other embodiments, the dCTP, dTTP, and the dGTP lines may be purged or cleared of contaminants by activating the dCTP control line and the Waste one Upper Control lines, the dTTP and the Waste one Upper Control lines, and the dGTP control lines and the Waste one Lower Control line respectively. To purge or remove contaminants from the sample line, the Sample Control line and the Waste two Control lines may be activated.

Purging and removing contaminants from all lines may be needed after replacing a sequencing assembly. Similarly purging or removing contaminants from reagent lines may be needed after replacing or refilling reagent bottles or containers. A further need for purging or removing of contaminants may result from periods of time wherein the instrument is not used, which may permit any reagent lines containing reagents which need to be cooled below ambient to suffer degradation; for example, polymerase in a polymerase containing reagent may suffer from extended exposure to ambient temperatures.

In some embodiments of the current invention, it may be desirable to fill the manifold leading to the input of the flow cell, so that any reagents remaining from a previous use of the manifold may be removed. For example, prior to introduction of dATP into the flow cell, the dATP control line, the Upper Liquid Control line, and the Waste two Control line may be activated. dATP reagent will then commence to flow from the dATP input line, around both sides of the upper liquid loop, through the channel between the upper liquid region and the lower liquid region, and out through the waste two valve into the waste two line. Alternatively, prior to introduction of dCTP into the flow cell, the dCTP control line, the Upper Liquid Control line, and the Waste two Control line may be activated. dCTP reagent will then commence to flow from the dCTP input line, around both sides of the upper liquid loop, through the channel between the upper liquid region and the lower liquid region, and out through the waste two valve into the waste two line. Similarly, prior to introduction of dTTP into the flow cell, the dTTP control line, the Lower Liquid Control line, and the Waste two Control line may be activated. dTTP reagent will then commence to flow from the dTTP input line, around both sides of the lower liquid loop, through the channel between the lower liquid region and the lower liquid region, and out through the waste two valve into the waste two line. Similarly, prior to introduction of dGTP into the flow cell, the dGTP control line, the Lower Liquid Control line, and the Waste two Control line may be activated. dGTP reagent will then commence to flow from the dGTP input line, around both sides of the lower liquid loop, through the channel between the lower liquid region and the lower liquid region, and out through the waste two valve into the waste two line.

Buffer one can be made to flow through the main flow cell (in dark blue), and out the Waste three port by activating the B1C control line, and the W3C control line. Alternatively, Buffer one can be made to flow out the Waste two port by activating the B1C control line, and the W2C control line. In another alternative use, Buffer one can be made to flow out the Waste one line through the upper section of the liquid manifold by activating the Buffer one control line, the Upper Liquid Control line, and the Waste one Upper Control line. Similarly, the lower liquid manifold can be flushed with Buffer one by activating the Buffer one control line, the Lower Liquid Control line, and the Waste one Lower Control line. Activating flow in a combination of these areas either in a time sequence or activated together enables clearing the entire liquid manifold to be purged of bubbles, other contaminants, or as a wash or purge of any other liquids which may have been introduced to the system via the dATP, dTTP, dCTP, dGTP, Buffer two, or Sample input ports.

Surface Passivation

In some embodiments of the current invention, it may be desirable to utilize a passivation layer over the silicon device which has a higher bond strength than thermally grown silicon dioxide. Tang et al describe several passivation layers which provide improved bonding strength, including PSG (PECVD phosphosilicate glass), USG (PECVD undoped silicate glass), $Si_3N_4$ (LPCVD silicon nitride).

Minimizing Dead Volume

For a device fabricated of PDMS or other similar materials, it is possible to utilized pressure valves to control the flow of reagents. With such valves it is possible to have the several valves in close proximity to each other, and the valves may be very close to a central channel, reducing dead volume, as shown in FIG. 4 which shows a reagent valve system 400 with three reagent input lines 402 with valves 406, each of which can be configured to flow towards the input to the flow cell 408, under the control of pressure control lines 404.

Figure 4:
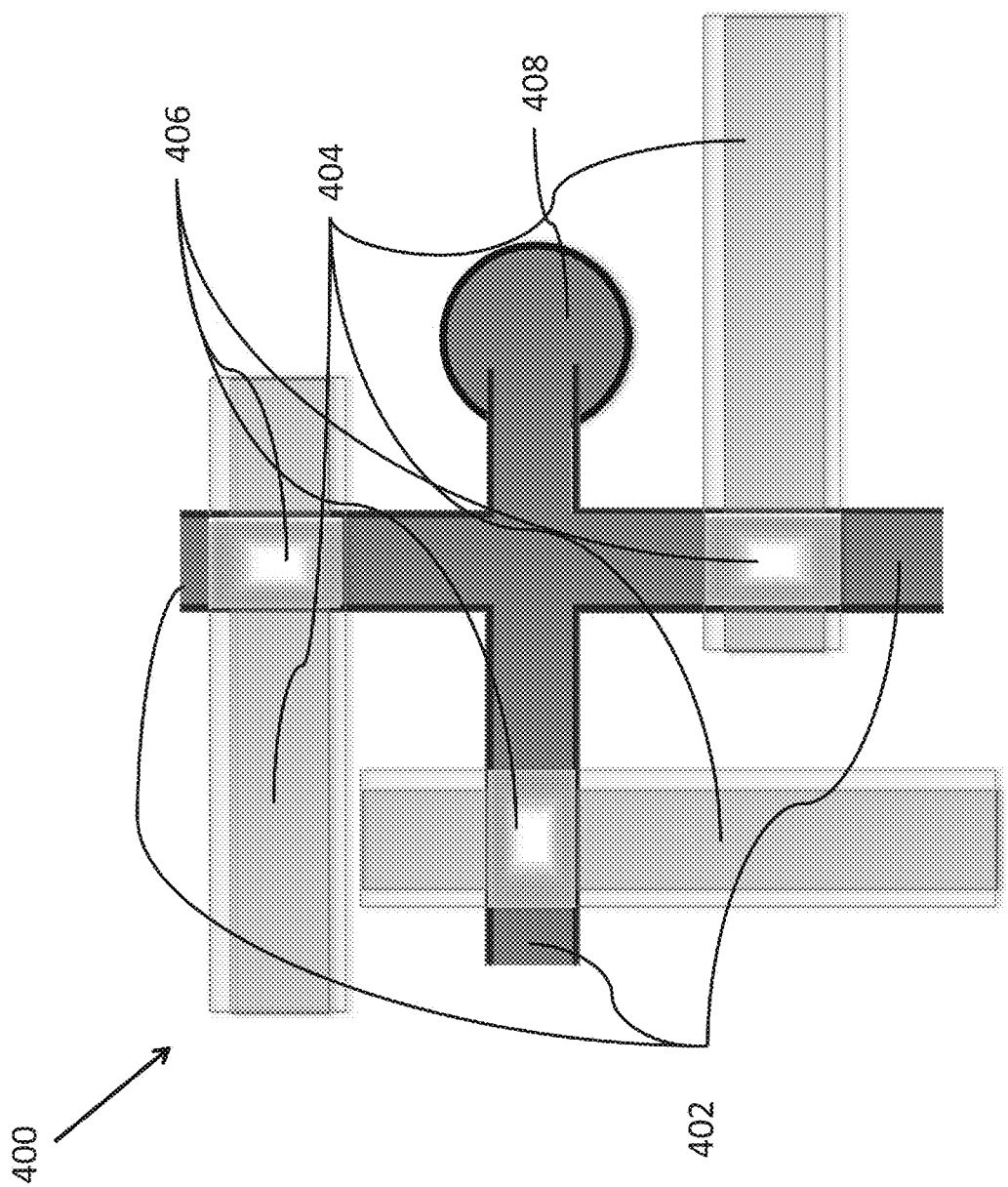
FIG. 4 shows a schematic of a PDMS valving subsystem.
Figure 5:
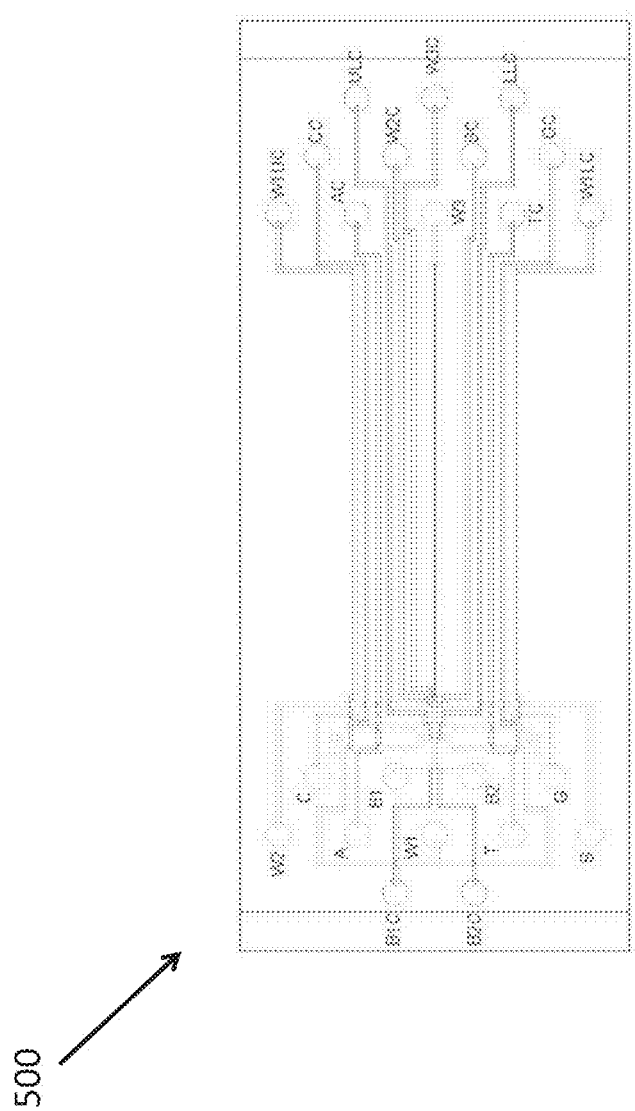
FIG. 5 shows a drawing of a PDMS valving subsystem.
Figure 7:
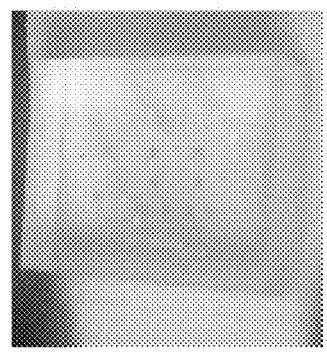
FIG. 7 shows a fabricated PDMS valving subsystem.
Figure 6:
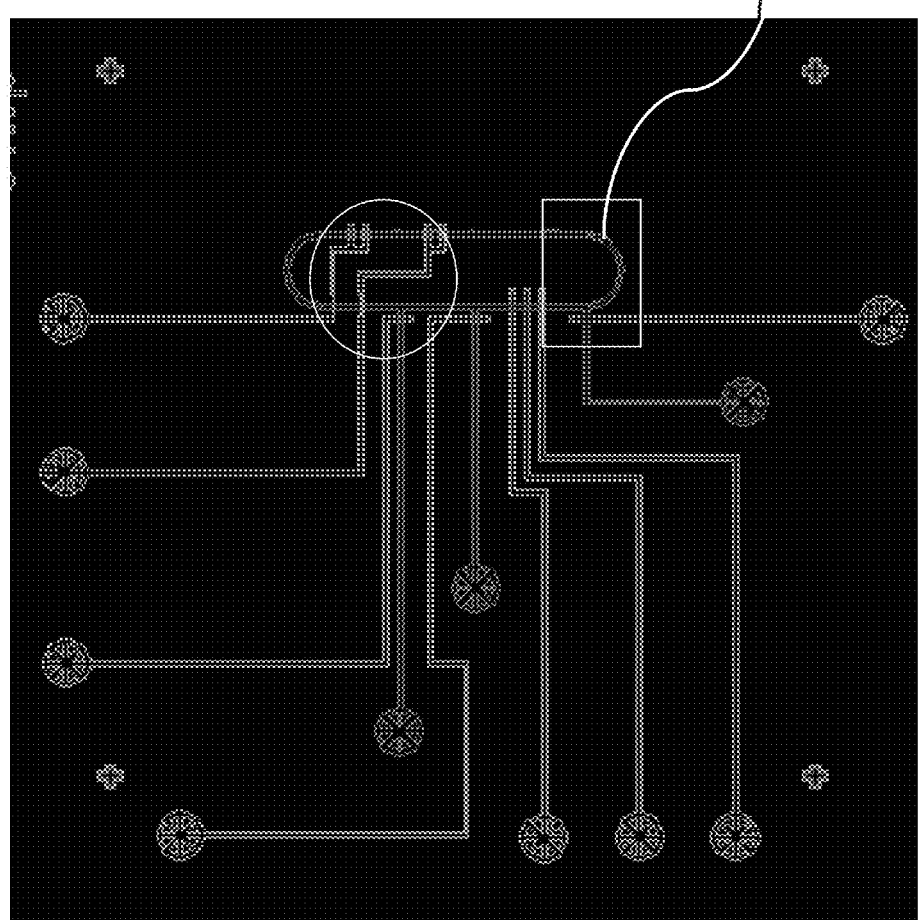
FIG. 6 shows a drawing of a fabricated PDMS valving subsystem.

For a more complex system, where more reagent inputs are desired, the simple valve system 400 of FIG. 4 is insufficient, as it has but three reagent inputs lines 402. In an alternative embodiment as shown in FIGS. 5 and 6, many more inputs are enabled. This approach also permits clearing the dead volume of the channel. In FIG. 5, inputs include input ports for dATP, dTTP, dCTP, dGTP, Buffer one, Buffer two, and Sample, output ports Waste one, Waste two, and Waste three. Control lines are in place for each input and output port, with additional control lines to control the direction of flow between activated ports. A waste port is shown immediately prior to the flow cell, so that any remnant reagent from a previous flow may be removed, allowing a very clean transition from one reagent to another, without diffusion from any dead volumes in the valving system. FIG. 6 depicts a valving system with a oval flow path, such that all input valve port positions have a path to an outlet (waste) port in both directions from said input valve port position. Valves as shown in FIG. 4 may be utilized for each valve shown in FIGS. 5, 6 or in a physical embodiment of a reagent valving system 700 as shown in FIG. 7, wherein a photograph of a PDMS valve system 500 is shown.

Interface to Valve System

In some systems which utilize PDMS valving manifolds, pins or needles inserted into the PDMS are utilized to connect reagent lines to the valving manifold. While this provides for secure attachment, attaching a number of reagent lines to a PDMS valving manifold is time consuming and error prone. Thus in some embodiments of the current invention, it may be desirable to utilize an interface manifold, wherein the reagent lines are connected to the interface manifold, rather than to the valving manifold, and the interface manifold may be connected to the valving manifold. The reagent lines may be attached to pins or needles, which may be attached to the interface manifold. The pins or needles may be permanently affixed to the interface manifold, being held in place with an adhesive, by welding or brazing, by utilization of a press fit, or by some other means. Alternatively, the lines may be directly connected to the interface manifold, wherein they may be retained by a fitting or o-ring, or by some other means as known in the art.

In some embodiments of the current invention the interface manifold may sealingly interface to the valving manifold such that reagents may flow from the interface block to the valving manifold. The interface between the interface manifold and the valving manifold may be an interface which is utilized by a user to enable replacement of the chip/flow cell and/or valving manifold.

In some embodiments of the current invention the interface manifold may have internal channels formed by bonding; such bonding could include fusion bonding, solvent bonding or adhesive bonding.

In some embodiments, minimizing the path length, otherwise reducing the fluidic volume between the valves and the active part of the flow cell may be important for several reasons, including minimizing the amount of mixing of reagents, which occurs as a result of differences in flow rates at the center of a channel versus the flow rate at the edges of a channel, due to wall interactions, as well as diffusion. In some embodiments it may also be desirable to minimize the volume which is not temperature controlled, in order to prevent degradation of reagents, such as polymerase, in volumes which are not temperature controlled. In some embodiments it may be desirable to minimize plumbing volume to concomitantly minimize cross contamination of reagents may also occur in regions of flow which are common to multiple reagents, due to nonspecific binding to materials which contact said reagents.

In some embodiments, it may be desirable to integrate a valving system as part of a flow cell. Said valving system may be utilized to enable the flow of samples to sections of a flow cell, such that different samples may be utilized for said different sections of said flow cell. In other embodiments said valving system may be integrated adjacent to said flow cell, whereby said valving system and said flow cell may sealing interface to each other. In other embodiments, said valving system and said flow cell may be adjacent to each other on a single mount, wherein both said valving system and said flow cell may be mounted to said mount. Said valving system may also comprise a waste valve(s) such that fluids may be removed from said valving system prior to flowing into said sections of said flow cell. For example if there is a significant dead volume in said valving system, it may be desirable to remove fluid which may have an unacceptable level of cross contamination from a previous fluid.

Magnetic Array

Magnetic Array and the Size Thereof

FIG. 8 illustrates a schematic representation of one embodiment of the current invention, where a magnetic or paramagnetic bead may be held in place over a sensing region and or virtual well by a magnetic array. Retained magnetic or paramagnetic beads may have monoclonal populations of DNA. Said beads may be sized such that there is sufficient room for only one bead over each sensor, thus providing for a one to one correspondence between sensors and beads. Although there may be room for only one bead over each sensor, there can be room between beads when the beads are aligned over the beads, resulting in reduced cross-talk between sensors. For example, a set of beads may be 10 microns in diameter located over sensors which are 8 microns across, and the sensors may be spaced 15 microns apart, resulting in a 5 micron space between the beads. The size of the sensors may be larger than the beads, if there is insufficient room for two beads to be retained above the sensor. The size of the beads, sensors, and spacing can vary. In other embodiments, beads may be greater in size than 10 microns, such as 15 microns, 20 microns, 25 microns, or larger. In further embodiments the beads may be smaller than 10 microns, such as 5 microns, 3 microns, 2 microns, 1 micron, or less than one micron. The sensors may be sized to align with the size of the beads, and thus may be larger, or smaller in size than 8 microns across, potentially ranging from less than one micron, to 1, 2, 3, 5, 10, 15, 20 or more microns across. The spacing between the sensors may also be greater than 15 microns, or may be less than 15 microns; the sensor spacing may range from less than one micron, to 1, 2, 3, 5, 10, 15, 20, 25 or more microns between sensors.

FIG. 8 depicts a single element 800 in an array of NanoNeedles and magnets 816, wherein a substrate 804 may have an electrode 806 on said substrate 804 and under a bead 802, or on a spacing or adhesion layer (not shown) betwixt said electrode 806 and said substrate. Said electrode 802 may thus be within the Debye layer of the bead. A dielectric layer 808 with may be placed above said substrate 804, and may also cover part of said electrode 806, and may further have a recess or cutout which may be larger than the space needed for said bead 802 when said bead 802 is retained in place. Said dielectric may serve multiple functions, including, providing a surface against which the magnetic force may pull the surface of said bead 802. The magnetic force resulting from the interaction of magnets 816 and said bead 802, serve to retain and position said bead 802, with a force exerted downward against said electrode 802 and against dielectric 808. A second layer of dielectric 812 may be applied to said dielectric 808, providing significant reagent access to said bead 802, while further extending the height of the total thickness of dielectric material, such that an upper electrode 814 may be fabricated on said second layer of dielectric 812. Said upper electrode 814, dielectric, and second dielectric 812, may be positioned such that said upper electrode may be within the Debye length of said bead, and may further be close to the midpoint of said bead 802. Said upper electrode 814 may be above the center line of said bead 802, particularly if said upper electrode 814 is within the Debye length of said bead 802, or may be below the centerline of said bead 802, such that the top of said upper electrode 814 is in contact with said bead 802 or within the Debye length of said bead 802, at an angle of between 10 and 90 degrees from the perpendicular of the point of contact between said bead 802 or within the Debye length of said bead 802, and said electrode 806. Said angle from the perpendicular to the point of contact between said bead 802 or within the Debye length of said bead, and the top of said upper electrode may be between 30 and 85 degrees, between 45 and 80, or between 60 and 75 degrees. Other methods of positioning said electrodes is anticipated such that the aforementioned angular displacement or separation with respect to the perpendicular of the point of contact with said bead 802 with electrode 806 and upper electrode 814 with respect to the center of said bead 802 is maintained. Said electrodes could for example both be placed on a side wall or may both be placed upon a dielectric, such that both electrodes are within the Debye length of said bead 802 and are placed such that the aforementioned angular displacement or separation between said electrodes is maintained. Said magnets 816 may be recessed into said substrate 804, be upon said substrate 804, or upon dielectric 808, but should be below the centerline of said bead 802, such that a downward force is applied to said bead 802, such that said bead 802 is pulled down towards said electrode 806. Said magnets 816 should further be placed offset with respect to the center of the bead 802 when said bead is in place in the array, such that said bead 802 is pulled towards said upper electrode such that said bead 802 is brought to within a Debye length of said bead 802 to said upper electrode 814. Each of the elements of single element 800 in an array of NanoNeedles and magnets 816 may have additional spacer layers or adhesion layers between said elements. Said Debye length may include Debye lengths which may result from high concentrations of salt, from low concentrations of salt, from deionized water, or from aqueous solutions which are comingled with nonaqueous fluids which are miscible in water.

Improved Flow with Magnetic Array

A chamber-free magnetic retention structure as shown in FIG. 1 may permit improved flow of nucleotides, polymerase and other components, as their flow is not hindered by a well structure permitting better washing, more complete incorporation of bases, and faster cycle times then would be possible if the bead were in a well. In a well structure, a bead and associated DNA such hinders accessibility and flow, so that a higher concentration of polymerase and nucleotides may be needed to permit sufficient diffusion to all parts of a bead. Said higher concentrations of dNTPs and polymerase may increase the error rate due to misincorporation by said polymerase, resulting in higher levels of leading sequencing phase error then might occur with a chamber-free structure.

Array Re-Use

The cost of sequencing has a number of parts; for sequencing using electronic sensors, one of the major costs is the cost of the processed silicon itself; that is: the sensor. This may be particularly true if the sensor is not re-useable, but must be discarded after a single use. The magnetic array described above makes reuse fairly straightforward, as the DNA is not bound to the sensor, and the beads can be easily removed be reducing or removing the magnetic field which holds said beads in place. If the beads are instead held in place with a structure, removal may be more difficult.

In one embodiment of the current invention, beads which are held in place by a structure, or array of wells, may be removed by applying a magnetic field such that said beads, which may be magnetic or paramagnetic beads may be pulled out of the wells, and subsequently removed from the flow cell by flowing a reagent through said flow cell.

Other Magnetic Array Uses

In some embodiments, the array of magnetic features may be used for purposes other than the capture/isolation of nucleic acids as otherwise described herein for sequencing and amplification of said nucleic acids.

In some embodiments, the magnetic array may be utilized to capture magnetic beads to which other biomolecules or biological moieties have been bound, for example magnetic beads to which antibodies may be bound, and wherein said magnetic beads may be subsequently used to capture proteins, and wherein said magnetic beads further may be subsequently captured utilizing said magnetic array.

In some embodiments, the magnetic array may be utilized to capture magnetic beads to which B-cells or other types of cells, for example different types of cancer cells, have been bound, for example magnetic beads to which proteins, polysaccharides, or other immunogens may be bound, and wherein said magnetic beads may be subsequently used to capture said B-cells or other types of cells, and wherein said magnetic beads further may be subsequently captured utilizing said magnetic array.

In some embodiments, the magnetic array may be utilized to capture magnetic beads to which other carbohydrates or glycolipids have been bound, for example magnetic beads to which proteins or peptides which comprise carbohydrate binding modules may be bound, and wherein said magnetic beads may be subsequently used to capture carbohydrates or glycolipids, and wherein said magnetic beads further may be subsequently captured utilizing said magnetic array. Such a carbohydrate or glycolipid binding moiety may comprise a carbohydrate active enzyme, such as a glycosidic hydrolase, a lectin, a galectin, a intelectin, a pentraxin, a selectin, an adhesion, or a hyaluronan.

In some embodiments, the magnetic array may be utilized to capture a combined set of magnetic beads to which multiple different types of biomolecules have been bound, wherein said combined set of magnetic beads may comprise multiple sets of beads, wherein said multiple different types of biomolecules or biological moieties have been bound, wherein there may be one type of binding moiety which may bind one biomolecules or biological moiety on a set of beads, and a different type of binding moiety which may bind a different biomolecules or biological moiety on a different set of beads. Said combined set of beads may also comprise sets of beads wherein the set of beads may comprise beads to which multiple binding moieties are bound.

In further embodiments, said combined sets of beads may further comprise a label, wherein said label may be utilized to differentiate between different sets of beads. Said label may be an optical label, such as a fluorescent dye, a biochemical label such as DNA, metal particle labels, any other type of label, or a combination of different types of labels. Said labels may be utilized to determine which type of bead may be at each element of the array of magnetic array features.

In some embodiments, different methods of detection of said beads and the interactions that result from various biomolecular reactions may be observed as a result of the detection of said beads. Said detection may be effectualized as a result of a NanoNeedle sensor, a NanoBridge sensor, a ChemFET sensor, an ISFET detector, an optical sensor, such as for example a fluorescence detector, a SERS detector, an absorption detector, a PH detector, a conductance detector, a mass resonance detector, a calorimeter detector, or any other type of detector suitable for detection of biomolecular reactions, or of other types of reactions, wherein moieties bound to said beads may not be biomolecules or biomolecular moieties, and or the moieties with which said moieties bound to said beads may not be biomolecules or biomolecular moieties. In some embodiments, said sensors may be combined at each position in the array with magnetic features.

In some embodiments, magnetic arrays may be utilized wherein some positions of said array may be occupied with retained beads which are bound to captured cells, wherein said cells may be of a particular type of cell, and other positions of said magnetic array may be occupied with other type(s) of retained beads wherein different types of cells may be bound to said other type(s) of retained beads with different cell capture moieties.

In some embodiments, said retained beads which may comprise several types of retained beads may then be lysed while said beads are held in position in said magnetic array. Said magnetic array may further comprise features for the generation of virtual wells. Said retained beads may further comprise attached primers or primer sets, and said primers may be universal primers, or primers targeted to specific sequences associated with the type of cell bound to each bead, or may be universal primers or universal primer sets with barcodes, wherein said barcodes are associated with the cell type bound to each bead, or may be a combination of different primer types, and the types of primer types may be different for different bead types.

In some embodiments, after lysing of said cells, an amplification reaction may be performed. Said amplification reaction may be performed after a reaction to convert RNA to cDNA has been performed.

In some embodiments, said amplification may be a real time PCR reaction, wherein the quantity of RNA of a specific type(s) associated with each bead, and thus each said quantity of RNA of a specific type(s) may be determined for each bead and thus each cell type. In other embodiments, said amplification reaction may of any type of PCR reaction or isothermal reaction, and may generate clonal populations on said beads, or may generate multi-clonal populations, wherein each clone type may utilize different primers.

In other embodiments, a sequencing by synthesis reaction may be subsequently performed to determine the sequence of the amplified sequence(s) associated with each bead type, and thus with each cell type.

In further embodiments, after lysis of cells, DNA, RNA or other molecules of a specific charge may be retained, and the beads may be removed. In some embodiments, additional beads may be introduced to said magnetic array. Said newly introduced beads may have different primer types associated with said newly introduced beads as described herein. In some embodiments, an amplification reaction may be performed Magnetic Array Improvements In some embodiments of the current invention, the array of magnetic features may be configured such that a preferred position may be maintained by a magnetic or paramagnetic bead or particle. Such a preferred position may be desired so as to appropriately position said particle with respect to a sensor or sensors, and or to maintain the particle in a fixed location, so that the particle, and the charge attached to said particle does not move with respect to said sensor or sensors.

Figure 9:
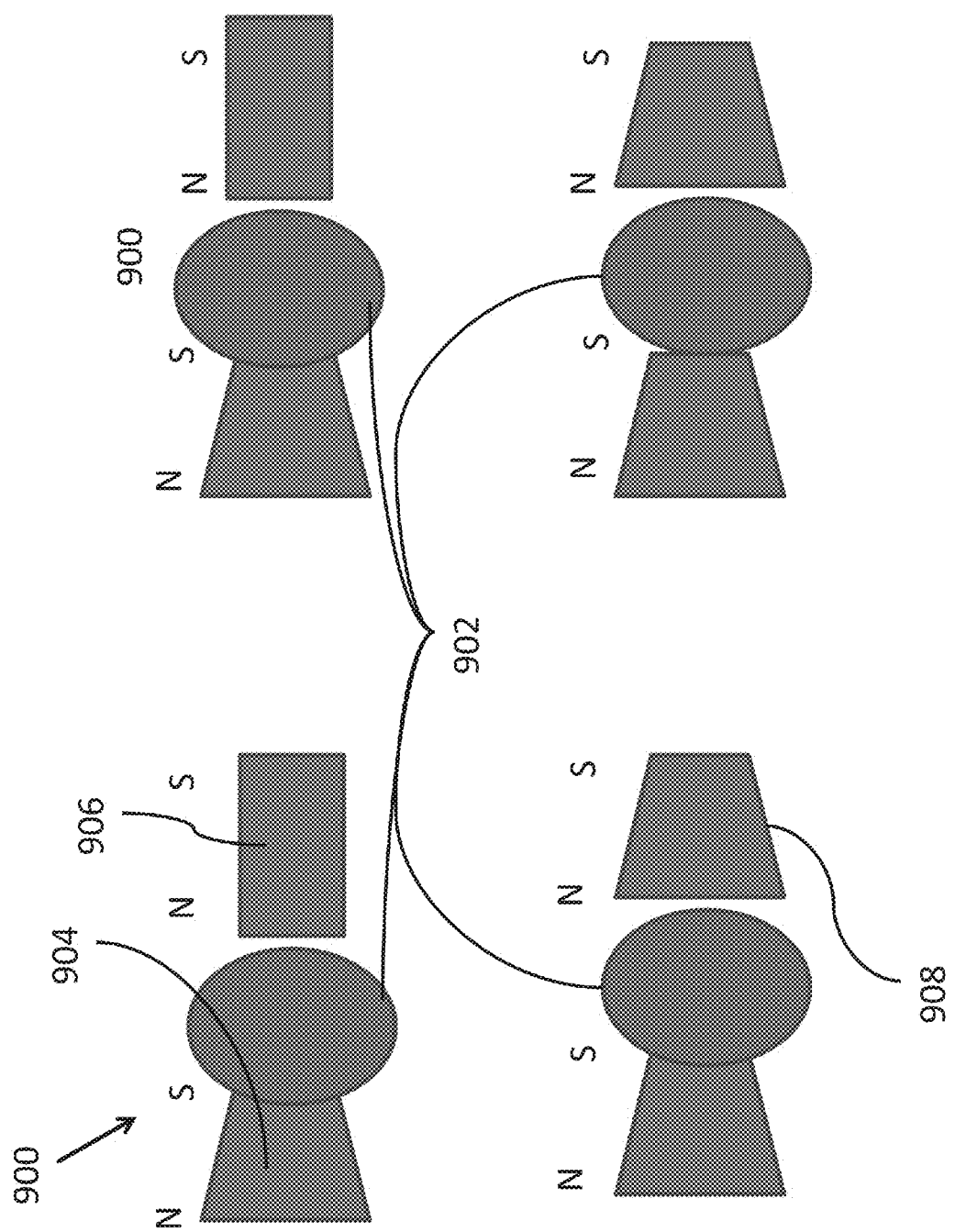
FIG. 9 shows two versions of magnetic arrays which may position magnetic beads in fixed locations.

In some embodiments said preferred location may result, at least in part from the configuration of the magnetic array element shapes, as shown in FIG. 9. FIG. 9 illustrates two different configurations 900 wherein at least some of the shapes in the array may be configured such that the density of the magnetic flux is more concentrated at one end of members of the magnetic array than at the other end or some other members of the magnetic array. In the top two pairs of magnetic elements, the left trapezoidal magnetic array element 904 is narrower at the south pole, than at the north pole of said trapezoidal magnetic array element. As the total flux level emanating from the magnetic array element must be the same at the two ends, the flux density at the narrower end of the trapezoidal magnetic array element 904 will be higher than at the wider end of said trapezoidal magnetic array element. As a higher concentration of flux corresponds to a higher force exerted on a magnetic or paramagnetic element, a higher force will be exerted on the magnetic or paramagnet particles or beads 902 by the narrower end of said trapezoidal magnetic array element 904, than is exerted by either the similarly sized magnetic array element 906 on the right side wherein the element on the magnetic array element on the right side 906 is of similar size, but is rectangular, and thus has a lower flux density and force. Similarly, a higher force will be exerted on the magnetic or paramagnet particles or beads 902 by the narrower end of the trapezoidal magnetic array element 904, than is exerted by either the similarly sized trapezoidal magnetic array element 908 on the right side wherein the element on the magnetic array element on the right side 908 has its wider end oriented towards the magnetic or paramagnetic particle or bead 902.

Figure 10:
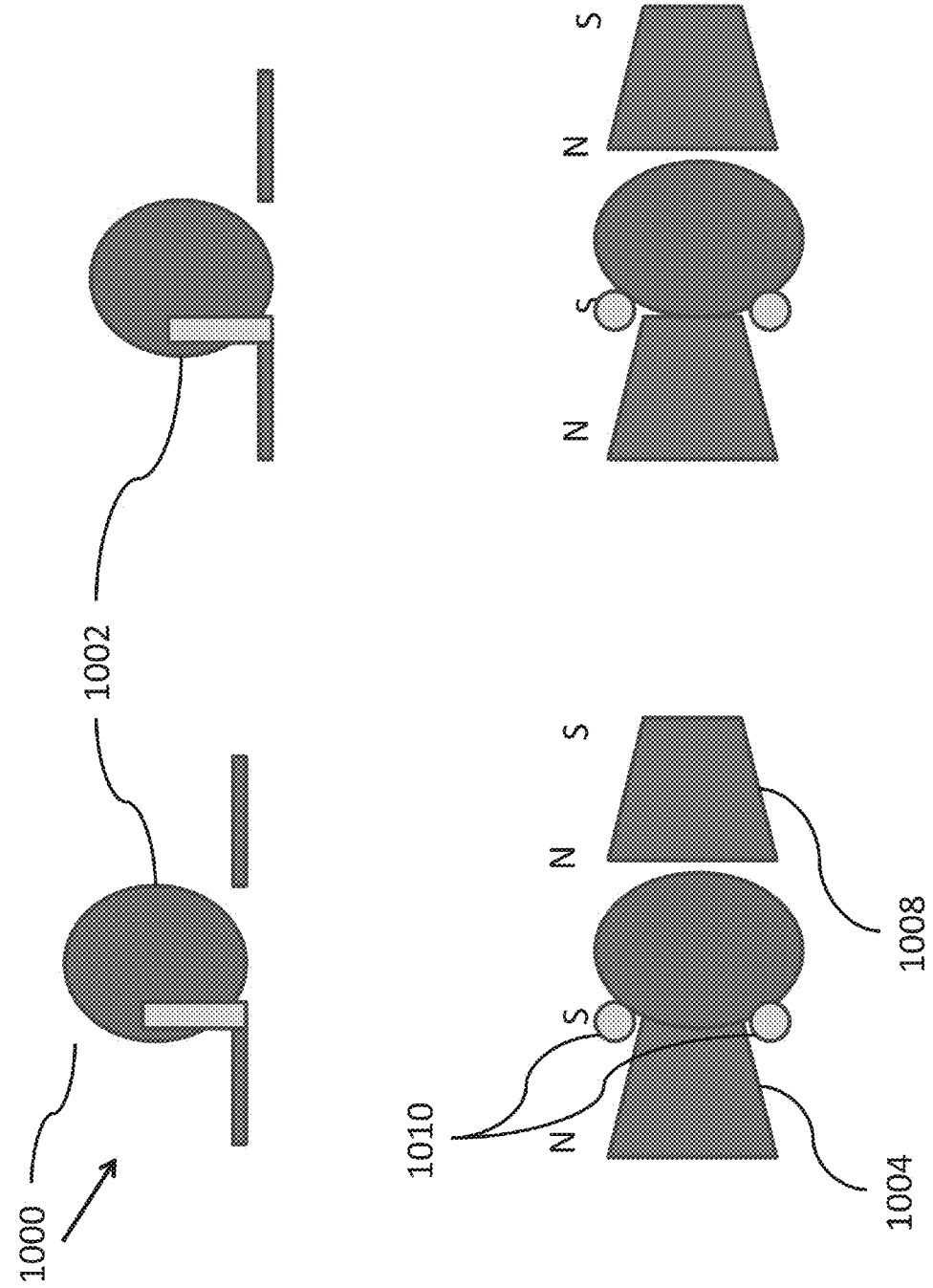
FIG. 10 shows an embodiment of a magnetic array which may locate beads in a fixed location.

In another embodiment of the current invention, additional features may be incorporated as part of fabrication of the magnetic array so as to inhibit motion of the magnetic or paramagnetic particle, or bead 1002 as shown in FIG. 10 In the embodiment shown, the magnetic or paramagnetic particle or bead 1002 is pulled preferentially towards the narrow end of the left trapezoidal magnetic array element 1004, and is pulled into contact with two posts 1010, as well as being pulled down into contact with the surface of the array, thus providing three points of contact to fully stabilize said magnetic or paramagnetic particle or bead 1002. The posts and magnetic array elements may provide minimal areas of surface contact, so as to permit maximal access by ions, dNTPs enzymes and other moieties. The posts and magnetic array members may be positioned with tight tolerances with respect to the sensor elements, so as to provide reproducible signal levels between different members of the sensor array.

In further embodiments of the current invention, a small well may be utilized, such that a magnetic or paramagnetic particle may rest on the upper corners of said well. The well may be round, or more preferably may be of some shape other than round if the magnetic or paramagnetic structure is generally spherical in shape, so as to allow better access to the bottom of the magnetic or paramagnetic particle by enzymes, dNTPs, ions and other moieties.

In some embodiments of the current invention, the magnetic array may be utilized to generate clonal populations which may be utilized for a variety of applications, including hybridization detection, hybridization pullout, sequencing and various other assays. Said assay may be performed with beads in the positions in the magnetic array wherein the amplification occurred, or the beads may be moved from the area or volume wherein the amplification reaction took place to another location with another magnetic array to perform said assay, or may be moved to another location wherein the beads may be bound using biotin streptavidin binding of other binding mechanism in a non magnetic array to perform said assay, or said assay may be performed in the magnetic array without moving the beads. In some embodiments of the current invention the sensors may be positioned directly under the magnetic or paramagnetic particle, so as to maximize the interaction between the charge associated with the DNA on the bead and the sensor. In other embodiments, wherein the bead may be bound or associated in such a manner that it is fixed and unable to rotate freely, it may be desirable to position the sensor off center from the paramagnetic, permitting access to areas of the particle which have free access to the aqueous environment and access to polymerase, dNTPs and other moieties is permitted and may have optimal enzymatic reaction which may then be read by sensor, in contrast to the areas which are in direct contact with the surface wherein the reaction may be inhibited as a result of lack of access to said aqueous environment. In some embodiments of the current invention, it may be desirable to utilize the differential flow which occurs in a channel to rotate the magnetic or paramagnetic particles, so as to provide optimal access by enzymes, dNTPs and ions to all surfaces of said magnetic or paramagnetic particles. Said differential flow results from the parabolic flow typical of small channels, wherein the bulk flow rate at the surface of a channel is zero, and the maximal flow rate in the channel is typically highest in the center of said channel. This may result in a significant flow rate differential between the bottom of the channel and the top of the magnetic or paramagnetic particle. The difference in flow rate between the top and bottom of the magnetic or paramagnetic particle will be a function of the size of the particle, the height and width of the channel, and the average flow rate in the channel. The DNA and or other moieties which may be attached to the magnetic or paramagnetic particle may provide a drag or pull on the top of the magnetic or paramagnetic particle due to the comparatively high flow rate at the top of said magnetic or paramagnetic particle. The flow rate at the bottom conversely will remain essentially zero, thus creating a significant rotational impetus. The magnetic array elements, potentially combined with other physical features may maintain the position of said magnetic or paramagnetic particle.

In some embodiments of the current invention, the flow rate may be maintained at a consistent flow rate while introducing and flowing dNTPs and or other reagents utilized while reading the sensors, thus maintaining a consistent average rotation rate. In other embodiments, it may be desirable to reduce the flow rate while reading the sensor, so as to prevent significant oscillations and motions of the magnetic or paramagnetic particle. In yet other embodiments, it may be desirable to increase the flow rate while flowing reagents through the flow cell during times when reading the sensor, so as to permit more surface area of the magnetic or paramagnetic particle to interact with the sensor during the time period the sensor is being read, thus permitting an increased averaging effect, which may reduce sensor readout variations due to variations in DNA attachment density on the surface of the magnetic or paramagnetic particle, or variations in the sensor readout due to irregularities in the shape of the magnetic or paramagnetic particle.

In other embodiments of the current invention, forces other than that resulting from changes in the flow rate velocity may be utilized to modify the rate of rotation or movement of the magnetic or paramagnetic particle. In some embodiments, the flux levels may be modified as a result of the movement of an external magnet which may be coupled through the magnetic array elements as a result of the higher permeability of the magnetic array elements. In an alternative embodiment, and electromagnet may be utilized to influence the amount of flux which interacts with the magnetic or paramagnetic particles. These changes in the amount of magnetic flux interacting with said magnetic or paramagnetic particles may reduce the frictional forces acting on the magnetic or paramagnetic particle, permitting more or less rotation.

In yet other embodiments, a quadrature rotation a magnetic or electric field may be utilized to rotate the magnetic or paramagnetic particles, in part as a result of the polarizability of the bead and associated DNA.

In some embodiments of the current invention, it may be desirable to use a force in addition to that which results from the flow of reagents through the flow cell to position magnetic or paramagnetic particles into appropriate locations associated in a one to one correspondence with sensors. In some embodiments, magnetic or paramagnetic particles may be flowed in a reagent stream into a flow cell or cells, and a magnet or electromagnet may be utilized to move magnetic or paramagnetic particles into positions associated with sensors such that a higher proportion of the magnetic or paramagnetic particles may be associated in a one to one correspondence with sensors than would have occurred without the use of such additional magnets or electromagnets.

The magnetic array also permits virtually complete allocation of beads to array locations. Low speed flow is sufficient to enable localized retention of the beads in the array, in a one to one correspondence between beads and array locations, without requiring centrifugation. In one embodiment, if even higher levels of filled versus unfilled locations on the array is needed or desired, the reagent flow may be circularized, such that the beads may be reintroduced to the flow cell. In another embodiment, the reagent flow may be stopped or slowed as the beads may be introduced to the flow cell. In another embodiment, the direction of the reagent flow may be reversed, potentially several times, providing more opportunities for the beads to fill the array. In yet another embodiment, the beads may be retained after flowing said beads into a flow cell by flowing said beads through either the inlet or outlet to a storage location, so that they be utilized in a subsequent sequencing process. To prevent beads from sticking in positions other than the intended bead locations, the flow can be increased to remove any weakly held beads, yet retain the correctly held beads. After a chemical process such as sequencing or amplification has been completed, the beads may be removed by either reducing the retention field flux, by adding a new field that pulls the beads away from the array, by increasing the flow rate of the fluid, by utilizing the air water interface associated with an air bubble, which may include a surface tension force, or any combination of the above steps, washing the beads from their locations in the array.

In an alternative embodiment, as shown in FIG. 3, an array of electrodes are used to retain charged beads, using either a DC field or a dielectrophoretic field, or both. As with the magnetic array, no well structure is needed to retain the bead, permitting free flow of components in solution. To insure that charged components in solution, such as the DNA sample, nucleotides, enzymes and other charged moieties may be readily able to flow through the volume above the array, a frequency of oscillation which is sufficient to retain the charged beads may be utilized, but which is sufficiently slow as to permit the moieties in solution to flow or diffuse away from a bead which is retained. The addition of depressions associated with the sensors in a one to one correspondence may result in better alignment between the beads and the sensors permitting better detection. In an alternative embodiment, pedestals or registration posts or other three dimensional structures may be utilized, for example, for better fluid flow may be incorporated.

In an alternative embodiment, wherein the beads may be localized in a one to one correspondence to the array, the beads may be brought into position by a magnetic or electrical field, and may then be held in place by an alternative means, such as DNA hybridization, biotin streptavidin binding, thiol binding, photo-activated binding, covalent binding, or the like. The binding may be initiated by a change in temperature, application of light, or by washing in a binding reagent or catalyst whilst said beads may be held in a one to one correspondence by said magnetic or electric field. After binding has occurred, the magnetic or electric field strength may be allowed to change in intensity or frequency, potentially being turned off. Said binding may be a reversible binding, permitting said beads to be washed out of the volume above the array of sensors.

A chamber-free electrical retention structure as shown in FIG. 3 may permit improved flow of nucleotides, polymerase and other components, as their flow is not hindered by a well structure, permitting better washing, more complete incorporation of bases, and faster cycle times then would be possible if the bead were in a well. If a well structure, beads and associated DNA hinders accessibility and flow, higher concentration of polymerase and nucleotides may be needed, to permit sufficient diffusion to all parts of a bead. Said higher concentrations of dNTPs and polymerase may increase an error rate due to misincorporation by said polymerase, resulting in higher levels of leading phase error then might occur with a chamber-free electrical retention structure.

Better washing, as permitted in a chamber-free electrical retention structure, may help to prevent leading phase error, by reducing the number of retained (unbound or nonspecifically bound) nucleotides, which may later be inappropriately incorporated in an incorrect cycle.

After removing the beads, it may be possible to bring new beads into the array, again in a one to one correspondence with sensors in the array, permitting reuse of the array. Reuse of the array may result in a reduction in the cost of sequencing DNA, potentially significantly reducing the cost of sequencing DNA.

Bead Coatings

In some embodiments of the current invention, the magnetic or paramagnetic particle may have surface coating thereon, said coating may be of sufficient porosity as to provide access for a polymerase or other enzyme, as well as for sample DNA, dNTPs ions and other moieties to pass therethrough. Said coating may be configured so that primers may be attached at an appropriate spacing, and may thereby provide a greater density of sample DNA and thus charge to interact with the sensors located thereby. Said coating may be of agarose, polyacrylamide or other cross linked polymer, or may be made of porous glass.

In other embodiments, said bead may have coatings configured so as to minimize or reduce nonspecific binding of DNA, proteins, or other charged moieties relative to the amount of nonspecific binding which may result when said DNA proteins, or other charged moieties interact with said beads without said surface coating. Said coatings may be similar to coatings described herein for use on the surface of a flow cell, sensor, enrichment module, or magnetic array, and any coating herein described for one surface may be utilized on other surfaces.

Non-Magnetic Bead Array

In one embodiment, in order to cause a higher percentage of sensors to have associated beads, beads may be attached to sensors by biotin streptavidin binding thiol binding or the like after a set of beads has been localized by one of the aforementioned structures. Additional beads may then be introduced into the sensor array region, and the process repeated. If binding agents are localized to areas above sensors, as may be done as previously described, any excess beads which are caught or pinched by the structure will not bind, and may be washed away before beginning the sequencing cycles.

In yet a further embodiment, a significant excess of beads may be introduced into the sensor array region. A single control line at an exit from the sensor array region may be activated to trap the set of beads. The aqueous conditions and/or temperature may be changed to permit binding of beads to the sensors. The excess of beads may then be removed by releasing the control line allowing flow of the beads out of the sensor array region with an aqueous reagent.

In some embodiments of the current invention magnetic beads may be utilized without a magnetic array. Said magnetic beads may be caused to be separated at a spacing which matches the spacing of a sensor array, and then may be caused to bind to the sensor array by changing aqueous conditions, temperature or the like as previously described. Slow translation or movement of the beads may be appropriate after conditions have caused to be appropriate for binding in order to enable alignment of the beads with the sensors. Such translation or movement may need to occur in multiple dimensions, which may include x, y, theta, and spacing. The addition of depressions associated with the sensors in a one to one correspondence may result in better alignment between the beads and the sensors permitting better detection.

Bead Alternatives

In one embodiment of the current invention wherein the magnetic, paramagnetic, non magnetic particles may be of shapes other than spherical for use with either a sensor array with magnetic retention, a sensor array with electrical confinement, or a sensor array with self assembled particles. In other embodiments, the particle may dentritic, enlarging the surface area of said particle. Said dentritic particle may be generally spherical, planar, oval, or any other shape. In yet other embodiments, said particle may be porous; if said particle is porous, the pore size may be of sufficient size as to permit free movement of DNA, polymerase, dNTPs and other moieties necessary for primer extension sequencing or other applications as appropriate. In all places where the term bead is utilized, it may be assumed that it may be of any shape as described herein.

In another embodiment, not requiring a magnetic bar array, the beads may be replaced with DNA balls, created by using rolling circle amplification. The DNA balls may then be digested by a DNA nuclease. In another embodiment, the balls may fabricated from a monomer or polymer, such as polystyrene, which may be dissolved subsequent to sequencing, using an organic solvent such as acetone, thus freeing the attached DNA by same said process, both of which may then be removed from the flow cell by flowing a reagent through said flow cell.

In yet another embodiment, the bead may be held in place by a binding between moieties attached to the well and moieties attached to the bead. The well may be shorter than the radius of the bead, and may have a shape other than circular, so that reagents may flow around the bead, while the bead may be bound at several points at the entrance to said well. The binding may be a Streptavidin Biotin binding, a DNA-DNA binding, a DNA-PNA binding, a PNA-PNA binding, Thiol-Au binding, photo-activated binding, covalent binding, or the like. Said binding may be released by raising the temperature, or by introducing a reagent which reduces the affinity between the moiety on the well and the moiety on the bead, permitting the beads to be removed from the flow cell by flowing a reagent through said flow cell. The beads may be further induced to move from the well in which said bead has been bound by sonicating the bead and well structure. Said sonication may be done at the same time that a reagent is flowed through the flow cell in order to remove said beads from said flow cell.

Chamber Free Amplification

In the process of amplifying DNA in chamber free system, various factors may be potentially subject to optimization. Among these include the frequency, voltage and size and shape of the confinement "cell" used to confine the polymerase, target DNA and generated amplicons. If confinement were the only consideration, it would be possible to confine almost any size of amplicon, without regard to the small size of said amplicon. However, in order to be able to have a field strong enough to insure proper confinement, the field may prevent proper activity of the polymerase incorporation of bases during the PCR or isothermal amplification process, or may pull the polymerase and or extended primer from the complex of the target DNA extended primer and polymerase. In one embodiment of the current invention, it may be desirable to optimize a combination of frequency, voltage and size of the confinement cell, depending on the size of the amplicon.

In some embodiments, said amplification may be an inverse PCR amplification reaction, a hot start PCR amplification reaction, a methylation specific PCR amplification reaction (MSP), a nested PCR amplification reaction, a reverse transcription reaction, a reverse transcription PCR amplification reaction (RT-PCR), a Touchdown PCR amplification, an intersequence specific PCR amplification reaction (ISSR-PCR), a co-amplification at lower denaturation temperatures (COLD-PCR), solid phase amplification, bridge PCR amplification, or single primer bridge amplification.

In some embodiments, said amplification reaction may be a helicase dependent amplification (HDA), a nicking enzyme amplification reaction (NEAR), a recombinase polymerase reaction (RPA), transcription mediated amplification (TMA), self-sustained sequence replication (3SR), nucleic acid based amplification (NASBA), signal mediated amplification of RNA technology (SMART), loop mediated isothermal amplification of DNA (LAMP), isothermal multiple displacement amplification (IMDA), solid phase isothermal, bridge isothermal, single primer isothermal amplification (SPIA), circular helicase dependent amplification (cHDA), or rolling circle amplification.

Waveform Shape

In generating a DC field for electrophoretic concentration or confinement, electrolysis products can build up. These include hydronium and hydroxide ions. To minimize effects from these ions the DC field can be pulsed so the net DC is much lower. In some embodiments the pulse duty cycle can be reduced after the DNA has migrated closer to the center electrode. In other embodiments the process can use DC to concentrate the DNA and then use AC to maintain concentration or confinement of said electrolysis products. In other embodiments both DC and AC can be used for concentration and confinement.

In generating a dielectrophoresis field, typically a sinusoidal waveform is utilized. While this may be ideal for an application which intended strictly for confinement or separation of different species, it may cause issues for a system wherein a biochemistry reaction may be performed within the confinement volume. For example, high fields are likely to result in localized heating. In one embodiment of the current invention, a modified sinusoidal waveform may instead be utilized. For example, the modified sinusoidal waveform may have the voltage removed at the top of the sinusoid, or at any other point in the sinusoidal waveform, allowing localized diffusion, permitting hybridization of the amplicons to primers, binding of polymerase to the duplex DNA, and binding and incorporation of nucleotides or nucleotide analogs. The field may then be reinstated after an appropriate period of time. The same process may occur at the peak with the opposite sign in the modified sinusoidal waveform. In other embodiments, any other alternating current waveshape can be utilized for concentration or confinement. Alternatively, the interruption in the sinusoidal waveform may occur only once per cycle, or may occur once in every several cycles, or once in many cycles, so that any "stray" amplicons may be captured in the regions with lowest field strength and returned to the main volume of the confinement volume. Alternately other wave forms such as square, trapezoidal, non symmetrical wave forms, etc may be used.

Thermal Cycling Virtual Wells

In some embodiments monoclonal beads may be generated in a small microfluidics device. In one embodiment the electrodes and magnets may be fabricated on a thin sheet wherein a top surface may be bonded or fused in place creating an integrated microfluidics device. The microfluidics device may have electrical and fluidic connections made to it. The microfluidics device may then be placed in good thermal contact against a first heated plate, for example by vacuum or air pressure. A second plate may be situated above at a different temperature. The two temperatures may be chosen to facilitate PCR amplification. After one temperature point is complete the card may be transferred or caused to come into contact with the upper heated plate, for example by vacuum or air pressure. Because only the thin card and the reagents in the card need to change temperatures the system can have fast temperature transitions, and consume minimal power.

In other embodiments that provide a minimal thermal mass, the electrodes built into the amplification microfluidics device may be utilized as resistive heaters to locally heat the liquid. In some embodiments the change in resistance of the electrodes could be used to measure the temperature for better thermal control. In other embodiments the sensors, such as the NanoBridge or NanoNeedle may be utilized as a temperature sensor for better control of the area of interest.

Non-Thermostable Polymerase and Thermostable Polymerase

In some embodiments, it may be desirable to perform DNA amplification from a single copy of DNA. If a polymerase error is made in amplification at an early point in the amplification process, such as in the first cycle in a PCR amplification, said error will proliferate such that it may not be possible to differentiate between the correct sequence and the error sequence. Thermostable polymerases typically have much higher error rates than mesophillic polymerases or thermophillic polymerases which may be not suitable for PCR as they inactivate during the denaturation step of PCR. Thus in some embodiments of the current invention it may be desirable to utilize a highly accurate polymerase for the initial portions of a PCR reaction, wherein said highly accurate polymerase may not be sufficiently thermostable to prevent inactivation during PCR, but may provide better accuracy than a more thermostable polymerase which is sufficiently thermostable to prevent significant inactivation during PCR. Said highly accurate polymerase may have a low $K_{off}$, such that said highly accurate polymerase may be substantially still bound to the active extension site, in the presence of other polymerases which may be sufficiently stable to prevent significant inactivation during the denaturation steps of a PCR amplification.

In some embodiments, said highly accurate polymerase may be introduced to a volume with primers and template prior to the introduction of said more thermostable polymerase. In other embodiments said thermostable polymerase may be heat activated, such that any heat activated polymerase will be inactive for the first cycle(s) of the PCR.

In other embodiments a combination of isothermal and PCR amplification reactions may be utilized, wherein initial amplification may be performed by a highly accurate non thermal stable polymerase, and subsequent amplification may be performed by a less accurate thermal stable polymerase which is not substantially inactivated by the denaturation step of PCR.

Combined Sensor and Confinement Array

Amplification On or Near Sensor

In some embodiments, wherein a clonal population is generated in the area of individual sensors in a sensor array, the sensors may be NanoNeedles or NanoBridges or other sensors to detect the event of polymerization. In one embodiment, primers may be preferentially attached to the surface of the sensors. Said primers may be preferentially attached as a result of a difference in materials, wherein the material of the sensor is more advantageous for attachment then the areas between the sensors of the sensor array. In an alternative embodiment, a mask may be applied to areas between the sensors of the sensor array, and a surface modification may then be performed. Subsequently, the mask may be removed; leaving an area between the sensors of the sensor array wherein the surface modification has not been performed. The surface modification may include attachment of biotin, applying a layer of gold and various other methods as are known in the art.

Primers may then be preferentially applied to the areas on the surfaces of the sensors in the sensor array. In one embodiment, the primers could be attached as a result of a biotin streptavidin binding, wherein the streptavidin is attached to the 5' end of the primers. In another embodiment, a thiol group may be attached to the 5' end of the primers, which can then bind to the gold layer previously applied above the sensor, forming an Au—S bond. If a PCR reaction is desired, the primers may be modified with DTPA such that two thiol gold bonds are formed, preventing the dissolution which may otherwise occur from the 60 to 95 C temperatures routinely used in PCR.

After a set of sequencing cycles has been completed, the primers may be removed and replaced. Buffer conditions can be changed to weaken the biotin streptavidin bond, such as high concentrations of GuHCl at low pH; alternatively the temperature can be raised to over 70 C to break the biotin streptavidin bond. Thiol bonds can likewise be broken at elevated temperatures. Aggressive means may be utilized, as damage to the polymerase and DNA is no longer consequential, as the sequencing reaction has already been completed. In one embodiment, organic reagents may be utilized to break the binding between the extended primer and the surface, such as a covalent binding. After the extended primers have been removed, new primers may be flowed into the volume above the sensors, enabling the device to used again for another set of sequencing cycles on a another set of DNA samples.

In some embodiments as schematically depicted in FIG. 12, the sensor array may have elements 1200 that are provided with an additional array of electrodes 1206, which may be utilized to perform dielectrophoretic concentration. Dielectrophoretic concentration may be initially performed to attract sample DNA dNTPs, and primers to each sensor region. Amplification can then commence in the region of each sensor where a sample DNA molecule is located. During the amplification process, the dielectrophoresis forces may also aid in preventing cross contamination between different sensor regions undergoing amplification by retaining amplicons. In order to insure that polyclonal regions are not generated, the concentration of input DNA needs to be low enough that most sensor regions have one or zero sample DNA molecules. DNA samples could be single stranded or double stranded depends on the amplification methodology. The amplification reaction can be either a PCR reaction, or an isothermal reaction. In some embodiments the additional electrodes 1206 are shown as having the same voltage relative to voltage level of the sensors. In an alternative embodiment electrodes on either side of a sensor may have voltages of opposite sign relative to each other.

Said sensor array elements 1200 may be fabricated on a substrate 1212, and may have magnets 1216 utilized for retention of magnetic or paramagnetic particles or beads 1202, wherein said magnetic or paramagnetic particles or beads may be held down against an electrode 1204, an against a dielectric 1210 and or upper electrode 1208. Detection may utilize said electrode 1204 and said upper electrode 1208, while dielectrophoretic concentration/confinement may utilize electrode 1204 and outer electrode 1206, wherein said outer electrode may comprise a single electrode or may comprise multiple electrodes.

Amplification may be a solid phase amplification, wherein one primer is on the surface of the bead, and a second primer is in solution, or the amplification may solid phase wherein all primers are on the bead, or the amplification may be performed whereby both primers are present in solution, and one primer, or both primers are also present on the bead.

The electrode configuration may take various different forms, including a planar electrode on both major planes of the flow cell, or there may be on electrode on the surface opposite the beads, and a set of smaller electrodes associated with each detector location.

FIG. 12 illustrates the use of the amplified regions above the sensors in the array of sensors in a sequencing reaction. After the amplification reaction has been completed, the volume above the sensor array may be washed, removing amplicons, polymerases, and dNTPs. Polymerase and individual dNTPs may then be flowed into the volume above the sensor array, permitting binding, incorporation, and detection of the incorporation events, resulting in the determination of the sequence of the different amplified sample DNA molecules.

In some embodiments, said sensor may be utilized for several purposes, for example, said sensor may be utilized to detect the presence of beads when introducing beads from different samples, and may thence be utilized to detect amplification associated with said bead, wherein said detection of amplification may be real time PCR amplification detection or may be end point PCR amplification detection, and said sensor may thence be utilized as a sequencing detector; In some embodiments, any combination of different uses for said detector may be utilized.

In other embodiments, An array may be fabricated wherein said array may comprise a sensor array as described herein, a confinement structure array utilized to generate a virtual well array as described herein, and a magnetic array as described herein may be combined, such that all three functions are combined in at least some portions of said array. In other embodiments, said array may comprise any two of comprise a sensor array as described herein, a confinement structure array utilized to generate a virtual well array as described herein, and a magnetic array as described herein.

Enrichment of Clonal Beads

When generating clonal beads a large percentage of the beads will have no DNA template. In addition others may have poor amplification. These beads do not provide useful sequencing so it is desirable to remove these beads to improve instrument throughput and reagent utilization. In some embodiments of the current invention an enrichment module is used which separates the beads with no or minimal amounts of template using an electric field.

The beads on which amplification has occurred have more fixed negative charge from the amplified DNA and can be separated from those, on which amplification has not occurred, by the use of an electrophoretic separation. This permits the situation wherein most positions in the magnetic array may be occupied by beads which have had an amplification reaction occur, and may be thus suitable for usage in a sequencing reaction.

Basic Configuration of Device

Figure 13C:
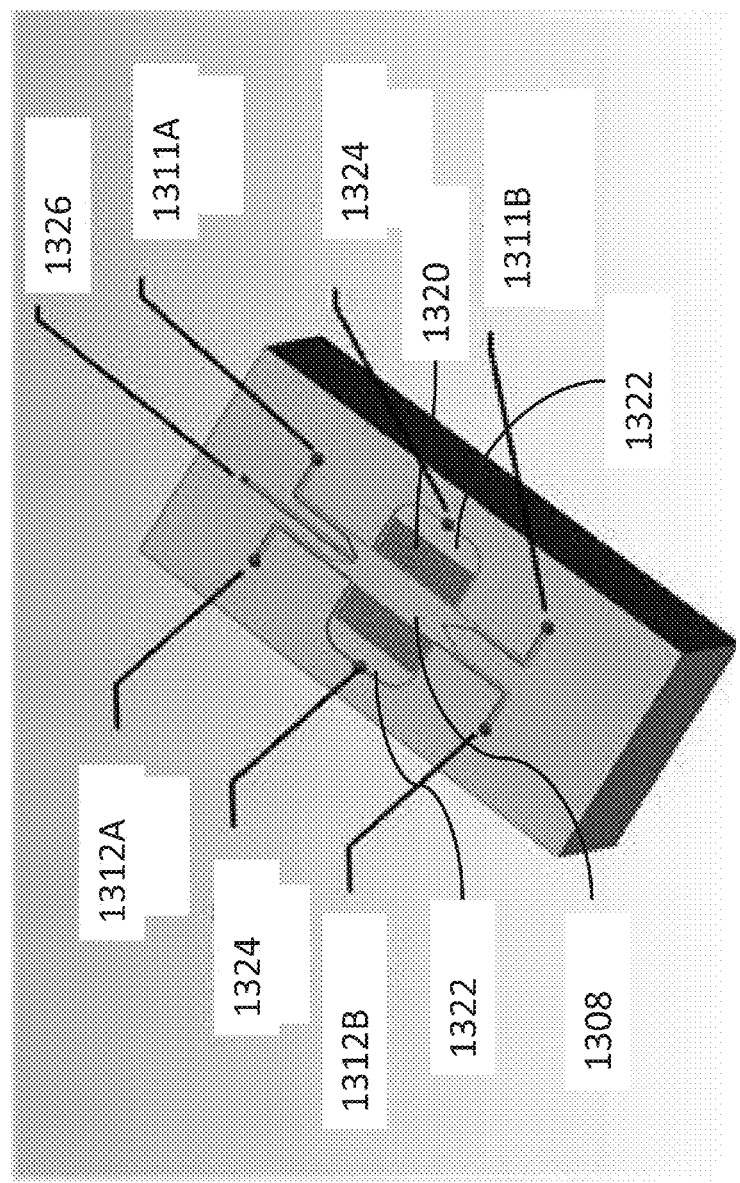

Beads fully loaded with templates have a higher charge so will move farther in an electric field than beads with only primers or few templates. In one embodiment as shown in FIG. 13A, FIG. 13b and FIG. 13C, this separation is done in a flow through module. A first fluidic input 1311A allows the injection of mixed beads. A second inlet 1312A allows the injection of a buffer solution without beads. A first outlet 1311B is downstream from the first inlet 1311A. A second outlet 1312B is downstream from the second inlet 1312A.

Flow Rate Control

The fluidic flow rates can be set by fluidic resistance or pumping speed such that more liquid flows in the second inlet. In the embodiment shown in FIG. 13B, the inlet and outlet widths may be varied to create different fluidic resistances, but other methods of modifying the fluidic resistance such as different length, height may be anticipated, or the use of flow restrictors in parts of the system external to the enrichment module 1300. Similarly the fluidic resistance of the first outlet 1311B and second outlet can be modified so more liquid flows out the first outlet 1311B. In such a setup beads without a small velocity perpendicular to the flow will exit the first outlet port 1311B. Additional output channels can be added to facilitate separation of beads with medium levels of template. In some embodiments, the flow rate in each output channel may be controlled directly by providing individual pumps for each outlet channel.

A pair of electrodes 1313, may be provided which enable generation of an electric field perpendicular to the fluid flow in the separation section 1310 such that the template loaded beads, which may be brought into the enrichment module 1300 through inlet 1311A while an additional reagent may be introduced to the module through a second input 1312A, may migrate out of the flow path towards second outlet 1312B. Fluidic ports 1309 allow connection to the system plumbing.

The electrodes 1313 may be made of any electrode material compatible with electrophoresis. In some embodiments discrete metal wires may be used but metal traces may be also anticipated. Metals such as platinum, platinum/iridium, gold and other noble metals or alloys may be anticipated as well as corrosion resistant materials such as stainless steel. Non metal electrodes may be also anticipated.

In another embodiment the fluidic flow rates can be set by fluidic resistance or pumping speed such more or less fluid flows out the first outlet than the second outlet allowing steering of the bead flow stream. In yet another embodiment the bead stream could be adjusted by both the inlet and outlet fluid flows.

Materials and Fabrication Methods

The flow through enrichment module 1300 can be constructed of non conducting materials such as molded plastic, glass, ceramic or moldable polymers such as PDMS, or of conductive materials which may be coated with a nonconductive coating, or combinations or these materials, or in combinations with other materials. Fluidic components can be fused, bonded, or held together with a clamp mechanism to create an enrichment module including a separation section 1308. The enrichment module may in one embodiment include a molded upper piece 1308, and a flat substrate 1302. In other embodiments, the enrichment module may be made of more than two pieces, such as for example, three, four, five or more components. If two components may be used, both sides may have non planar surfaces, such that fluidic or control channels may be formed in either component. If more components may be utilized, any one of them be planar or shaped such that they include channels, depressions or protrusions, or may be a combination of planar and shaped such that they include channels, depressions or protrusions.

Zeta Potential Reduction

In some embodiments, wherein the surface or a portion of the surface of one or more components of the enrichment module may have a zeta potential sufficient to cause significant electroosmotic flow, it may be desirable to minimize any mixing or turbulence with might otherwise result from said electroosmostic flow. In some embodiments, materials such as $TiO^2$, $ZrO^2$, or $BaTiO^3$ may be selected wherein the zeta potential and the resulting electroosmostic flow may be significantly reduced. In some embodiments, the zeta potential and the relationship between the zeta potential and a change in pH may change depending on a surface coating; in some embodiments the zeta potential may change significantly with changes of pH such as the pH dependency of Silica, while in other cases, the zeta potential may be change very little with respect to pH, particularly in the pH range from pH 7.5 to pH 9, such as the pH dependency of $BaTiO^3$.

In other embodiments, surface coating(s) such as PEG (Poly Ethylene Glycol), methyl cellulose, n-dodecyl-B-D-maltoside, acrylamide, fluorinated alkane chains, PTFE, acrylate, or other cross-linked or partially cross-linked polymers may be utilized to modify the zeta potential, or combinations of surface coatings may be utilized to similarly minimize the electroosmostic flow. In some embodiments, polymers may be utilized to fill the aqueous volume of the electroosmostic flow restriction section.

Electroosmotic Flow and Turbulence Reduction

In other embodiments, a physical structure as shown in FIG. 13C may be utilized to reduce or eliminate unwanted mixing and turbulence due to electroendosmotic flow. Such a structure may have a flow constraining section 1320, and said flow constraining section(s) 1320 may be utilized on both sides of separation section 1308. Electric field may be distributed from electrodes (not shown) through buffer reservoir section(s) 1322. Said electrodes may be positioned in auxiliary input port(s) 1324, which may be utilized to bring buffer to and through the buffer reservoir section(s) 1322 and flow constraining section(s) 1320. In an alternative embodiment the electrodes may be positioned in the buffer reservoir section(s) 1322, with electrical connection to a voltage source which may be external to enrichment module 1300. Input beads and reagents may be brought into said separation section 1308 through input ports 1311A and 1312A, or reagents may be brought in through input ports 1311A and 1312A, while beads are brought in through center input port 1326. Beads may be separated between output ports 1311B and 1312B.

In an alternate embodiment the electrodes may be positioned in a buffer reservoir(s) separate from the structure shown in FIG. 13C with a fluidic connection to allow current flow into the enrichment module. In some embodiments, said buffer reservoir(s) may allow electroendosmotic flow to move in one direction across the enrichment flow cell and may generate a static pressure differential or difference in fluid height in said fluid reservoirs as a result of said fluid movement, rather than having a circular flow with concomitant turbulence that would occur with a sealed flow cell wherein any flow in one direction must be matched by flow in the opposite direction. In some embodiments the voltage can be stopped periodically to allow the fluid reservoirs to return to their equilibrium state, wherein the liquid level in each reservoir is at the same level, after electroosmostic pumping. In other embodiments, the volume or cross section of said reservoirs may be significant relative said electroosmostic pumping, such that bead sets or multiple bead sets may be separated or enriched prior to needing to allow said fluid reservoirs to return to their equilibrium state.

In other embodiments the zeta potential magnitude can be reduced by protecting the silanol groups with a compound such as trimethylchlorosilane which decreases the number of ionizable silanol groups.

FIGS. 13D and 13E microphotographically illustrate the use of a structure as shown in FIG. 13C, wherein a stream of input beads 1314 is illustrated without a field applied in FIG. 13D, and thus all input beads 1314 are carried to output 1311B as if they were lower charged beads 1314A, and no beads appear to be higher charged beads 1314B pulled to outlet port 1312B. The flow constraining section 1320 shown in FIG. 13C is shown in more detail, showing the fluidic passages 1316, and support columns 1318. In FIG. 13E, wherein a field is applied to said separation section 1308, and said stream of input beads 1314 is separated into low charged beads 1314A which is carried to output port 1311A, and higher charged beads 1314B are pulled and carried to output port 1312B.

Device Dimensions

In some embodiments, the thickness or depth of the separation section 1308, fluidic inputs 1311A, 1312A, fluidic outputs 1311B, 1312B, separation section 1308, electroendosmotic flow restriction section(s) 1320, and buffer reservoir(s) 1322 may be the same. In other embodiments, the thickness or depth may be different for different sections, for example, the thickness of the electroendosmotic flow restriction section(s) 1320, may be less than that of the separation section 1308 or the buffer reservoir(s) 1322.

In some embodiments, the thickness or depth of the separation section 1308, and other fluidic sections of the enrichment module may be from 10 to 1000 µm; in other embodiments the thickness or depth of the enrichment module may be from 20 to 200 µm, 50 to 150 µm, 200 to 500 µm, or from 70 to 130 µm.

In some embodiments the width of the flow restrictors in the electroendosmotic flow restriction section(s) 313 may be from 10 to 1000 µm, in other embodiments, the width of the flow restriction may be from to 200 µm, 50 to 150 µm, 200 to 500 µm, or from 70 to 130 µm.

In some embodiments the length of the enrichment zone can be up to 2 mm, 2 mm to 10 mm, 10 mm to 100 mm. In some embodiments the width of the enrichment zone can be up to 1 mm, 1 mm to 4 mm, 4 mm to 10 mm and 10 mm to 100 mm.

FeedBack System

In some embodiments, said enrichment module 1300 may have a feedback system (not shown) to compensate for varying charge levels that may exist between different batches of beads. Such a feedback system may then permit the electrophoretic voltage to be automatically tuned for a particular batch of beads, and to be automatically retuned for a subsequent batch of beads. Said feedback system may be utilize reflected light, absorbed light, deflected light, transmitted light, fluorescent light, capacitive coupling to the beads, direct conductivity detection of the Debye layer associated with the beads, ISFET/ChemFET detection of the beads, or may utilize any other appropriate detection means. Said detection means may be configured such that detection of beads is effectuated in or associated with one or more fluidic outputs 1311B and 1312B, or may be configured such that detection of beads is effected in or associated with the separation section 1308.

In some embodiments said feedback system may be utilized during a separation of a batch of beads, tuning the flow rate and electroosmostic voltage so that the beads are optimally separated and flow into the nominal desired position in each output 1311B and 1312B. Said flow rate control may be effectuated by the use of a variable pressure applied to said flow, a variable vacuum applied to said flow, a variable restriction in the said flow, or any combination thereof.

Concentration of Beads

In some embodiments, the bead slurry may need to be concentrated. In one embodiment the beads solutions is passed by a magnet to hold the beads. By removing the magnetic field or using a higher flow rate the beads can be released in a more concentrated form.

Separation of Non-DNA Particles

In some embodiments said enrichment module 1300 may be utilized to separate negatively charged DNA from proteins, including cellular membrane fragments which may be comingled with said DNA after lysing of the cell(s) from which said DNA and said proteins and said cellular membrane fragments may have originated. In some embodiments it may be desirable to separate said DNA from proteins, most of which may be positively charged, and to also separate said DNA from proteins which may be negatively charged at neutral pHs, such as human serum apotransferrin, thyroglobulin, or BSA. Such proteins which may be negatively charged at neutral pHs typically have pKa values above 4.0, whereas the pKa for DNA is 1.0. The electrophoretic mobility of proteins is typically much lower than that of the highly negatively charged DNA, permitting easy separation of DNA in an enrichment module 300. Such separation may be performed at a low pH such as a pH below 7, a pH between 6 and 7, a pH between 5 and 6, a pH between 4 and 5, or a pH between 3 and 4, permitting the enrichment module to run below the pKa of said proteins, and above the pKa of said DNA.

Concentration and Capture after Separation

In some embodiments, the DNA may be dielectrophoretically captured after being substantially separated from any proteins and cellular membranes. Said dielectrophoretic capture may be effected in a fluidic outlet 1311B, 1312B, or may be effected in a separate module. After said dielectrophoretic capture, the buffer may be changed, for example form a low pH as previously described to effect a separation from proteins or cellular membranes, to for example, a buffer suitable for PCR, isothermal amplification, or sequencing, wherein the pH may be approximately optimal or otherwise suitable, for example, polymerase activity.

Sticking Prevention Using Voltages

The voltage applied to the electrodes 1313 can be reduced or even reversed periodically if necessary should beads stick to the electrodes. The voltages used may be greater than that required for electrolysis (1.23V at 25 C at pH 7), or may be less than the voltage needed for electrolysis. Higher voltages and narrower gaps provide a higher field strength and more force on the beads. The voltage on the system can be calibrated by flowing beads without or with limited template and setting the voltage and or flow rate such that these beads may be not moved far enough to enter the second outlet while beads with template may be directed into the second outlet.

Sensor array Flow Cells

Reuse of Flow Cell

In one embodiment of the current invention, beads may be removed from the flow cell as a result of actions and methods which are performed within the same instrument wherein the flow cell is utilized to sense a reaction, such as a sequencing reaction.

In another embodiment of the current invention, the flow cell assembly may be removed from the instrument wherein the flow cell is utilized to sense a reaction, such as a sequencing reaction, and moved to another instrument or device, wherein the beads may be removed from the flow cell.

In yet another embodiment of the current invention, the flow cell assembly may be removed from the instrument wherein the flow cell is utilized to sense a reaction, such as a sequencing reaction, and shipped to a central refurbishment site, wherein the beads may be removed from the flow cell.

In another embodiment of the current invention, the flow cell assembly may be removed from the instrument wherein the flow cell is utilized to sense a reaction, such as a sequencing reaction, and moved to another instrument or device, wherein coatings may be applied, or removed and reapplied to the flow cell and or fluidics manifold.

In yet another embodiment of the current invention, the flow cell assembly may be removed from the instrument wherein the flow cell is utilized to sense a reaction, such as a sequencing reaction, and shipped to a central refurbishment site, wherein coatings may be applied, or removed and reapplied to the flow cell and or fluidics manifold.

Surface Coatings

In some embodiments of the current invention, the flow cell and or the fluidics manifold may have various surface coatings. Such surface coatings may be utilized to reduce nonspecific binding of moieties in the various reagents which are utilized by the instrument, to the surfaces in said flow cell or fluidics manifold. In some embodiments, said coatings intended to reduce nonspecific binding may include PEG (Polyethylene Glycol), BSA (Bovine Serum Albumin), PEI (Polyethylenimine), PSI (Polysuccinimide), DDM (n-dodecyl-b-D-maltocide), fluorinated coatings, Teflon coatings, silanization coatings, or other appropriate coatings may be utilized.

In one embodiment of the current invention, the coatings may be applied, or removed and reapplied to the flow cell and or fluidics manifold as a result of actions and methods which are performed within the same instrument wherein the flow cell is utilized to sense a reaction, such as a sequencing reaction.

Multiple Sensor Channels

Figure 14:
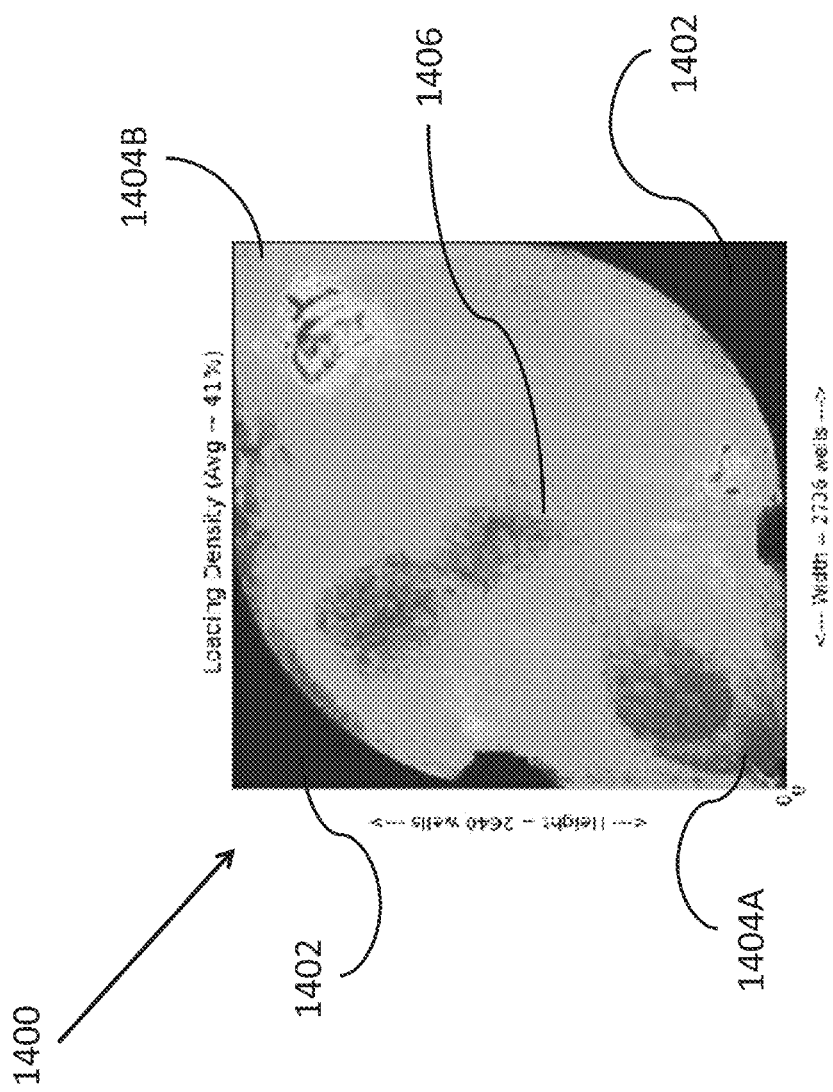
FIG. 14 illustrates the bead loading density for an existing flow cell.

In one embodiment wherein the quantity of data which is collected is minimized, it may be desirable, in addition to increasing the speed of the reaction, to align the active regions with the normally occurring rectilinear nature of semiconductor electronics. In previous systems, the locations of the active reactions may not align well with an array of detectors. It is preferable to arrange the detector electronics in a strict rectilinear fashion, as opposed to prior art which brings reagents in and out from the corners 1404A and 1404B of a chip 1400 as shown in FIG. 14 This approach both prevents alignment with the reagent slug, and wastes a significant area of the chip, as the reagent slug cannot flow well (or at all) to the other corners of the chip 1402, as well as causing nonuniformity of flow (and loading efficiency 1406) due to the large difference in cross sectional area from the center of the chip to the inlet and outlet ports in the corners of the chip 1404A and 1404B.

Figure 15:
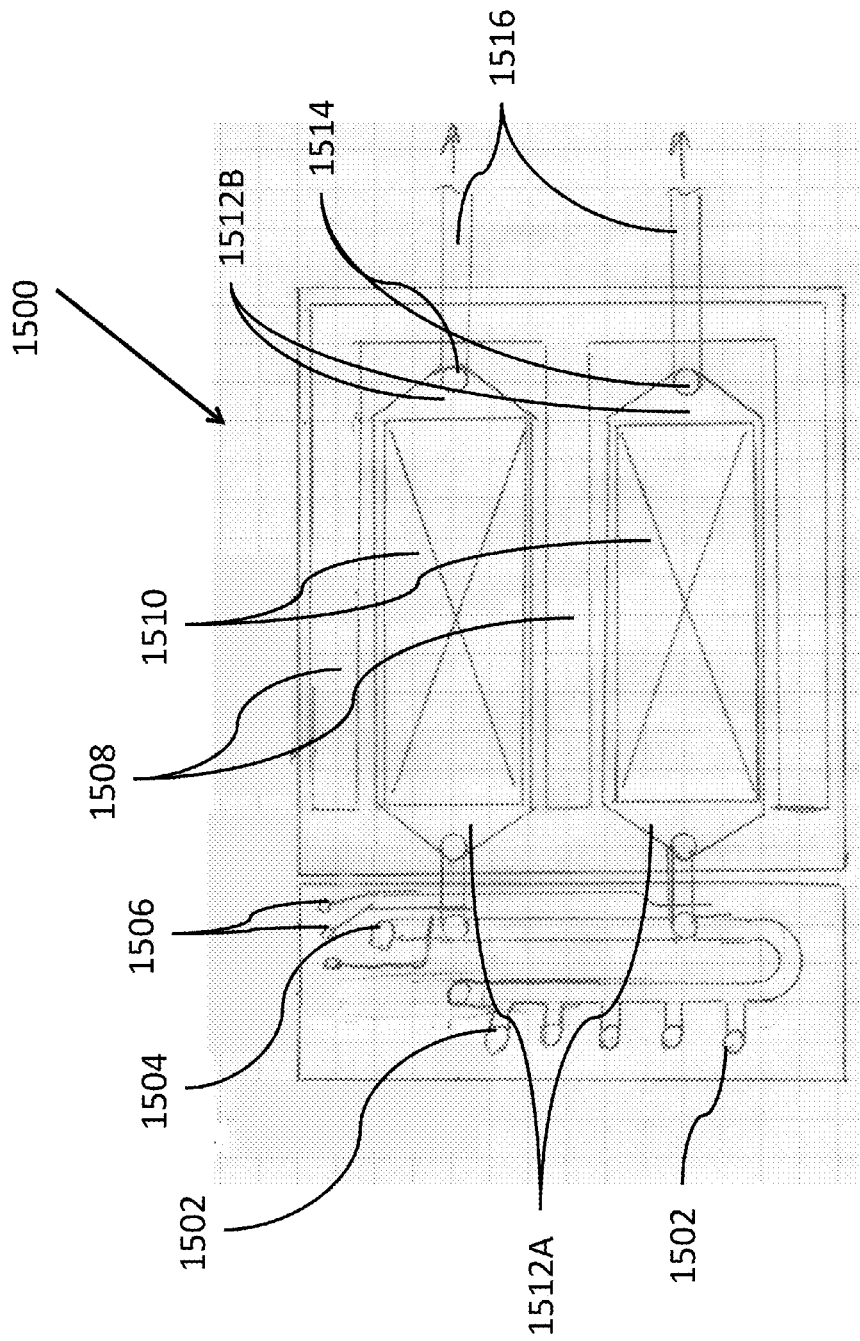
FIG. 15 schematically illustrates the valving system and interfaces for a multichannel flow cell with proximate valving control.

In one embodiment of the current invention, multiple fluidic inlets 1512A as shown in FIG. 15 may be utilized in a multiple flow cell sensor device 1500, permitting greater utilization of the chip area, and more uniform and aligned reagent flow relative to the chip and said chips readout structure. In some embodiments, samples may be introduced at different times to the different channels of the flow cell, permitting different samples to be utilized without the need for bar coding or other means for sample identification. Said multi flow cell sensor device may have multiple flow cells 1510, with an input port 1512A an output port 1512B, and a line to waste 1516, for each flow cell, and wherein each input and output port may be configured so as to optimize uniformity of flow across the sensor array within said flow cell 1510, potentially having angled side walls and or surface roughness so as to optimize said flow uniformity. Said flow cells may further be configured with valves 1504 and controls for said valves 1506 for controlling the flow of samples and or other reagents in immediate proximity to said flow cells 1510. Said samples and other reagents may be brought in using input ports 1502.

In some embodiments, said samples may be introduced different times in a process or set of processes. For example, a second sample set comprising a second set of beads which have undergone an amplification reaction and consequently have extended primers may be introduced to a channel of a flow cell associated with a chip, wherein another channel of said chip may already have a first set of beads which have undergone an amplification reaction and consequently have extended primers contained therein, and the channel with said first set of beads already contained therein may be have been exposed to a sequencing cycle, or may have been exposed to a number of sequencing cycles. In another embodiment, said second set of beads may be introduced to the same channel wherein said first set of beads may be contained. In another embodiment, wherein amplification and sequencing may be performed in a single area of an array as described elsewhere herein, a set of beads in one channel may be undergoing an isothermal amplification, while a second set of beads in another channel may be undergoing a sequencing reaction.

In some embodiments, wherein a temperature change may be needed for a first process but not for a second process, said second process may be temporarily halted or paused while the temperature change occurs, and may thence commence after the temperature is returned to the previous temperature. For example, an amplification reaction process may need to melt off and remove a second strand after primers bound to, attached to, or associated with a bead have been extended, so that an a complementary unextended primer may be hybridized to said primers which are bound to, attached to, or associated with said bead, so that a sequencing by synthesis reaction may commence. Prior to raising the temperature of the chip with multiple channels, said channel which has a set of beads which are undergoing a sequencing reaction may pause said sequencing reaction, and may actuate the co-localized virtual well electrodes such that hybridized partially extended primers are kept localized with each virtual well, while the extended primers not bound to, attached to or associated with beads in said channel wherein said amplification reaction has occurred may be dissociated from said primers bound to, attached to, or associated with said beads, and thence removed from with the channel.

The system could divide the samples over multiple fluidic channels or chips if they are too large, or combine the samples if they are combinable (for example barcoded samples). In some embodiments samples provided to the instrument would be ready for sequencing. In other embodiments samples could be processed by the instrument to generate sequencing ready samples.

Fluid Flow Control Using Electro-Wetting

In another embodiment of the current invention, utilization of multiple input ports to a single flow cell, or the use of electro-wetting may be used to introduce samples to portions of a flow cell, permitting more samples to be utilized at a time, without risk of cross contamination.

In another embodiment, an electro-wetting system may be provided to move reagents within a part of the flow cell without generating a reagent interface, thus completely preventing any mixing of reagents prior to the reagent reaching a desired portion of the flow cell, and may thus provide an extremely sharp transition in reagents.

Sharp Reagent Concentration Transitions

In some embodiments of the current invention, it may be desirable to have a sharper transition between one reagent and another, for example, when flowing a dNTP containing reagent through the flow cell wherein the sensors are positioned. This may help to provide a quicker transition between a reagent with a concentration wherein essentially zero dNTPs are present, to a reagent with a concentration at a desired dNTP for incorporation by polymerase to extend, or further extend the primer. This may enable a shorter time between a time of initiation of incorporation of a base and a time wherein a significant percentage of the primers or extended primers have had the newly introduced nucleotides incorporated into appropriate locations in different colonies in the flow cell. Said shorter time may allow a greater change in the signal level of a sensor or sensors per unit time, which may improve the signal to noise, as the noise of electronic sensors are typically subject to having noise which may include thermal noise and flicker noise, both of which can be minimized by reducing the time interval during which an integrated signal is sensed by a sensor.

This quick transition is drawn in contrast with a system wherein a slower transition occurs between a between a reagent with a concentration wherein essentially zero dNTPs are present, to a reagent with a concentration at a desired dNTP for incorporation by polymerase to extend, or further extend the primer. This slower transition may occur as a result of diffusion of dNTPs from a reagent solution containing dNTPs into a reagent solution which initially has essentially zero dNTPs, while transitioning through a long channel through which reagents are flowed prior to introduction into a flow cell wherein sensors are positioned for the detection of a sequencing reaction or another reaction. Further mixing may result from changes in channel width, corners through which the reagents must flowed, irregularities in the surface of a channel through which reagents are flowed, slow flow through channels through which reagents are brought to a flow cell, or slow flow through a flow cell.

In one embodiment of the current invention, the channel length may be substantially reduced between a point in the fluidics system wherein a transition between a reagent with a concentration wherein essentially zero dNTPs are present, to a reagent with a concentration at a desired dNTP for incorporation by polymerase to extend, or further extend the primer is generated, and the point in a fluidics system wherein said reagents are introduced into a flow cell wherein sensors for detecting a sequencing reaction may be positioned. Said channel length between the generation of a transition between said reagents and said flow cell may be a micron or less, one to five microns, five to 20 microns, 20 to 100 microns, 100 microns to 300 microns, 300 microns to one millimeter, one millimeter to three millimeters, three millimeters to ten millimeters, or ten millimeters to 30 millimeters. In general the shorter the distance between a position in the fluidics system wherein a transition between said reagents is generated and a position wherein said reagents are introduced into said flow cell, and the fewer the number of transitions in the size of flow cross section of the fluidics system, or corners in said distance, the lower the diffusion of dNTPs or other moieties will be, and thus the shorter the time frame will be between a reagent with a concentration of essentially zero dNTPs and a reagent with a reagent with a desired concentration of dNTPs at each sensor in a flow cell.

Minimizing the time for the polymerization reaction may also improve the signal to noise associated with the detection of the polymerization reaction; the noise associated with the detector is fairly consistent with time; the total integrated amount of signal generated may be the same regardless of the period of time over which it is generated. Thus reducing the time over which the data may be taken by speeding the time associated with binding of the polymerase and/or by providing a quick transition in the concentration of the dNTPs as they are introduced in a reagent slug can minimize the amount of noise which must be dealt with in analysis. As a result, the noise bandwidth which must be dealt with by the analysis software may be reduced.

Multiple Input Ports for Each Sensor Channel

In some cases, the number of dNTPs needed for incorporation may be sufficiently large that depletion of dNTPs may result in an increased time between a transition between a reagent with a concentration wherein essentially zero dNTPs are present, to a reagent with a concentration at a desired dNTP for incorporation by polymerase to extend, or further extend the primer is generated, at a sensor which is near the exit port. Lower dNTP concentrations, longer distances with more colonies in a flow cell with said colonies, larger colonies, with more primers which need to be extended by a sequencing by primer extension may all result in an increased time between a transition between a reagent with a concentration wherein essentially zero dNTPs are present, to a reagent with a concentration at a desired concentration of dNTPs for incorporation by polymerase to extend, or further extend the primer is generated, at a sensor which is near the exit port.

In some embodiment of the current invention, multiple input ports may be utilized to provide inputs to a single flow cell. If the distance between the input port and the output port is sufficiently long that there may be significant depletion or diffusion of nucleotides at the interface between a reagent with a concentration wherein essentially zero dNTPs are present, and a reagent with a concentration at a desired concentration of dNTPs for incorporation by polymerase to extend, or further extend the primer is generated, by the time the interface between said reagents reaches a sensor which is near the exit port, an additional means may be provided to introduce reagents to the flow cell.

In one embodiment, reagent channels may be provided which are above the flow cell, in additional layers of a PDMS liquid manifold. Duplicate sets of control lines, similar to those shown in FIG. 42 may be provided, which may control duplicate sets of valves, similar to those shown in FIG. 42 and flow through duplicate sets of manifolds, similar to those shown in FIG. 42, which may then provide an alternative input to the flow cell with a short distance between the point in the fluids where an interface between two reagents is created, and second or subsequent input port to the flow cell.

Synchronous Flow and Detection

A significant issue associated with next generation sequencing is the enormous quantity of data generated. Some systems can generate an average of 3000 or more data points for each useful base of sequencing data. Storing and analyzing data adds significantly to the overall cost of next generation sequencing. In some embodiments of the current invention, data reduction is performed in the simplest way, by acquiring less data. Polymerase activity can be significantly more rapid than the time needed to bring reagents with dNTPs completely through a flow cell; thus DNA colonies close to the inlet of a flow cell may have completely finished the next synthesis before the dNTPs have even reached the colonies near the outlet of said flow cell. If data is acquired for the entire flow cell during the time needed to detect reactions occurring anywhere in the flow cell, much of the data will be from regions of the flow cell where no reaction is occurring. Depending on the time needed for the dNTP reagent slug to traverse the flow cell, and the speed of polymerization, most of the colonies in the flow cell will be either waiting for dNTPs, or will have completed their synthesis reaction, rather than incorporating dNTPs and thus producing useful data.

In one embodiment of the current invention, the readout of the detector electronics is synchronized with the movement of the reagent slug through the flow cell. A reagent slug containing dNTPs may initially enter the flow cell, but not yet move far enough into the flow cell for the dNTPs to bind and incorporate with any of the colonies. At this point in time it may be possible to not take data at all. At a point slightly later in time the reagent slug will have entered the flow cell sufficiently to interact with the set of colonies in the first region. At this point in time data may be taken from the detectors associated with the colonies in a first region, but may be not taken for other regions of the flow cell. At a second point later in time the reagent slug may have entered the flow cell sufficiently to begin to interact with the set of colonies in a second region. At this point in time data may be taken from the detectors associated with the colonies in the second region, and may likely need to still be taken from the first region, depending on the speed of the reagent slug and the speed of the polymerase, but may not need to be taken for other regions of the flow cell. At a third point later in time the reagent slug has traversed through the flow cell sufficiently to begin to interact with the last set of colonies in the flow cell. At this point in time data may be taken from the detectors associated with the colonies in the last region. Some data may still need to be taken from previous regions, such as region immediately preceding said last set of colonies depending on the speed of the reagent slug, the speed of the polymerase, the length of the flow cells, and the size of the colonies, but may not need to be taken for other regions of the flow cell.

In other embodiments, time multiplexing with phase delay may be performed to distinguish different samples from each other.

As the speed of valves utilized in a system may vary, and the size of tubes, channels and ports may vary from system to system and consumable to consumable, the flow rate may also vary. In order to accommodate said variation, the first set of data taken from a system or consumable for which prior data may provide appropriate guidance as to the rate of flow in the system, more data may need to be taken, so that it may be assured that the data associated with a sequencing reaction is captured.

In one embodiment the timing of collection can be adaptively determined from an earlier column, or from data from a previous cycle of the same column. I.e. if the typical detection event is occurring near the end of the collection time an additional delay may be added before the start of the next collection period of downstream samples. Similarly if the typical detection event is occurring near the start of the collection time the next collection period for downstream samples may be started earlier.

The size of the regions is shown in the illustrations as being one colony wide, but the width of a region may be more than one colony wide. For example, if a flow cell is 1000 colonies wide from the inlet to the outlet, a region may be a one colony wide, 10 colonies wide, 100 colonies wide, 500 colonies wide, or any number in between. Thus the region from which data is acquired at a time as the reagent slug moves through the flow cell may vary from one sensor, to tens of sensors, to hundreds of sensors wide, moving with the reagent slug as it traverses the flow cell, and as the polymerization reaction completes.

The width of the region being read can be done at the time of reading the chip, preventing the need to generate and discard data. This can be done in a manner similar to that which may be utilized for reading a subarea of a CMOS image sensor, whereby a subset of the total rows or columns can be read out at a time. Depending on the device structure, it may be possible to select individual sensors, as it is possible to select individual pixels in some CMOS sensors. Alternatively, if the chip structure is designed to read out a complete row at a time, utilizing separate analog to digital converters for each column of the array of sensors; the chip may be read out selecting which subset of rows are desired. The subset of rows will change as the reagent slug progresses through the flow cell, and as areas of the flow cell complete the polymerization reaction at the colonies in said area. In some embodiments, said separate analog to digital converters of comparators associated with each column, wherein a counter may also be associated with each column, thereby allowing simultaneous conversion of the analog signal into digital signals, while allowing more time, potentially multiple orders of magnitude more time for the analog to digital conversion, with attendant improvements in signal to noise. In other embodiments, the analog to digital converters may be successive approximation devices. In other embodiments, a pixel parallel readout approach may be utilized.

The width of the data region being collected needs to be large enough to account for a variety of factors to insure that all valid data is taken. These factors include variations in flow rate of the reagent slug, which may have slower flow near the edges of the flow cell due to interactions with the surface. Other factors can include variations in the polymerization speed due to concentration of the polymerase, variations in concentration of the dNTPs, temperature variations, colony density variations, the number of repeats of the base being incorporated for a colony or colonies, amongst others. Any of these may require the width of data which is being taken to be longer.

Detection

In some embodiments of the current invention, the sensors may be NanoNeedle sensors, nanobridge sensors, ISFET sensors, ChemFETs, nanowire FETs, carbon nanotube FETs, other types of charge, conductivity, or pH detecting sensors, or a combination of different types of sensors at each sensor location wherein a bead or colony may be located for sequencing reactions. An individual sensor may detect using only a single modality such as charge, conductivity, or pH, or an individual sensor may detect using more than one modality, such as responding to both charge and pH. The sensors may provide similar information, or they provide complementary information. For example, one sensor at a sensor location may respond to changes in pH, while another sensor at a sensor location may respond to changes in conductivity. In some embodiments, one sensor may detect local changes in pH, conductivity, or charge, while another sensor is used as a reference. In one embodiment of the current invention, the reference sensor may be placed so that it does not contact any reagents, and may be used to compensate for changes in temperature, power supply voltages, internal charge injection, channel crosstalk or other electronic noise sources.

The change in charge concentration may result from other sources, including binding of DNA to DNA attached directly to the sensor, which may be either a nanobridge, a NanoNeedle, or a FET, or may result from binding of charged cDNA, RNA, proteins, lipids, carbohydrates; the change in charge may also result from an enzymatic reaction, or any other chemical reaction which may be sufficiently localized as to largely occur within the sensing region of one sensor, and within the sensing region of another sensor.

NanoNeedle

NanoNeedle Physics

In some embodiments the NanoNeedle sensor may measure the impedance change due to ions generated by a DNA polymerization event.

In other embodiments, the NanoNeedle may used to measure the impedance surface change due to the incorporation of the DNA. Each base of DNA has a negative charge. As bases are added the charge becomes more negative. This additional charge attracts positive counter-ions which can change the conductivity of the surface of the DNA coated bead. This impedance change may also result from molecules that bind to DNA. Because the charge is associated with a fixed molecule (DNA bound to bead) the local fluid environment may be changed from the polymerization condition. For example, one buffer can be used for the base incorporation and a second buffer can be used to measure the conductivity change from a previous measurement.

In some embodiments a NanoNeedle sensor may be configured to measure the impedance change of a bead as bases are added to the template DNA attached to said bead. In other embodiments, said DNA template may be attached or associated with the substrate or a coating on said substrate, or may be attached or associated with the device electrodes or coatings on said electrodes. To improve performance it is desirable to reduce the other impedances.

Defining Current Path

The sensor impedance may be dominated by other impedances. For example, the impedance of the bulk reagent between the electrodes and the Debye layer associated with the bead may be large relative to the impedance through the Debye layer associated with the bead if the physical alignment is not good between the electrodes of a NanoNeedle and a bead to which DNA is bound. If, for example, the impedance of the bulk reagent constitutes 90 percent of the total impedance between the electrodes, and the impedance of the DNA on the bead and its associated counter ions constitutes 10 percent of the total impedance between the electrodes, a one percent change in the impedance of the DNA and associated counter ions will result in a 0.1 percent change in the total impedance between the electrodes. I another example, wherein, the impedance of the bulk reagent between the electrodes may be small relative to the impedance through the Debye layer associated with the bead if the ion concentration of the bulk solution is high. If, for example, the impedance of the bulk reagent constitutes 90 percent of the total impedance between the electrodes, and the impedance of the DNA on the bead and its associated counter ions constitutes 10 percent of the total impedance between the electrodes, a one percent change in the impedance of the DNA and associated counter ions will result in an approximately 0.1 percent change in the total impedance between the electrodes.

Figure 16:
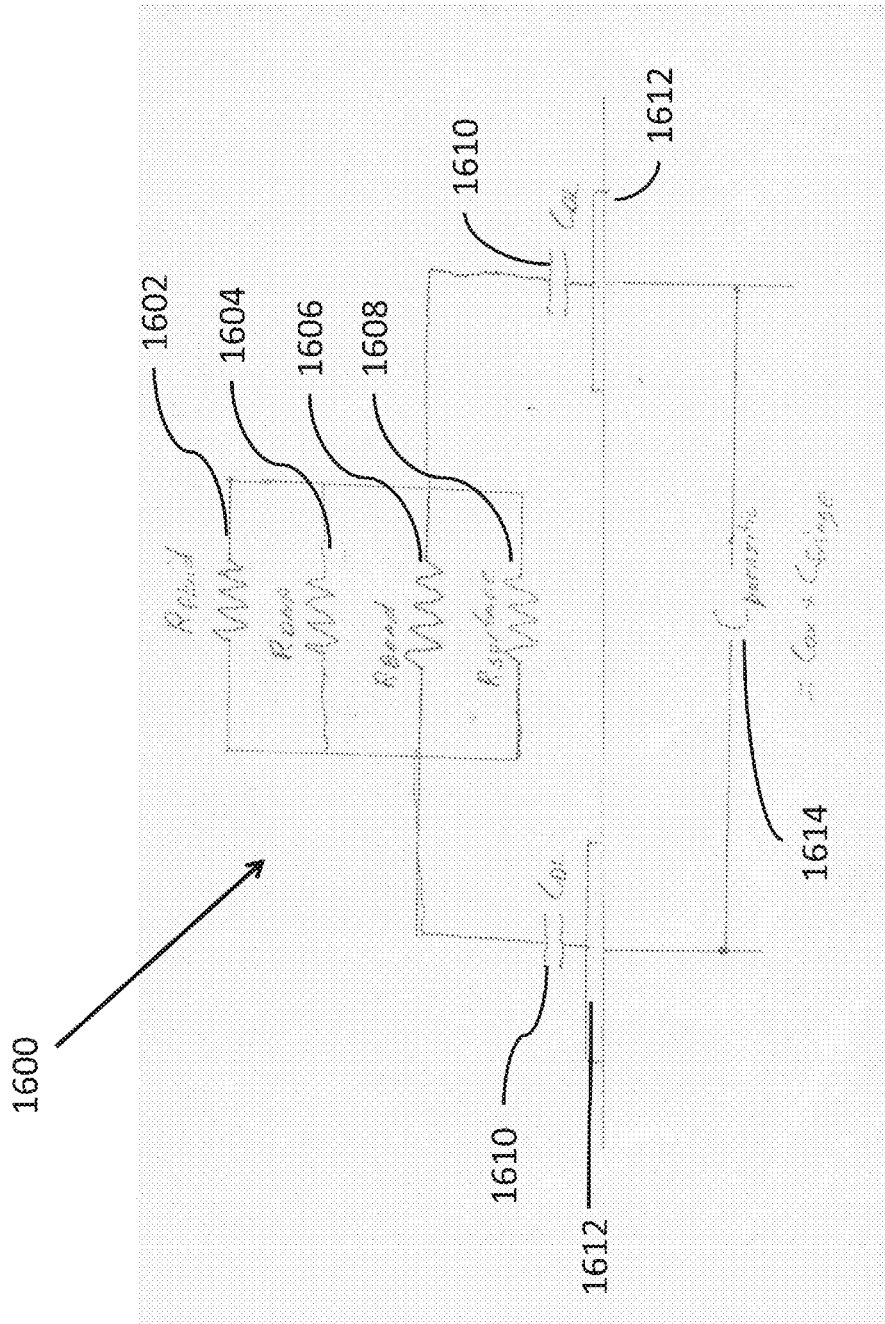
FIG. 16 schematically illustrates a simple model for the impedances in a NanoNeedle and bead array element.

FIG. 16 schematically illustrates a simplified circuit 1600 for a NanoNeedle sensor with bead. Said sensor may have parasitic capacitance 1614 and parasitic resistance (not shown). Said sensor may further have double layer capacitances 1610 associated with each electrode 1612. The resistance resulting from the counter ions associated with the DNA or other sample bound, attached or associated with the bead 1606, and may be in parallel with the resistance resulting from the bulk fluid 1602, the resistance from conductivity through the counter ions associated with charge on the surface of the bead 1606, and the resistance from conductivity through the counter ions associated with charge on the surface of the sensor 1608. Additional portions of the circuit that may add complexity include resistances (not shown) between the double layer capacitance 1610 and the resistance from conductivity through the counter ions associated with charge on the surface of the bead 1606, and the resistance from conductivity through the counter ions associated with charge on the surface of the sensor 1608.

Thus in some embodiments, it is desirable to minimize the distance between both electrodes and the bead. In other embodiments, it may be desirable to measure the counter ions from as much of the bead as possible, allowing averaging from as much of the entire surface of said bead as possible. In some embodiments it may be desirable to position said electrodes at opposite sides of said bead, allowing current to flow over the entire surface of said bead in as even a manner as possible. In other embodiments, it may be desirable to utilize electrodes which are not as small as might be possible, so that the current density of the current path emitting from said electrodes is not significantly higher than the current path at the point in the current path wherein the current density is smallest. For example, if an electrode could be made infinitely small, the current density emanating from said infinitely small electrode would be infinitely large. In another example, wherein the electrodes comprise spherical caps at opposite ends of said bead, and the circumference of the circle formed by the spherical cap is one half of the length of the great circle of said bead, then the maximum current density will be twice as high at the spherical cap as it is at the great circle midway between the spherical caps. In some embodiments the ratio of maximum current to minimum current over the surface of the bead may be 2 to 1; in other embodiments, the ration of maximum current to minimum current over the surface of the bead may be between 2 to 1 and 3 to 1, between 3 to 1 and 4 to 1, between 4 to 1 and 6 to 1, between 6 to 1 and 9 to 1, between 9 to 1 and 15 to 1, between 15 to 1 and 30 to 1, or between 30 to 1 and 100 to 1.

In some embodiments wherein the electrodes may be fabricated utilizing semiconductor technologies, and wherein the area of said electrode adjacent to said bead may be of a height equal to the thickness of the electrode, it may be desirable to hold the electrode a small distance from said bead. Said small distance may be from 0.1 Debye lengths, to 0.3 Debye lengths, from 0.3 Debye lengths, to 1.0 Debye lengths, from 1.0 Debye lengths, to 3.0 Debye lengths, from 3.0 Debye lengths, to 10.0 Debye lengths, or from 10.0 Debye lengths, to 100 Debye lengths. Said Debye length is considered to be an additive combination of the Debye length of said bead and said electrode. In some embodiments wherein the electrodes may be fabricated utilizing semiconductor technologies, and wherein the area of said electrode adjacent to said bead may be of a height equal to the thickness of the electrode, it may be desirable to utilize an electrode with a length which may be a fraction of half the length of the circumference of the great circle of said bead. Said fraction of half the length of the circumference of the great circle of said bead may be from 0.01 to 0.03 of the length of half the length of the circumference of the great circle of said bead, from 0.03 to 0.1 of the length of half the length of the circumference of the great circle of said bead, from 0.1 to 0.3 of the length of half the length of the circumference of the great circle of said bead, from 0.3 to 0.75 of the length of half the length of the circumference of the great circle of said bead.

In some embodiments, a combination of maintaining a distance between said electrode and said bead, and fabricating said electrode so that said electrode a fraction of the length of half the length of the circumference of the great circle of said bead may be utilized.

Minimizing Alternative Paths

In some embodiments, it may be desirable to reduce the current passing through the bulk reagent, in order to maximize the portion of the measurement current which passes through the counter ions associated with DNA bound to, attached to, or associated with a bead. As a result, in some embodiments, it may be desirable to physically reduce the volume of bulk reagent in proximity to said bead, such that the impedance contribution from said DNA counter ions may be maximized. In other embodiments, it may be desirable to minimize the surface area of the structure which may retain said bead in proximity to said electrodes for measurement of said DNA counter ions. In a further embodiment, it may be desirable to minimize the zeta potential of the bead and or surface(s) of the structure which may retain said bead in proximity to said electrodes for measurement of said DNA counter ions.

Sensor Array

The NanoNeedle structures may fabricated in an array of NanoNeedles, permitting large numbers of single DNA molecules to be sequenced at the same time.

Figure 17:
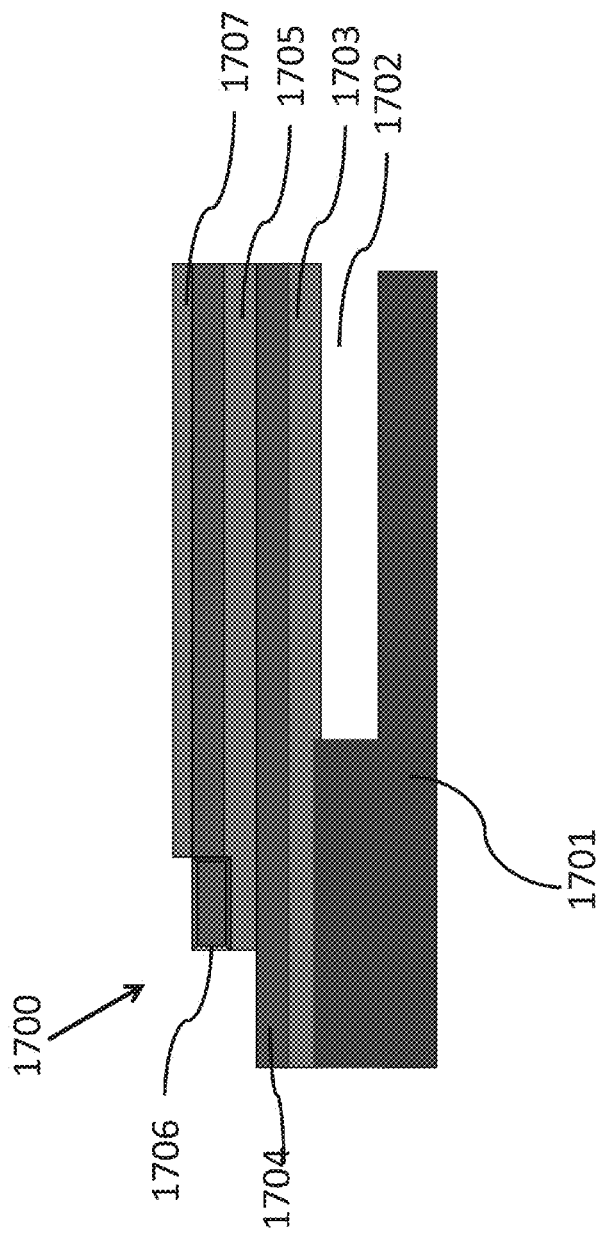
FIG. 17 schematically depicts an under-etched stacked NanoNeedle.

As shown in FIG. 17 a NanoNeedle sensor structure 1700 may be fabricated with a Silicon substrate 1701, and may have a 800 nm deep channel 1702 etched in said substrate. A silicon oxide layer of 200 nm thickness 1703 may be fabricated on the substrate, followed by a conductive p+ silicon layer of 80 nm thickness 1704, followed by a silicon oxide layer of 30 nm thickness 1705, followed by a conductive p+ silicon layer of 80 nm thickness 1706, followed by a silicon oxide layer of 20 nm thickness 1707. The channel may be created after the structure is fabricated. The structure may be generated such that an oxide layer or a resist layer covers all sections which may be to be retained in the final structure. A chemical wet etch, a plasma etch, or a vapor phase etch may be utilized to remove the silicon or other similar substrate from under the structure. The conductive tip of the structure may then be exposed using an ion milling step.

Figure 18:
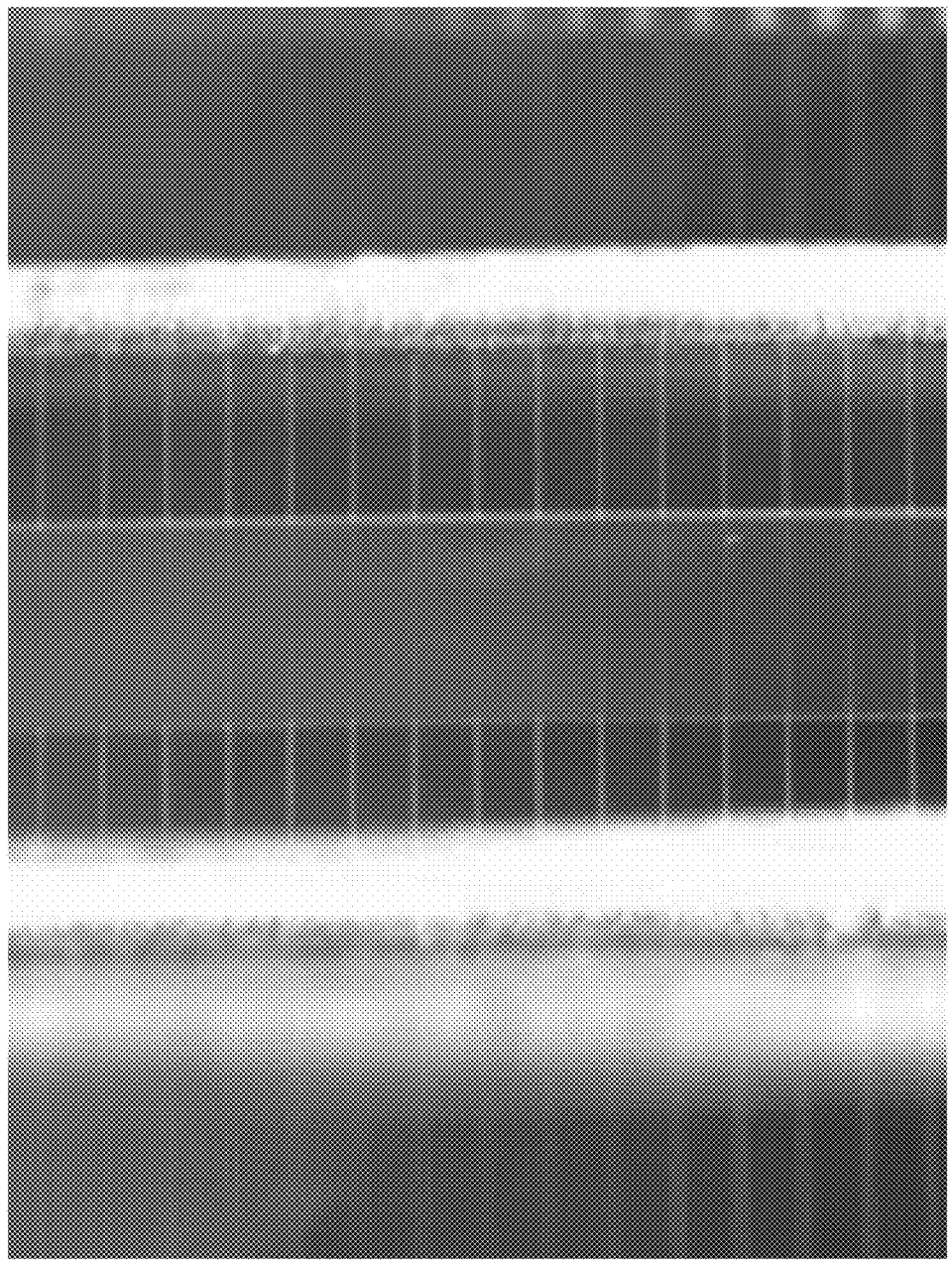
FIG. 18 is a photomicrograph of an array of under-etched stacked NanoNeedles.

All of the thicknesses may be varied, as may the materials. The channel in the substrate may alternatively be fabricated using an oxide layer, with a resist layer in the volume of the channel. The layers of Oxide and conductors may then be fabricated on top of the oxide and resist, obviating the need to under-etch the structure. FIG. 18 Illustrates a single ended NanoNeedle array fabricated in a manner similar to that schematically depicted in FIG. 17.

Figure 19:
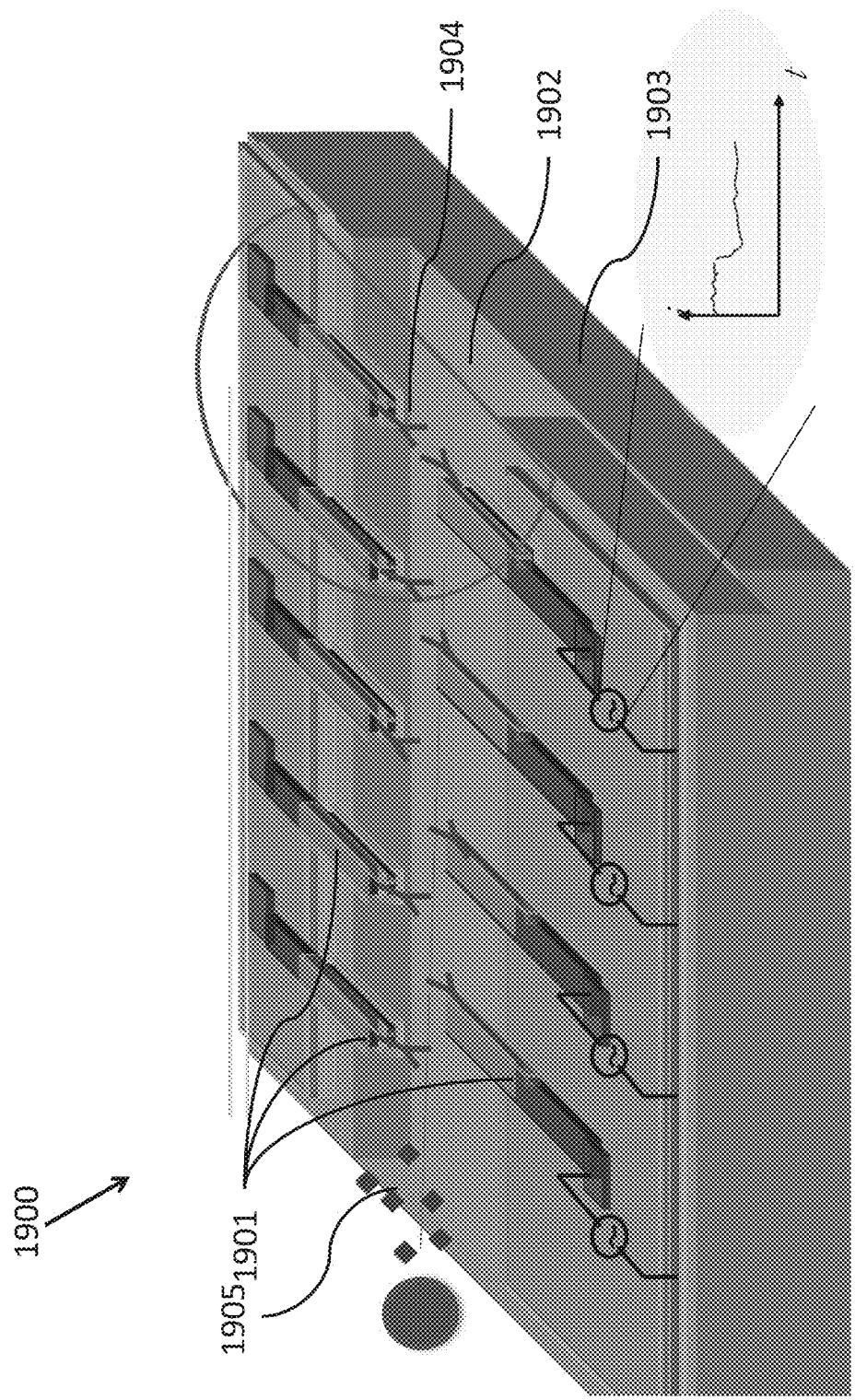
FIG. 19 schematically depicts a 2D array of under-etched stacked NanoNeedles.
Figure 20:
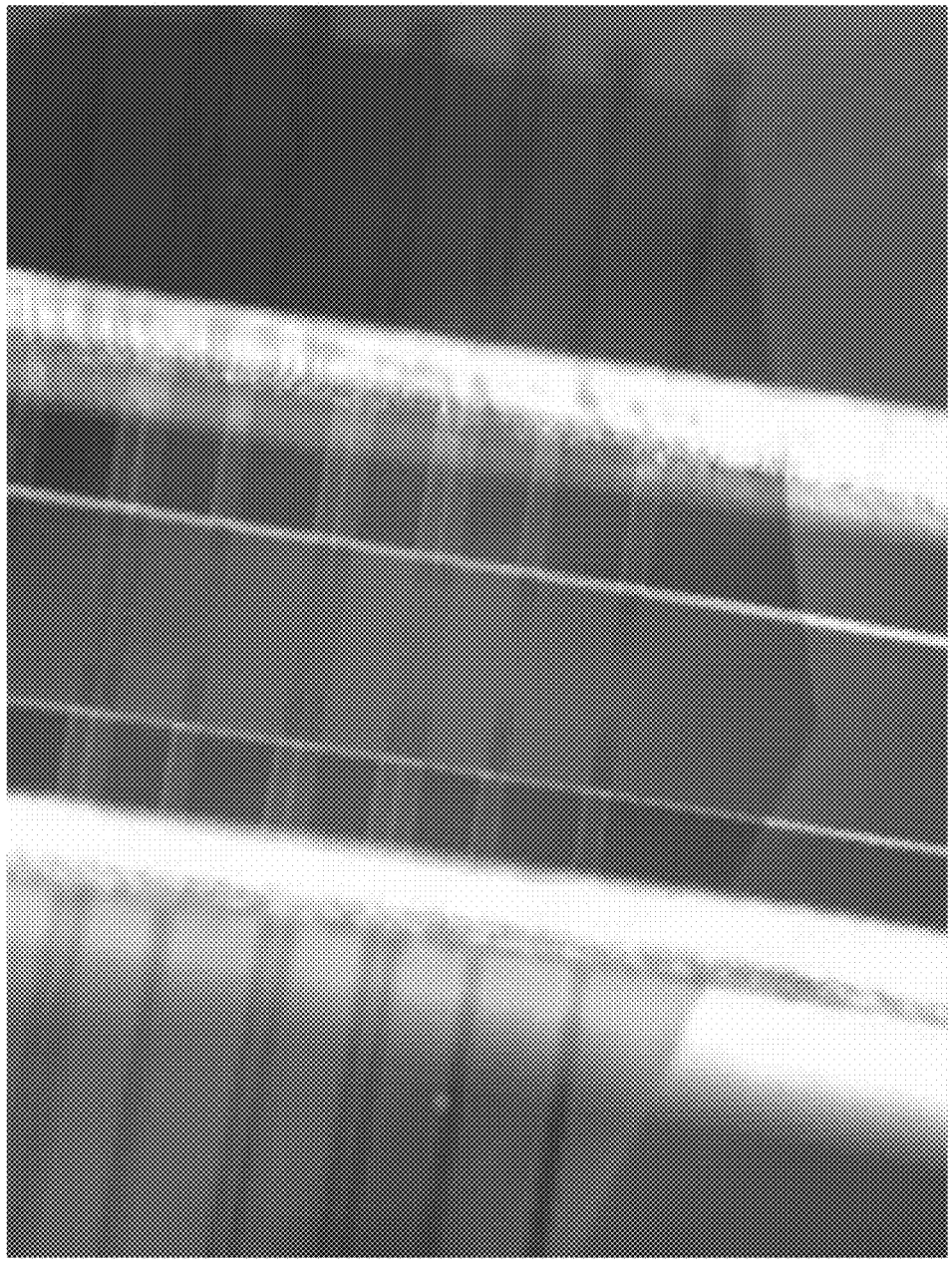
FIG. 20 is a photomicrograph of a 2D array of under-etched stacked NanoNeedles.

As shown in FIG. 19 such a structure may have sensors 1901 on both sides of a channel 1902 formed in a substrate 1903. Polymerase and or target DNA 1904 may be attached to the active area of the sensor. The sensor itself may be used to electrophoretically and or dielectrophoretically localize the polymerase and or target DNA to the active area of the sensor. The target DNA may be a single double stranded, single stranded DNA target, or a circularized DNA target, or a local amplification may be done in place on the active area of the sensor, as described in PCT/US2011/054769 FIG. 20 Illustrates an interdigitated NanoNeedle array fabricated in a manner similar to that schematically depicted in FIG. 19.

Nucleotides or probes 1905 may be then be provided, and a sequencing by synthesis process may thence be effectuated.

To improve the sensitivity of either the NanoNeedle or the NanoBridge, a local amplifier may be provided. In some embodiments, an amplifier may be used with one amplifier circuit for each sensor or with multiple sensors sharing the same amplifier. In other embodiments, some amplification may be associated with each sensor, and additional amplification and or other associated circuitry may be shared or multiplexed between different sensors. The sensor can be fabricated as a narrow structure, and can be etched under the structure so that both sides may be accessible to changes in pH, or to changes in conductivity. The surface of the device may rough, permitting greater surface area for binding of sample molecules. The surface associated with the electrodes of a NanoNeedle may be gold or platinum, or may be platinum black, iridium oxide, or Ppy/PSS to increase the surface area and the associated double layer capacitance.

Electric concentration of ions may be effected, concentrating the DNA, polymerase, primers nucleotides and other reagents as needed to the active area of the NanoNeedle or NanoBridge sensor. Said concentration allows much more of the sample to be attached or associated with each sensor, mitigating the need for whole genome amplification.

Zeta Potential Reduction

Another factor which may prevent optimal measurement of the impedance of said DNA on said bead includes counter ions which result from the Debye layer associated with the zeta potential of the surface of the bead and or the counter ions which result from the Debye layer associated with the zeta potential of the surface of the sensor. Said counter ions which result from the zeta potential(s) associate(d) with the surface of said bead and or the surface of said sensor may result in a current which may be in series and or in parallel with the desired current associated with counter ion of said DNA on said bead. Further, as the zeta potential varies, the Debye length and the number of associated counter ions may vary concordantly. Said zeta potential may vary with changes in buffer conditions including changes in pH, salt concentration and various other factors. Said concordant variation may thus confuse measurements of the said DNA on said bead. Thus it may be desirable to both minimize the zeta potential, and to minimize variations of zeta potential with variations in buffer conditions.

In some embodiments, the sensor may be fabricated utilizing silicon. Silicon dioxide has a significant zeta potential magnitude at pHs typically useful for polymerization activity, such as pH 7 to 9; but the zeta potential magnitude of silicon nitride is significantly less than that of silicon dioxide. Thus in some embodiments, it may be preferable to utilize silicon nitride at the interface between the silicon sensor device and any reagents which may come into contact with said silicon sensor device in order to minimize the zeta potential and concomitant current through counter ions which may be in the associated Debye layer.

In some embodiments, a coating which may be applied over the surface of the sensor, wherein the sensor may be fabricated of silicon, silicon dioxide, PDMS, Topaz™ or other various polymers or combinations thereof, wherein said electrode and or coating may comprise materials such as $TiO^2$, $ZrO^2$, or Indium Tin Oxide, $BaTiO^3$ wherein the zeta potential and the resulting Debye layer may be significantly reduced. In other embodiments, surface coating(s) such as PEG (Poly Ethylene Glycol), PTFE, poly-L-lycine, acrylate, methyl cellulose, n-dodecyl-B-D-maltoside, acrylamide, fluorinated alkane chains, or other cross-linked or partially cross-linked polymers may be utilized to modify the zeta potential, or combinations of surface coatings may be utilized to similarly minimize the zeta potential and concomitant Debye length. In other embodiments the zeta potential magnitude can be reduced by protecting the silanol groups with a compound such as trimethylchlorosilane which decreases the number of ionizable silanol groups.

In some embodiments of the current invention, it may be desirable to reduce the zeta potential of a bead on which DNA to be sensed is attached, thereby reducing the concomitant current resulting from counter ions associated with the surface of said bead due to said zeta potential. Thus in some embodiments it may be desirable to fabricate the bead of a material with a low zeta potential at the pH levels anticipated for effective polymerization, or the bead may be coated with a material with a low zeta potential at the pH levels anticipated for effective polymerization, such as such as PEG (Poly Ethylene Glycol), PTFE, poly-L-lysine, acrylate, methyl cellulose, n-dodecyl-B-D-maltoside, acrylamide, fluorinated alkane chains, or other cross-linked or partially cross-linked polymers may be utilized to modify the zeta potential, or combinations of surface coatings may be utilized to similarly minimize the zeta potential and concomitant Debye length.

$CO_2$ Removal

In some embodiments of the current invention, it may be desirable to minimize variations in pH which may result from buffer reagents which may be used as part of an assay, while it may be simultaneously desirable to minimize ionic concentration. As a result, it may be desirable to use reagents with little buffering capacity while maintaining a fixed pH. Buffers may in some cases be degassed as part of an assay or method; said buffers may then be subject to changes in pH as $CO_2$ dissolves into the buffer reagent. In some embodiments, it may be desirable to restrict the interaction between $CO_2$ and buffer reagents. Thus it may be desirable to exclude atmospheric gases, and to provide other gases which do not include $CO_2$ such as Nitrogen, Argon, or other purified gases, or mixtures of gases which do not contain $CO_2$ or other gases which might otherwise dissolve into said reagent buffer, and thus change the ion concentration and or pH.

In some embodiments of the current invention, an external gas source such as an industrial gas cylinder may be utilized. In some embodiments said gas cylinder may be external to an instrument wherein the fluidics resides. In other embodiments, said industrial gas cylinder may be placed within a compartment within the instrument. In other embodiments, a $CO^2$ scrubber/degasser/debubbler may be utilized such as a regenerable metal oxide system, a Kraft process system, an activated carbon system, a membrane system which may utilize a membrane such as the Systec AF® or Poridex™, or other $CO_2$ scrubber/degasser/debubbler system may be utilized. Said $CO_2$ scrubber/degasser/debubbler may be built within said instrument, or may be external to said instrument.

NanoNeedle Bead in Depression

In some embodiments of the current invention, it may be desirable to bring the sensor electrodes for a sensor such as a NanoNeedle sensor into close proximity to a bead, in order to minimize the amount of bulk reagent volume which may be between the NanoNeedle electrodes and the bead or particle. One embodiment of the current invention may have a bead held in a depression as shown in FIGS. 2A, 2B and 2C. The depression may be formed of a material which is deposited on a substrate, and the material forming the depression may have a pair of NanoNeedle electrodes formed upon said material, wherein the electrodes may be formed in an arc conforming to the edge of the depression, and thus to the edge of the bead. In some embodiments said depression may be fully accessible to fluids on one side, or two sides, or said depression have a width to depth ration of less than 1.0, or may have a width to depth ratio of 1.0 to 0.9, 0.9 to 0.8, 0.8 to 0.7, 0.7 to 0.6, 0.6 to 0.5, 0.5 to 0.4, 0.4 to 0.3, 0.3 to 0.2, 0.2 to 0.1 or 0.1 to 0.01.

In some embodiments, the depression may minimize the volume of reagent in proximity to said bead. Said depression may be shaped so as to conform to the shape of said bead, whereby the bottom of said depression may be narrower than the cross section of said depression at the height of said electrodes. In other embodiments, said electrodes and or sensor area may be covered by a layer of additional material, such that the effective depth of said depression may be greater than half the diameter of said bead, further reducing the volume of bulk reagent proximate said bead.

Electrodes Conforming to Bead Shape

The electrodes may thus be touching the surface of the bead, or may be within the Debye length of the surface of the bead or particle and the DNA attached or bound thereto. In some embodiments, the electrodes may be curved such that said electrodes follow a curve with a radius similar to the radius of the bead, permitting better coupling between said electrode and said bead. Such a device permits a minimum influence on the total impedance between the NanoNeedle electrodes by the bulk reagent solution, and a maximum influence by the DNA attached to or bound to the surface of the bead or particle or the counter ions near the DNA.

In some embodiments of the current invention, a NanoNeedle may have the active area of the sensor shaped to fit a bead or other sample retaining mechanism. It may, for example be shaped in an arc, with the curve of the arc oriented so as to align with the curve of a bead. It may also have one NanoNeedle of a NanoNeedle pair configured such that it is offset or "shorter" than the other NanoNeedle of said NanoNeedle pair, such that the inner radius of the arc has a larger diameter, and the same centroid. Said offset may permit an increase in the volume of the sensing region associated with the NanoNeedle pair, and may further change the orientation of the field associated with the sensing region and thus orientation of the sensing region, so that the sensing region is more oriented towards the center of the bead, rather than parallel to substrate.

In an alternative embodiment as shown in schematic side view FIG. 21A and schematic top view FIG. 21B, one electrode 2105 may be attached directly to the substrate 2102 or on another layer upon said substrate, allowing isolation from said substrate. The second electrode 2105 in the NanoNeedle may be attached upon a dielectric 2113 portion of the sensor which is utilized to position the bead or particle 2101 in a fixed location. The bead or particle 2101 is thus in contact with both electrodes 2101, 2105, minimizing the influence of the bulk reagent solution on the total impedance between the NanoNeedle electrodes, as opposed to the impedance resulting from the counter ions within the Debye length associated with the bead or particle and the DNA which is attached or bound to the bead or particle.

In some embodiments, one or both electrodes may be fabricated such that said electrodes may conform to the curve of said bead so as to provide a lower and more regular impedance between said electrode(s) and said bead. Said curvature may abut the edge of a depression, or may be slightly farther from said the edge of said depression so as to allow a larger area of interface and a lower current density.

In a further embodiment as shown in FIG. 21C, the bead or particle 2101 may be held in place on a substrate 2102. A first electrode 2105A of a NanoNeedle 2100 may be attached directly to the substrate 2102, or to an adhesion layer (not shown) adhered to said substrate 2102. A dielectric layer 2114 may then be fabricated so as to cover said first electrode 2105A. A second electrode 2105B of a NanoNeedle 2100 may then be fabricated above the dielectric 2114 and said first electrode 2105A of the NanoNeedle 2100. The second electrode 2105B may be shorter, so as to conform to the curve of the bead or particle. The difference in the length will be a function of the diameter of the bead or particle 2101, and the thickness of the two electrodes 2105 and the dielectric 2114 between the electrodes 2105. In this manner the electrodes 2105 may be in contact with the bead or particle 2101, or may be in very close proximity to the bead or particle 2101, such that the impedance resulting from the counter ions within the Debye length associated with the bead or particle 2101 and the DNA which is attached or bound to the bead or particle 2101 is greater than the impedance of the bulk reagent.

In a further embodiment, said electrodes may be fabricated such that said electrodes do not abut the edge of a depression, but may be instead fabricated a short distance from said edge such that the current density in immediate proximity to said electrode may be reduced.

In FIG. 22A, a NanoNeedle 2200 is schematically illustrated in a side view wherein said NanoNeedle 2200 has electrodes 2205 on each side of a depression in a dielectric 2203, wherein a bead 2201 may be retained on a substrate 2202, and metalization 2204 to said electrodes 2205 may be utilized. As shown in FIG. 22A, the dielectric material 2203 may be similar in thickness to one half the diameter of the said bead 2201, and the depression width may be slightly larger than the diameter of said bead 2201 while still allowing said bead 2201 to be with the Debye length of said bead 2201 with respect to both electrodes 2205. Said thickness of the dielectric 2203 may of a thickness which permits retention of the bead 2201, and maintains said bead 2201 within a Debye length of said bead 2201 of both electrodes 2205.

In FIG. 22B, a NanoNeedle 2200 is schematically illustrated in a side view wherein said NanoNeedle 2200 has electrodes 2205 on each side of a depression in a dielectric 2203, wherein a bead 2201 may be retained above a substrate 2202, and metalization 2204 to said electrodes 2205 may be utilized. As shown in FIG. 22A, the dielectric material 2203 may be less than one half the diameter of the said bead 2201, potentially said dielectric material 2203 thickness may be one quarter to one third the diameter of said bead, and the depression width may be less than the diameter of said bead 2201 such that said bead 2201 may be suspended above said substrate 2202. Said close proximity of said bead 2202 and said electrodes 2205 maintains a spatial proximity between said bead 2202 and said electrodes 2205 such that said bead 2201 is within a Debye length of said bead 2201 of both electrodes 2205.

In FIG. 22C, a NanoNeedle 2200 is schematically illustrated in a top view wherein said NanoNeedle 2200 has electrodes 2205, which are curved to maintain close proximity to said bead as a result of said depression in said dielectric material 2203 being smaller in diameter than the diameter of said bead 2201, such that said bead is held in immediate proximity over an arc corresponding to the point of contact or close proximity between said bead 2201 and said electrodes 2205.

Figure 22D:
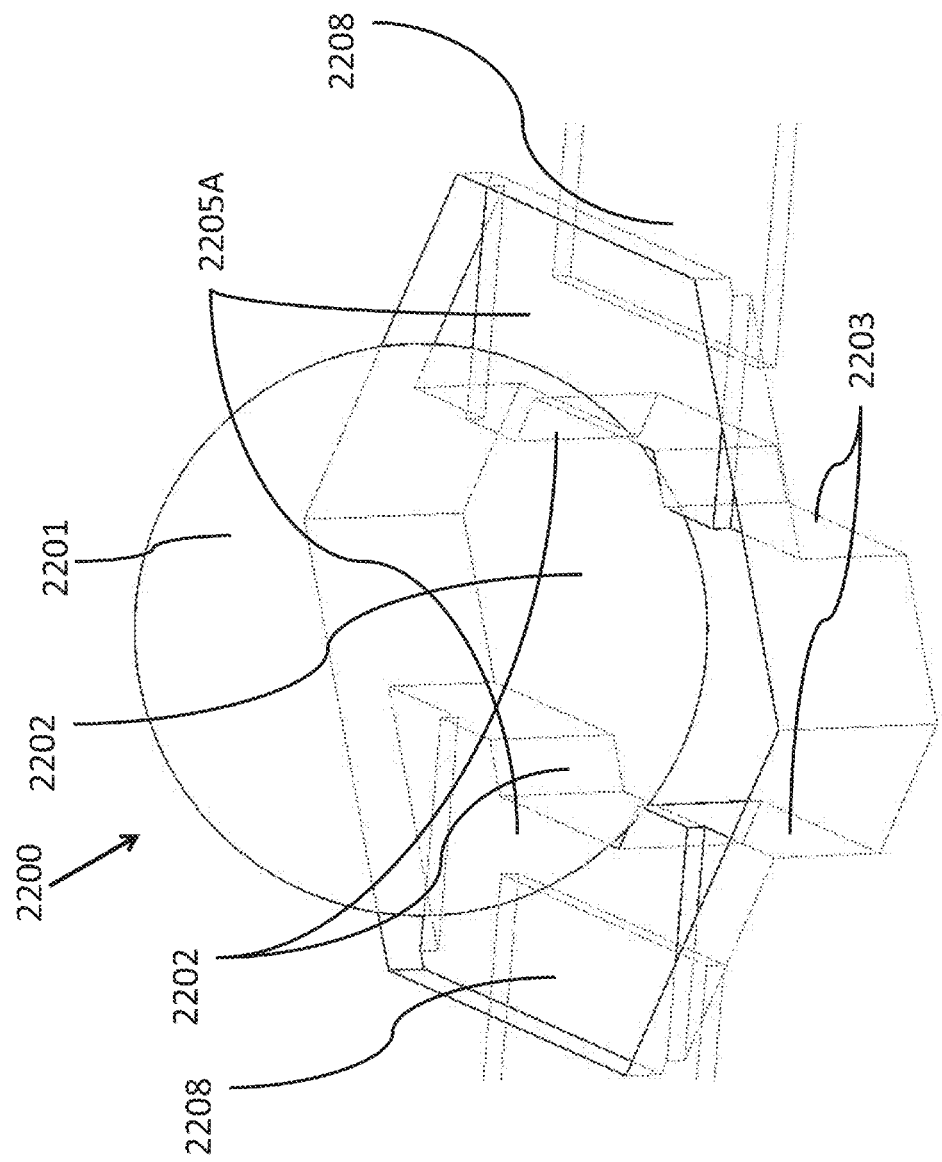

FIG. 22D is a three transparent dimensional drawing of a NanoNeedle structure 2200 similar to that of FIG. 22B and FIG. 22C, but with substantial fluidic access to said bead 2201. Said bead 2201 is held suspended above said substrate 2202, and is instead held against electrodes 2205A, which are fabricated above said dielectric material 2203, wherein said electrodes 2205A and dielectric material 2203 are shaped to be within a Debye length of said bead 2201 Debye length, but is not curved to match the curvature of said bead 2201, such that instead of having a line contact between said bead and said electrode 2205 and or dielectric material 2203, there are three or four point contacts between said bead 2201 and said electrode or dielectric material 2203. FIG. 23D also depicts magnets 2208 which apply the force to retain said bead 2201 in place in the NanoNeedle structure 2200.

A NanoNeedle may be configured to be in a double spiral or serpentine pattern, in order to increase the length, and simultaneously decrease the width of the nanobridge channel. A sensing region which is too wide in the sensing region will have a comparatively low impedance in the sensing region, and may have areas of the sensing region which have smaller changes in local charge density than other regions, for example, at the edges of a bead in comparison with the center of a bead. Said sensing region which is "too wide" may thus also have smaller changes in impedance, as only a portion of the sensing region may be significantly affected by a binding or reaction which results in a local change in charge. In contrast, a NanoNeedle which is too long and thin may have an impedance that is so large that any current change may be too small to sense with good signal to noise. Thus the width and length of the channel associated with a nanobridge sensor will need to be tuned for the specific application for which said nanobridge sensor is intended.

NanoNeedle Reduction of Streaming Potential Effect

Streaming potential was originally observed by Quinke in 1859, and is a well known phenomenon in capillaries; it is a function of the flow rate, the zeta potential, and the conductivity of the fluid, amongst other factors. Thus a voltage may be impressed on a NanoNeedle, and variations in the flow rate or distances between electrodes may result in variations either spatially or temporally in the bias impressed on a NanoBridge.

In other embodiments it may be desirable to orient NanoNeedle electrodes parallel to the flow of the fluid, so that there will not be a potentially variable streaming potential impressed between the electrodes of the NanoNeedle, as would be the case if said electrodes were orthogonal to the flow of said fluid.

Capacitive Coupling

In some embodiments of the current invention, the NanoNeedle may be coupled with a local capacitor, or capacitor, associated with one or both electrodes, in order to prevent influence from DC bias levels from the driver circuit or leakage from within the chip sensor from influencing the output signal.

NanoBridge

Figure 23:
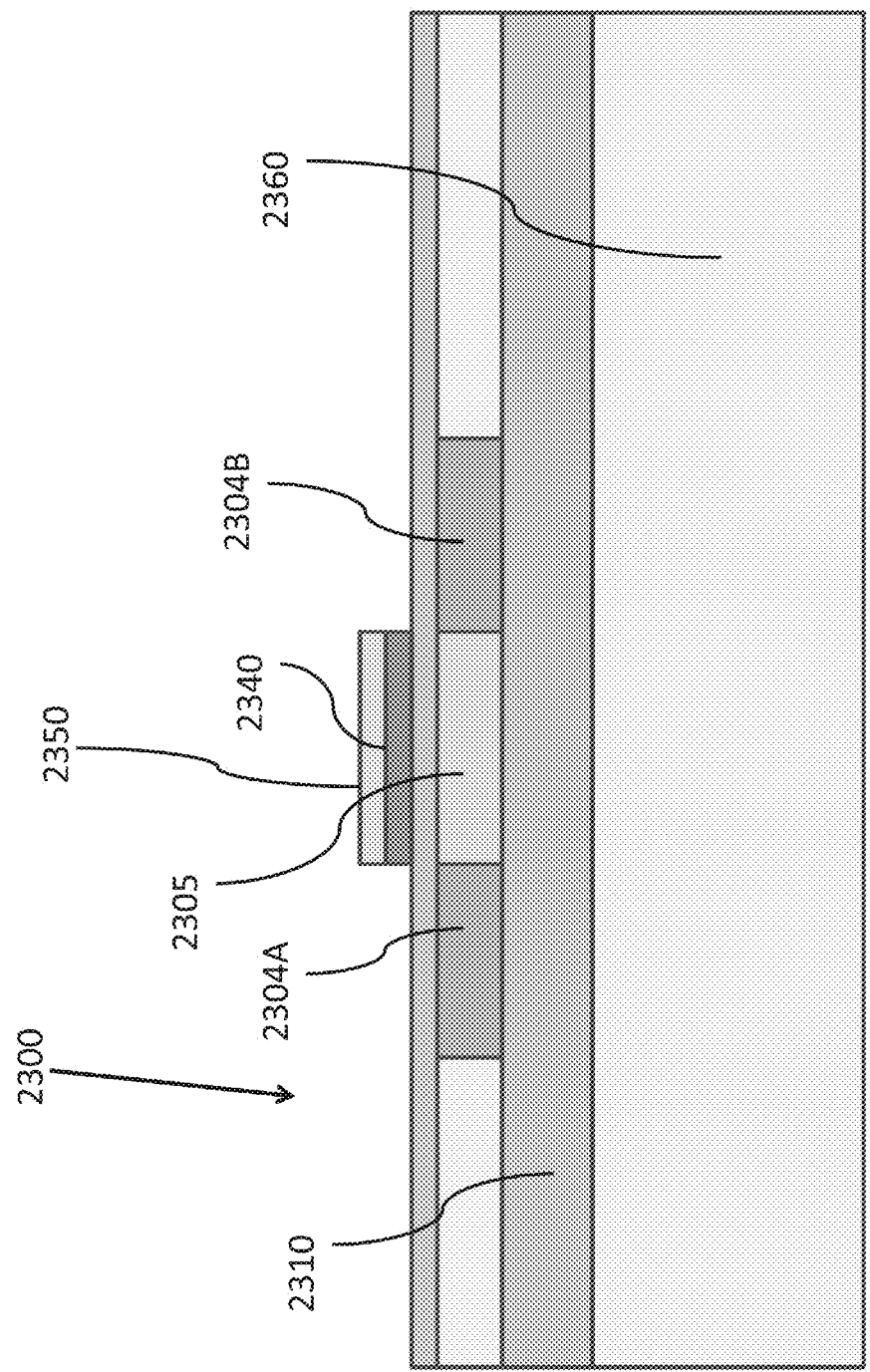
FIG. 23 schematically depicts the elements of a NanoBridge.

In a further alternative embodiment, a Nanobridge sensor structure 2300 as shown in FIG. 23 may be utilized instead of the aforementioned NanoNeedle sensor. The Nanobridge sensor may be utilized in the same manner as the NanoNeedle, including utilizing circularized or linear DNA, a linear or hairpin primer, a polymerase as described for the nanobridge, and may fabricated as an array.

Said NanoBridge sensor structure 2300 may comprise a silicon-on-insulator device, comprising a substrate 2360, a dielectric insulator 2310, two higher doped semiconductor regions 2304A and 2304B, a lower doped semiconductor active area region 2305, a further metalization layer 2340 which may cover said semiconductor active area region 2305, and which may have a further dielectric coating 2350 over said semiconductor active area region 2305.

NanoBridge Physics

In some embodiments, the nanobridge may sense local changes in charge. Changes in surface charge of a surface of the nanobridge which abuts the flow cell may result from changes in charge in the second layer of the double layer in the flow cell in said surface of the nanobridge abutting the flow cell. These changes in charge on the surface of the nanobridge may then change the charge distribution in the nanobridge, and thus change the conductivity of the nanobridge. The area of the nanobridge surface which has charge changes may thus have changes in conductance in the associated volumes of the nanobridge, while other surface areas of the nanobridge may not have changes in surface charge, and thus may not have changes in conductance in the associated volumes thereof. Depending on the type of semiconductor material the nanobridge is constructed of (n or p type), the amount and uniformity of doping in the nanobridge semiconductor material, and the sign of the charges (positive or negative) on the surface of the nanobridge, and whether the change in charge is an increase or decrease in the amount or density of surface charge may increase or decrease the conductance.

In some embodiments, a change in the charge on a bead located above or proximate such that the bead is located within the Debye length may cause a corresponding change quantity or concentration of charge locally present in both of the layers of the double layer. Said change in the quantity of charge relates directly to the local ion concentration, and thus also to the surface layer capacitance, and the conductance of the reagent within the Debye length. Said change in the charge may be either an increase, or a decrease depending on the relative charge of the surface layer and the charge change on a bead.

In some embodiments for sequencing of a clonal beads a Nanobridge sensor may be utilized. The method of use of the Nanobridge sensor may be considered to be the same as that utilized by NanoNeedle, with all of the advantages of the NanoNeedle.

In an alternative embodiment, the nanobridge may be utilized to detect a local temperature change, wherein the Nanobridge sensor acts in part as a temperature sensor.

NanoBridge as pH or Temperature Sensor

In an alternative embodiment the Nanobridge can be configured to operate as a temperature sensor and/or a pH sensor to detect nucleotide incorporations. This method is further described in US patent application 20080166727 titled "Heat and pH measurement for sequencing of DNA, which is hereby incorporated in its entirety.

The present invention provides methods and systems for polynucleotide sequencing based upon pH and/or temperature detection. In some embodiments, the system and method may employ dyes or quantum dots that allow visual or optical detection of pH and/or temperature changes. This monitoring may allow monitoring of the bulk solution, or may allow local monitoring of the volume associated with each colony, or may allow for monitoring of both the bulk solution and the volume associated with each colony.

Under Etched NanoBridge

In other embodiments of the current invention, an array of NanoBridge sensors may be etched underneath, so as to further minimize the channel size, and to maximize the surface area which may interact with the charge resultant from the DNA sequencing reaction. In other embodiments, said array of NanoBridge sensors may not be etched underneath, or may be partially etched so as to provide a more robust structure. In yet further embodiments of the current invention, said array of NanoBridge sensors may be configured such that it is arranged in a comb configuration, with sensors interleaved between each other from both sides, with potential features, such as a potential amplifier arranged alternatively on one side, and then the other. In another embodiment of the current invention, said array of Nanobridge sensors may be arranged such that potential features, such as a potential amplifier, are all arranged on one side of the sensor array.

Shaped NanoBridges

In some embodiments of the current invention, a nanobridge sensor may be configured such that the width and length of the sensing channel may varied to better align with optimal sensitivity for a sensing application; said variations may relate to the spacing and size of a sample region, the charge associated with sensing the desired moiety, and the impedance of the nanobridge in nonsensing regions, such as conductive portions of the nanobridge between the sensing region and a local amplifier, or other associated impedances.

Figure 24A:
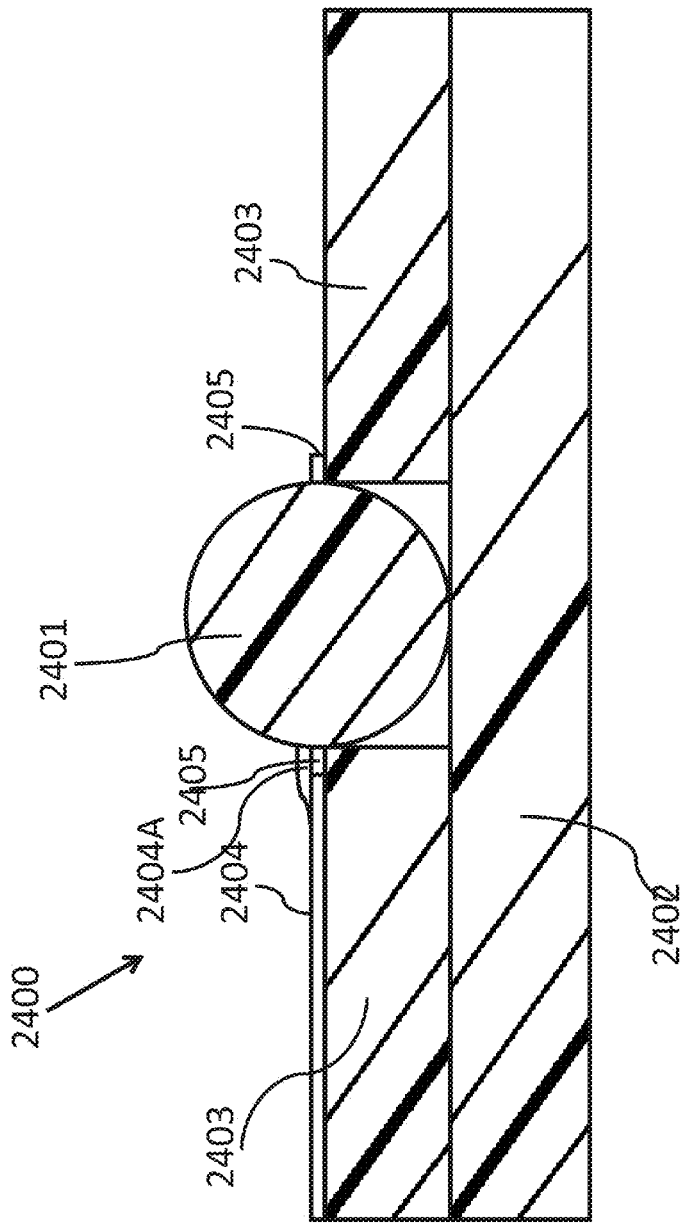
Figure 24C:
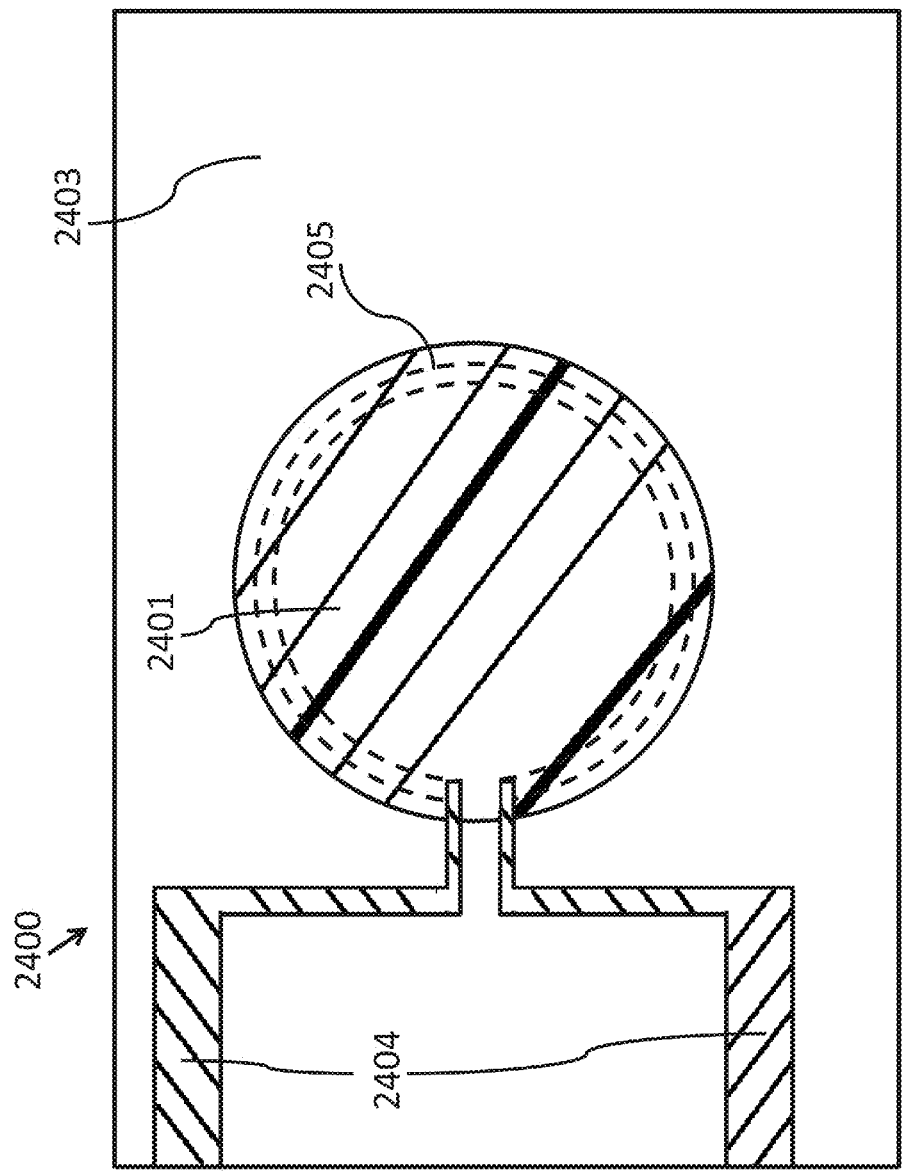

In some embodiments of the current invention, the sensor may be a NanoBridge sensor 2400 wherein the active area may be fabricated such that said active area partially encircles the bead or particle 2401, and is in immediate proximity to said bead or particle 2401, as shown in FIG. 24A, FIG. 24B, and FIG. 24C. Said sensor may comprise a substrate 2402, on which a layer of dielectric and or semiconducting material 2403 may be applied. The active area of the NanoBridge 2405 may be fabricated such that it largely encircles said bead or particle 2401. Metalization lines 2404 may connect to more highly doped regions of semiconducting material 2404A which then interface with the active area 2405 of said NanoBridge. FIG. 24A is a side view of a "ring" NanoBridge, where the inner portion of the active area 2405 is in within the Debye length of the bead or particle and the DNA which may be bound thereto. The active area may be partly or entirely within the Debye length of said bead or particle, resulting in impedance of the entire active area changing in response to changes in the charge which is bound or associated with the bead or particle and or the incorporation event of a nucleotide or nucleotide analog. The diameter of the ring and the associated supporting structure 2403 may be sized such that a bead fits closely within said ring.

Alternatively, as shown in FIG. 24B, the ring and support structure 2400 may be sized to be smaller than the diameter of the bead or particle 2401, such that a bead may rest upon the ring of the active area of the NanoBridge 2405, particularly when held by a magnetic field, insuring that the ring is within the Debye length of the bead or particle 2401 and the DNA bound thereto. FIG. 24C is a top view of a NanoBridge 2400 implemented with a ring structure, showing the overlap of the bead 2401 over the active area of the NanoNeedle 2405, and the electrical conductors 2404 which provide a means to measure the impedance of the active area 2405.

In some embodiments of the current invention, the shape of the Nanobridge sensors may be optimized to provide greater interaction with the magnetic or paramagnetic particle. Said Nanobridge sensors may be shaped in a spiral, serpentine or other non linear shape, or a shape that has a variable cross section so as to provide more surface area while retaining a narrow channel for current to flow through in the channel of the Nanobridge.

NanoBridge Reduction of Streaming Potential Effect

Streaming potential was originally observed by Quinke in 1859, and is a well known phenomenon in capillaries; it is a function of the flow rate, the zeta potential, and the conductivity of the fluid, amongst other factors. Thus a voltage may be impressed on a Nanobridge ISFET, or other chemFET sensors, and variations in the flow rate or distances between electrodes may result in variations either spatially or temporally in the bias impressed on a NanoBridge.

In some embodiments it may be desirable to utilize reference electrodes which may be fabricated between different NanoBridge or ISFET sensors in an array in order to reduce the variation in the bias voltage impressed on the sensitive area of the sensor. In some embodiments, reference electrodes may be fabricated in between each NanoBridge or ISFET in an array NanoBridges or ISFETs on the substrate of the array of said NanoBridges or ISFETs. Said electrodes may be interconnected by metalization as part of the fabrication of said Nanobridge or ISFET array. In other embodiments, sets of said electrodes may be interconnected utilizing metalization as part of the fabrication of said NanoBridge or ISFET array. In other embodiments, said reference electrodes may be fabricated such that a fixed or variable number of NanoBridge or ISFET sensors may be between each NanoBridge or ISFET in the NanoBridge or ISFET array. In further embodiments, the bias voltage difference may be compensated for by software or firmware, wherein the effect of the voltage bias may be measured, mapped and said ma may be used to compensate for variations in the signal level from said array of NanoBridges or ISFETs.

Multiple Reference Electrodes

In some embodiments of the current invention, a reference electrode may be utilized to bias the reagent fluid relative to the sensor electrodes or active area of the sensor device, which may be an array of NanoBridges and/or NanoNeedles, or ChemFETs. In some embodiments, said reference electrode may be configured to be a part of sensor device. In further embodiments, there may be multiple reference electrodes, wherein one or more of said reference electrodes may be part of or associated with a flow cell associated with said sensor device. In other embodiments said two or more reference electrodes may be associated with said sensor device. In some embodiments, multiple reference electrodes may maintain a substantially similar reagent voltage at all of the members of the array in said array of sensors, which might be difficult in a flow cell wherein the fluidic thickness of the flow cell is sufficiently thin as to allow significant resistance over the surface of said sensor array.

In some embodiments of the current invention, an additional electrode or electrodes may be provided to bias the bulk reagent solution in the flow cell. This electrode could be the same electrode(s) which is (are) utilized at other times to concentrate sample and/or other reagents. In some embodiments the voltage impressed on the electrode(s) may be utilized to bias the detectors at an optimal point in their response curve, for example, to provide appropriate offset so as to enable optimization of the amount of gain which may provided so as to provide maximal signal within the available dynamic range of an analog to digital converter, so that A/D quantization error may be minimized.

In some embodiments of the current invention, the bias level may be modified as a sequence reaction proceeds, and the amount of charge which is proximate to a sensor changes. In some embodiments a reading may be taken using the sensors, after which the bias level may be changed, followed by reading the sensors again, so that any nonlinearity or unexpected offsets which result from changing the bias voltage may be observed and compensated for by the software. In some embodiments of the current invention, positive charge may be provided on or near the bead or colony, such that the sensor may be biased to an appropriate level.

In some embodiments, multiple reference electrodes may be utilized with NanoNeedle sensors, NanoBridge sensors, ISFET sensors, or ChemFET sensors.

Changing Reference Voltage during Run

Electronic sensors, such as ChemFETs may be designed to have a wide dynamic range, as is the case with some pH sensors. They may alternatively be designed to have a smaller dynamic range, but higher sensitivity. In one embodiment of the current invention, both the dynamic range of the sensor and the sensitivity of the sensor may be optimized, by including an additional element to the system which biases the active region. Said element may be a reference electrode or electrodes, wherein a variable voltage may be impressed between the reference electrode(s) and the active area of the sensor(s) of a sensor(s) such as a ChemFET or NanoBridge. Adjustment of the voltage can permit highly sensitive detection despite a wide change in the amount of charge interacting with the sensor. For example, a sensor may be optimized to work with a sequencing reaction wherein the target DNA is 100 base pairs long. Alternatively, if the target DNA is 1000 base pairs long, the sensor may no longer be working within said sensors dynamic range. The voltage between said reference electrode(s) and the active area may then be adjusted so that the sensor is permitted to work within its dynamic range. If in the course of the sequencing reaction, the extended primer has been extended to 500 base pairs, the sensor may again no longer be within its dynamic range. The reference voltage may again be modified to bring the sensor within its dynamic range. Additionally or alternatively, a back gate (not shown) may be utilized in much the same fashion. In a further improvement, the back gate may be segmented, such that there may be different sections of the back gate for different areas of a sensor array. There may be many sections, so that it is possible to have an individual back gate for each sensor, permitting compensation for different sequence dependent rates at which the primer is extended.

In some embodiments, changing of the reference voltage(s) may be utilized with NanoNeedle sensors, NanoBridge sensors, ISFET sensors, or ChemFET sensors.

Different Incorporation and Detection Reagents

In some embodiments of the current invention, measurements of polymerase incorporation may be performed during said incorporation in order to determine the sequence of a DNA target. Multiple measurements may typically be needed in order to insure that the profile of incorporation is properly captured and measured, for example to determine the number of bases which have been incorporated in a homopolymer run. Such a measurement may measure byproducts of the incorporation reaction, such as PPi or hydronium ions. For a large array of sensors, such a measurement may require very high data collection rates, which may challenge the sensitivity of the sensor, preventing insufficient signal to noise to provide desired error rates associated with the sequencing data.

There may be difficulties associated with trading off the errors associated with phase error, and thus length of read, and the errors associated with accurately measuring which base, and how many bases have been incorporated. This may be true as a result of needing a low ionic concentration for sensor accuracy, and much higher concentrations in order for the polymerase to function accurately without phase errors.

Alternatively, in some embodiments, two or more different reagent conditions may be utilized wherein at least one set of reagent conditions may be utilized for incorporation wherein the reagent conditions may be optimized for polymerase accuracy and minimization of dephasing, and a second reagent may be utilized wherein the accuracy of the sensor is optimized, for example by the utilization of a very low ionic strength. Reading the sensor separately from the incorporation event may improve the sequencing data accuracy and read length. In some embodiments said sensor may be able to be utilized in a manner whereby less data is required as said sensor may no longer be forced to be read at a high data rate to capture the polymerase incorporation event, but may instead be read a small number of times, potentially as few as a single time, wherein the electronics may have time constants which may be sufficiently long to permit sensor noise to be significantly reduced. Furthermore, in some embodiments, the reduced data requirements may simplify the data processing hardware, data transfer requirements, and data storage requirements.

In some embodiments, said read buffer may be of lower ionic concentration than would be optimal for use for polymerase enzymes; in some embodiments, the ionic concentration of the read buffer may be one third the ionic concentration of the incorporation buffer; in other embodiments, the ionic concentration of the read buffer may be one third to one tenth the ionic concentration of the incorporation buffer, one tenth to one thirtieth the concentration of the incorporation buffer, one thirtieth to one hundredth the ionic concentration of the incorporation buffer, or one hundredth to one thousandth the ionic concentration of the ionic concentration of the incorporation buffer.

In some embodiments, the pH of the incorporation buffer and the read buffer may be substantially the same pH. In other embodiments, the pH of the incorporation buffer and the read buffer may be noticeably different, for example, wherein the pH of the incorporation buffer may be optimized for optimal activity and or accuracy of the polymerase enzyme, such as pH 8.5, while the read buffer may be a pH wherein the pH minimizes the conductivity of said read buffer, such as pH 7.0, wherein the concentration of OH— and H+ are the same at $10^{-7}$ molar. In some embodiments, the optimal pH for minimal read buffer conductivity may be slightly higher than pH 7.0, as the mobility of OH= is lower than that of H+. Thus in some embodiments, the pH of said read buffer may be between pH 6.5 and pH 8.0, between pH 6.8 and pH 7.5, or between pH 7.0 and pH 7.2, while the pH of said incorporation buffer may be between pH 7.5 and pH 9.0, between pH 8.0 and pH 8.8, or between pH 8.3 and pH 8.5.

In some embodiments, different reagent buffers may be utilized with NanoNeedle sensors, NanoBridge sensors, ISFET sensors, or ChemFET sensors.

Integrator as Part of Sensor

In some embodiments of the current invention, an integrator may be incorporated with the sensor in order to maximize the amount of time given to each sensor in order to reduce the read noise of each sensor. The integrator may include a capacitor associated with each sensor in the array. In other embodiments, the sensor may be configured as a capacitive sensor, where there is no current flow, but rather an accumulation of charge during a chemistry cycle. In some embodiments, either an integrating device or a capacitive device, the sensor may have local amplification electronics for each pixel. In other embodiments, the charge may be moved, in a manner similar to a CCD to a readout port.

In some embodiments, integrators may be utilized as a part of the sensor wherein the sensor may comprise NanoNeedle sensors, NanoBridge sensors, ISFET sensors, or ChemFET sensors.

Multiple Read Out Ports

There may be one or more readout ports associated with each device. In some embodiments, each corner of the device may have a readout port; in other embodiments, there may be many ports along opposite sides of the device, allowing a reduced readout rate, and associated improved signal to noise. In other embodiments the readout circuitry can divide the array into columns or rows. In other embodiments the readout circuitry can be placed under channel support or channel separation features. In further embodiments, there may be multiple sets of readout circuitry, wherein the array of sensors may be divided into multiple subarrays, and the multiple sets of readout circuitry may be positioned such that said readout circuitry may be coincident with said channel support or channel separation features. In some embodiments, it may be desirable to utilize flow cells with minimal reagent volume; as such it is desirable to have the height of said flow cell be as short as possible, wherein it may be desirable for said flow cell to be 300 microns tall or less, 100 microns tall or less, or 50 microns tall or less. In some embodiments it may be desirable to utilize a semiconductor device which may be one centimeter square or larger, potentially as large as 10 centimeters square. A flow cell which is wide enough to cover a significant percentage of the width of the sensor chip may have significant difficulties with mechanical tolerances due to flatness of one or both major surfaces of said flow cell with respect to the other surface, particularly if one surface is a molded plastic part or a PDMS or similar polymer part. As a result in some embodiments it may be desirable to utilize support posts, channels or other support shapes to prevent flatness tolerances from collapsing or expanding beyond desired tolerances, and thus better control the fluidic height over the sensor.

In some embodiments the flow cell may be loaded such that the support posts or channel separators are forced in contact with the sensor chip reducing bow. In some embodiments the flow cell top may be made intentionally bowed so that when clamped it will be flatter.

Higher Surface Area for Sensor

In some embodiments, the system may utilize a sensor, such as a bridge sensor, which is arranged in a manner similar to a Fin FET, whereby two or three sides of the channel may be accessible to interact with the surroundings, such as, for example, DNA which is bound to the surface of the channel. The sensor channel may have a vertical dimension perpendicular to the substrate which is greater than the horizontal cross section of the channel. Such a device may have greater sensitivity than a device which has but a single surface accessible to the sample.

In other embodiments, it may be desirable to utilize a material which may provide more surface area than may be available with a planar or polished planar electrode. In some embodiments it may be desirable to utilize black platinum, platinum metal sponge, or a platinized metal, which may be platinized platinum, platinized titanium, platinized iridium, platinized Niobium, platinized tantalum, platinized zirconium, or other platinized metals as an electrode material. Said electrode may be a reference electrode or may be an electrode as part of a NanoNeedle. In other embodiments, the electrode surface may be fabricated of other members of the platinum metal group: palladium, rhodium, ruthenium, iridium, or osmium, which may be utilized in the same manner as platinum to form an electrode surface with much higher surface area than a planar or polished electrode would form.

In some embodiments, the process of platinization may include cleaning a support material, potentially utilizing aqua regia, HCl, and $HNO_3$, followed by a plating process which may utilize chloroplatinic acid and lead acetate.

In other embodiments, the electrode surfaces may consist of iridium oxide, titanium nitrate, or polypyrrole/poly(styrenesulphonate) conducting polymer. Fabrication of said iridium oxide may be effected by sputtering using standard photolithographic processes. Malleo et al (Review of Scientific Instruments 81, 016104) describe the increase in the effective interfacial capacitance of different materials relative to a bright platinum electrode as ranging from 240 times higher for Platinum black, 75 times higher for iridium oxide, and 790 times higher for polypyrrole/poly(styrenesulphonate) conducting polymer.

In some embodiments, sensors with larger surface areas may be utilized with NanoNeedle sensors, NanoBridge sensors, ISFET sensors, or ChemFET sensors.

In some embodiments, a NanoNeedle, NanoBridge, ChemFET or ISFET may be fabricated such that the sensor is created on the surface of a substrate such as silicon, fused silica, glass or other similar material. In other embodiments, the sensor may be fabricated such that it projects vertically or horizontally above the substrate, such that the sensor is more accessible to the fluid and reagents. The greater accessibility to fluid and reagents may decrease the time needed for a sequencing reaction to occur, allow lower concentrations of reagents to be utilized, and increase the sensitivity of the sensor by increasing the surface area associated with the active area of the sensor.

In some embodiments, electrode(s) may be fabricated using an angled rotated deposition approach, which may utilize glancing angle deposition as described by Zhao et al (p 59-73 SPIE Vol. 5219 Nanotubes and Nanowires), or may be fabricated using the PVD methodology described by Hsieh et al in U.S. Pat. No. 6,046,097 Deposition method with improved step coverage, which is hereby included by reference in its entirety.

Improved Chemistry for Improved Detection

Sequencing Chemistry dNTPs which are utilized to extend the primer may be native dNTPs, modified dNTPs which are incorporable by a native or modified polymerase, or both native dNTPs and modified dNTPs. If a modified dNTP is utilized, the modification may be a modification which acts as a reversible terminator, a modification which acts as a virtual terminator, or a modification which changes the charge of an incorporated nucleotide for easier detection. Thus in some embodiments of the current invention, a sequencing reaction may proceed which may incorporate all of the bases in a homopolymer run, or may incorporate one base at a time in a homopolymer run, reducing difficulties in determining the number of bases in a homopolymer run when the number of bases in a homopolymer run is large.

Figure 26:
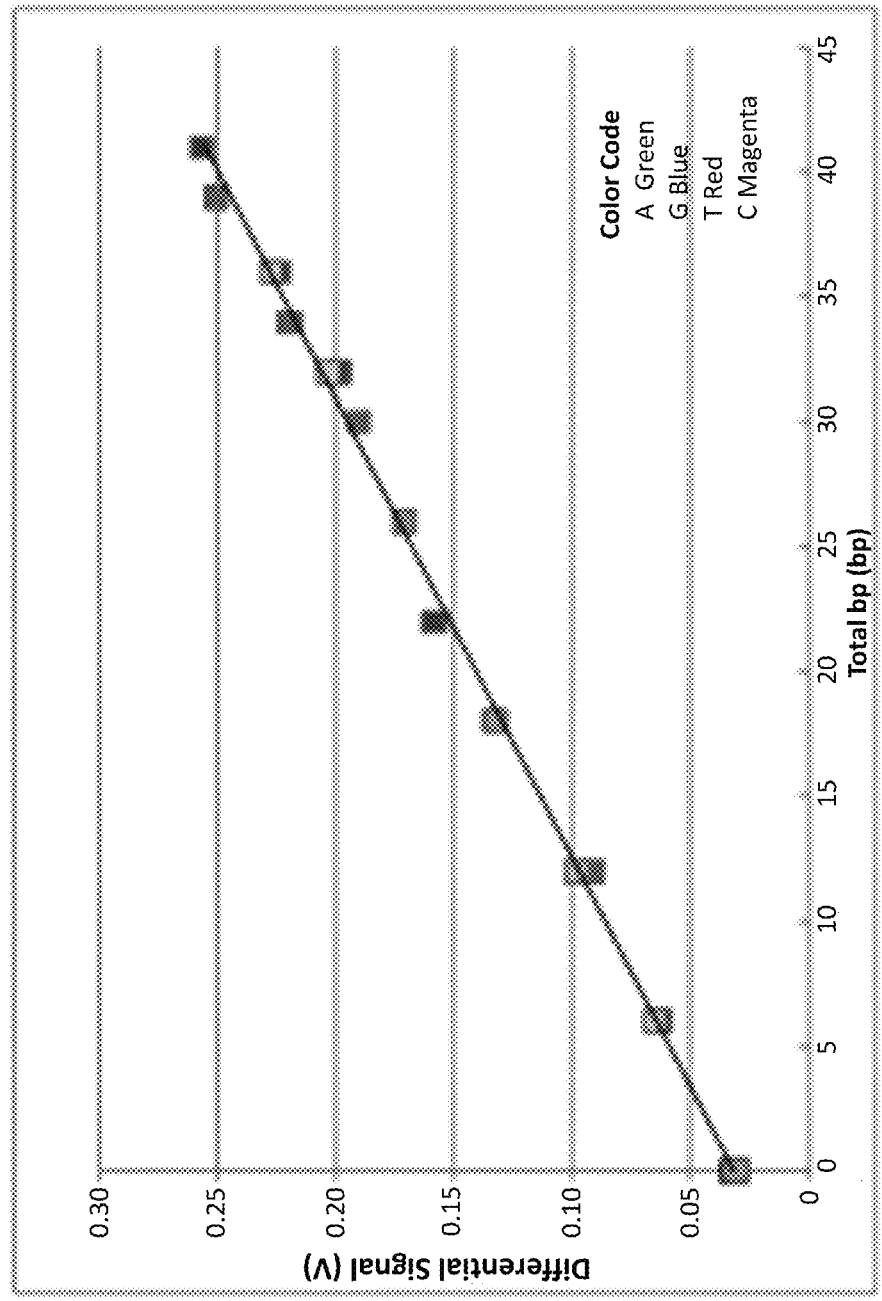
FIG. 26 Illustrates sequencing data and the linearity of same from a NanoNeedle array element.

FIG. 26 shows data from a one run of a NanoNeedle sequencing reaction, wherein run data is scaled and shown relative to a linear plot of base incorporations. dNTPs which should not incorporate are shown as mostly overlapping previous data, and multiple incorporation base data is shown as having quite good linearity (R2=0.9974).

Pre-Binding Polymerase

The kinetics associated with diffusion and binding of the polymerase to the colony DNA may be noticeably longer than the kinetics associated with the diffusion, binding, and incorporation of the dNTPs. As a result, the time period over which polymerization occurs may be longer if the polymerase is brought in the same reagent slug with the dNTPs, as compared with bringing in a reagent slug with polymerase, followed by bringing in a reagent slug with dNTPs. Thus it may be advantageous to the effort of minimizing the amount of data, to bring the polymerase into the flow cell, permitting the polymerase to bind to the colony DNA, prior to bringing in the dNTPs. If the polymerase utilized is a processive polymerase such that said polymerase is well retained between cycles, polymerase may be combined with the dNTPs to eliminate the need for separate deliveries. In another embodiment, the delivery of a wash which includes phosphatase and polymerase may allow effective elimination of residual nucleotides and replenishment of the polymerase in a single fluidic delivery. In other embodiments a reagent may be utilized which includes phosphatase without polymerase to effective elimination of dNTPs by removal of the phosphate group via hydrolysis. The phosphatase may be shrimp alkaline phosphatase, calf intestinal phosphatase, or another phosphatase.

Bead Binding and Spacing

In general, for most clonal DNA sequencing systems, it is desirable to have as much DNA as possible on a surface, in order to maximize the amount of signal which may be obtained. However, as the DNA is randomly placed on the surface, the spacing of the DNA may cause steric hindrance in a subsequent polymerization reaction.

In many different sequencing applications, target DNA or primers may be bound to the surface of the substrate. As a result of the attachment methods, the target DNA and primers may be randomly placed on the surface, and may be in sufficiently close proximity that steric hindrance occurs during a polymerase extension. In some embodiments, primers may be attached, bound or associated to the substrate whilst hybridized to DNA which overlaps the primer, which may provide a priming site for a polymerase. Said primer and overlapping DNA may further comprise a polymerase, which may serve as a spacer to prevent binding of said primers such that steric hindrance would occur, as for example when there is insufficient room for polymerase on each strand of DNA. Said polymerase and overlapping DNA may subsequently be removed so that a target DNA may hybridize to said substrate attached, bound or associated primer for primer extension, which may be for amplification purposes or for sequencing purposes. Alternately the primer could be in the form of a hairpin with an extended end wherein the polymerase could bind eliminating the need for the longer DNA. Even if a Biotin Streptavidin binding of the template is utilized, the size of the streptavidin (3 nm) may be insufficient to properly space the DNA molecules such that there is room for the polymerase (7 to 10 nm). In one embodiment of the current invention, the target DNA may be appropriately spaced such that steric hindrance cannot occur. This may be achieved by for example, using a complex with double stranded DNA and a polymerase which is smaller, similar to or larger in size than the polymerase which will be utilized for the sequencing reaction. Alternatively, other proteins which bind to double stranded or single stranded DNA and may be of appropriate size may be utilized, including the use of a polymerase which is intended for a subsequent sequencing reaction. The polymerase may be processive, so that it remains bound during the attachment process, and may further have additional binding moieties associated therewith, to further enhance the ability of the polymerase to remain in place during the DNA binding process. Alternatively moieties other than proteins can used to space out the DNA and then removed resulting in DNA spaced to avoid steric hindrance. In some embodiments it may be desired that the surface of a substrate may not be saturated with DNA. A dsDNA strand is 20 Angstroms in diameter (2 nm), as opposed to a diameter of potentially greater than 100 Angstroms for the polymerase. For example $E.\ coli$ 22S RNA polymerase is 135 Angstroms in diameter (Kitano et al J. Biochemistry 1969 65 1-16); thus DNA spaced utilizing said polymerase may be spaced at a 2 percent ($2^2/13.5^2*100$) saturation level relative to dsDNA bound to said substrate in a saturated configuration. Polymerases do vary noticeably in size, for example $b.\ strearothermophilus$ DNA polymerase I diameter was reported to be 9 nm (Kiefer et al Nature Vol. 391 15 304) in contrast with previously cited 13.5 nm for $E.\ coli$ 22S RNAP. In some embodiments, it may be desirable to match the number of template copies to the size of the sensor; thus in some embodiments it may be desirable to utilize a relatively small number of template copies. In other embodiments, it may be desirable to use large numbers of template copies. Thus in some embodiments, it may be desirable to utilize 1,000 to 1,000,000 template copies, or it may be desirable to utilize 10,000 to 100,000 template copies, or 100,000 to 1,000,000 template copies. In other embodiments, it may be desirable to utilize 1,000,000 to 100,000,000 template copies, such as between 1,000,000 to 5,000,000 t4emplate copies, 5,000,000 to 20,000,000 template copies, or 20,000,000 to 100,000,000 template copies.

Steric hindrance may still occur when the spacing is equal to the size of the polymerase when the desired length of the DNA template is long, such that much if not most of said DNA is not perpendicular to said substrate. In some embodiments, said DNA template is sufficiently long to "ball up", potentially taking up more space on the substrate than the polymerase. In some cases a ssDNA and/or dsDNA binding moiety may be utilized to space DNA, wherein said DNA may be a DNA primer, and wherein said ssDNA and/or dsDNA binding moiety may be bound to other spacing moieties whereby steric hindrance is minimized by the spacing and subsequent removal of said ssDNA and/or dsDNA binding moiety and associated additional spacing moieties. Said spacing moieties may be other proteins, or may be DNA of similar length to that desired for said DNA template. In some embodiments, which may depend on the size of the desired polymerase and the desired length of template, the level of saturation of attached DNA relative to saturated attached DNA may be 0.001 to 40%, or may be 0.01 to 15%, or may be 0.1 to 5%, or may be 0.5 to 2%.

In some embodiments, by utilizing a polymerase or other spacer while attaching, binding or associating DNA to a substrate, particularly by utilizing a polymerase which is larger than the polymerase which is intended to extend said substrate attached primer, steric hindrance will significantly mitigated. In further embodiments, the polymerase may also be provided with any other helper proteins or other moieties which may serve to increase the effective size of the complex.

Optimized Buffers

In some embodiments the Debye length of the read reagent solution may be similar to that of deionized water, which by definition has $H^+$ and $OH^-$ concentrations of $10^{\char`\^}-7$ molar, and a resultant Debye length of 680 nm. In other embodiments, the ionic concentration of the read solution may be about one micro molar, which results in a Debye length of about 300 nm. This may enable reading during a reaction. In other embodiments, the read solution may comprise ionic solvents which may be not wholly aqueous solvents, permitting lower charge levels in solution, thus enabling a longer Debye length, and thus permitting the nanobridge to sense more of a bead, permitting sensing of a bead which has a diameter greater than one micron, such as two, three, five or more microns. A read solution which comprises nonaqueous solvents may have a conductivity lower than that of distilled water, permitting a higher proportion of current to pass through the counter ions associated with DNA as opposed to current which passes through the bulk solution. The solvents may be miscible with water, and may have solubility of desired moieties; some representative solvents include DMSO, alcohols, and ethers. Said miscible solvents may have lower inherent ionic concentration, having a lower concentration of $H^+$ and $OH^-$ than water. Said solvent may be used in conjunction with water, in part to provide a low concentration of hydrogen ions. In some embodiments, the ionic concentrations may be less than or equal to one micro molar, such as one micro molar to 0.5 micromolar, 0.1 micromolar to 0.5 micromolar, 0.01 micromolar to 0.1 micromolar, 0.001 micromolar to 0.01 micromolar, or less than 0.001 micromolar. In other embodiments, the ionic concentration of the read reagents may be higher than one micro molar, such as for example, 1 milimolar, 2 milimolar, 5 milimolar, or a higher concentration of ions. In some embodiments, the sensor may be able to detect changes in local charge, local conductivity, or local hydrogen ion concentration.

Many commercial buffers utilized for polymerization contain large amounts of Sodium or Potassium Chloride, which is not required for polymerization, and may further be heavily buffered. For example, the NEB Isothermal Amplification Buffer (1×), which is generally described as being applicable for Bst polymerase, contains 20 mM Tris-HCl, 10 mM $(NH_4)_2SO_4$, 50 mM KCl, 2 mM $MgSO_4$ and 0.1% Tween-20; NEB Phi29 DNA Polymerase Reaction Buffer (1×) contains 50 mM Tris-HCl, 10 mM $(NH_4)_2SO_4$, 10 mM $MgCl_2$, and 4 mM Dithiotheitrol. Buffering reagents interfere with pH measurement when utilizing NanoBridges or ISFETs as sensors, and the high ion concentrations create a high background level that may interfere with measurements when utilizing the NanoNeedle sensor.

Thus in some embodiments it may be desirable to utilize buffer reagents with lower concentrations of pH buffers and or lower total ion concentrations.

Buffers and $CO_2$ Exclusion

In some embodiments, it may be desirable to use very low ionic strength reagents, in order to maximize the Debye length. For such embodiments, it may be desirable to utilize reagents which have no more salt than is needed for the enzymatic reaction. For such reagents, it may be desirable to minimize the amount of salt which is utilized, for example reducing or minimizing the amount of NaCl or KCl which may be used, and using sufficient Mg. Sufficient Mg may include a concentration equal to the concentration of nucleotides used in the reagent, with additional Mg to act as counter ions for the DNA, and additional Mg for polymerase in the flow cell associated with the DNA. Thus the concentration needed will be a function of nucleotide concentration, the amount and length of DNA in the flow cell, the number of polymerase molecules, and the volume of reagent used.

In some embodiments wherein the ionic concentration is very low, the pH may be influenced by the surrounding air, with any residual $CO_2$ which may remain after any efforts to minimize the presence of said $CO_2$ forming carbonic acid reducing the pH. Buffering reagents contribute to the ionic concentration; so minimizing the amount of buffering is also desired. Mitigating conflicting needs between having sufficient buffering and having sufficiently low ionic strength may be accomplished by several embodiments. In another embodiment, organic reagents which may be miscible with water may be utilized, such as an alcohol such as ethanol.

In some embodiments it may be desirable to eliminate any monovalent cations such as Na+ or K+ from the buffer to avoid competitive reactions relative to divalent Mg++ causing changes to the counterion distribution on the DNA or beads.

Reducing Charge on Beads

In some embodiments, the charge associated with a bead may diminish the range of an electrical charge/conductivity sensor, or degrade the signal to noise of the sensor. As a result, in some embodiments, it may be desired to minimize the amount of charge present on the surface of the bead, by for instance changing the amount of sulfate or other negative charged moieties on the surface. In some embodiments, it may be desired to have a small amount of negative charge, so that DNA or nucleotides do not bind to the surface of the beads, but not sufficient charge so that there is not significant reduction in the dynamic range of the sensor. In other embodiments the beads may have a slight positive charge such that when DNA primers are attached the beads become negatively charged. Solutions containing solvents such as ethanol can be used to solvate the bead to allow attachment of the DNA.

Circularization of Template

In order to permit repeated measurements of the same DNA sample, the DNA sample may be circularized, whilst the polymerase may be a strand displacing polymerase, or may be a polymerase with 5' to 3' exonuclease activity. Thus the DNA sample may be repeatedly sequenced by allowing the primer extension reaction to continue for multiple cycles around the circular DNA sample. In a distinct advantage over a system which utilizes detection of fluorophores, the system of the current invention can utilize the full capability of the read length of the polymerase, unhindered by having the read length reduced by phototoxicity. In some embodiments, a strand displacing enzyme may be utilized, thus generating an increase in charge and associated counter ions. In other embodiments a polymerase with 5' to 3' exonuclease activity may be utilized, allowing net charge to remain the same, while generating protons and or hydroxide ions, which may be measured as an increase in conductivity, or may be measured as a result of the ions interaction with the surface of an ISFET, ChemFET, or NanoBridge sensor.

Polymerases and Charge Modification of Polymerases

The polymerase bound or associated with the sensor may be a highly processive polymerase, permitting more bases to be incorporated then might occur with a less processive polymerase. The polymerase may be phi29, RepliPHI, MagniPhi®, QualiPhi®, T4 (*E. coli* T4), F-530, B104, or other highly processive polymerases. The polymerase may be modified, so that it has reduced or no 3' to 5' exonuclease activity, or the polymerase may have no or little 3' to 5' exonuclease activity in its native form. Similarly, any 5' to 3' exonuclease activity may be modified so that it is reduced or virtually eliminated. Thermostable polymerases or other types of DNA or RNA polymerases may be used such as: Vent (Tli/*Thermoccus Literalis*), Vent exo−, Deep Vent, Deep Vent exo−, Taq (*Thermus aquaticus*), Hot Start Taq, Hot Start Ex Taq, Hot Start LA Taq, DreamTaq™, TopTaq, RedTaq, Taqurate, NovaTaq™, SuperTaq™, Stoffel Fragment, Discoverase™ dHPLC, 9°Nm, Phusion®, LongAmp Taq, LongAmp Hot Start Taq, OneTaq, Phusion® Hot Start Flex, Crimson Taq, Hemo KlenTaq, KlenTaq, Phire Hot Start II, DyNAzyme I, DyNAzyme II, M-MulV Reverse Transcript, PyroPhage®, Tth (*Thermos termophilus* HB-8), Tfl, Amlitherm™, *Bacillus* DNA, DisplaceAce™, Pfu (*Pyrococcus furiosus*), Pfu Turbo®, Pfunds, ReproFast, PyroBest™, VeraSeq, Mako, Manta, Pwo (*pyrococcus, woesei*), ExactRun, KOD (*thermococcus kodakkaraensis*), Pfx, ReproHot, Sac (*Sulfolobus acidocaldarius*), Sso (*Sulfolobus solfataricus*), Tru (*Thermus ruber*, Pfx50™ (*Thermococcus zilligi*), AccuPrime™ GC-Rich (*Pyrolobus fumarius*), Pyrococcus species GB-D, Tfi (*Thermus filiformis*), Tfi exo−, ThermalAce™, Tac (*Thermoplasma acidophilum*), (Mth (*M. thermoautotrophicum*), Pab (*Pyrococcus abyssi*), Pho (*Pyrococcus horikosihi*, B103 (Picovirinae Bacteriophage B103), Bst (*Bacillus stearothermophilus*), Bst Large Fragment, Bst 2.0, Bst 2.0 WarmStart, Bsu, Therminator™, Therminator™ II, Therminator™ III, Therminator™ Ψ, T7 DNA, *E. coli* Polymerase I, Kenow (*E. coli*) Fragment, Klenow fragment exo−, T4 DNA, *Sulfolobus* DNA Polymerase IV, AMV Reverse Transcriptase, human polymerase mu, human polymerase mu-h6, DNA Polymerase I (*E. coli*), T7 RNA (*E. coli* T7), SP6 (*E. coli* SP6) RNA, *E. coli* Poly (A), Poly (U), T3 RNA.

The polymerase and or DNA may be directly bound to or near the sensor, or may be bound through a linker.

Recombinase Polymerase Sequencing

In some embodiments, a variant of recominase polymerase amplification as described in U.S. Pat. No. 7,270,981, which is hereby incorporated by reference, may be utilized to for sequencing. In some embodiments, the amplified DNA template may be double stranded, and the input primers may be complexed with a recombinase such as RecA or RAD51. Said complexed primers may bind to the double stranded DNA, and with the aid of the recombinase, may displace a portion of the two strands of said double stranded DNA. A polymerase may then bind to the appropriate end of the primer such that said polymerase is able to incorporate nucleobases and extend said primer. Single stranded binding proteins may be added, which may bind to the strand of said double stranded DNA which is not hybridized to said primer. As a result, a larger number of counter ions may be present for sensing, whereby, said counter ions may be associated with the newly synthesized strand of DNA, and additional counter ions may be associated with said single stranded binding proteins. An additional advantage is that issues due to secondary structure resulting from the use of single stranded DNA template are reduced.

Hairpin Primer and Nicking to ReRead

In yet another embodiment, the attached DNA molecule may have a hairpin primer, wherein a portion of the hairpin primer has a restriction site. Subsequently, after completion of the primer extension and associated determination of the sample DNA sequence, the restriction site may be cleaved by an appropriate endonuclease enzyme or nicking enzyme, and the extended primer may be melted off by changing one of the temperature or pH of the solution in which the sample DNA is solvated. The sample may then be re-sequenced after restoring the temperature or pH of the solution in which the sample DNA is solvated to the conditions appropriate for primer extension, including appropriate concentrations of nucleotides and cations. In an alternative embodiment, a strand displacing enzyme, or an enzyme with 5' to 3' exonuclease activity may be utilized, obviating the need to remove the second strand.

In a further embodiment, a linkage may be provided which may be chemically cleaved, obviating the need for enzymatic cleavage.

Polymerase and Helper Proteins Charge Modification

In some embodiments, it may be desirable to minimize the number of counter ions associated with the polymerase and or any other helper proteins, thus it may be desirable to substitute charged amino acids such as Glu, Asp, Lys, His, and Arg with very conservative substitution such as respectively Glu to Gln, Glu to His, Asp to Asn, Arg to Gln, His to Tyr, Lys to Arg, Lys to Gln, Lys to Glu, or with a conservative substitution such as Glu to Arg, Glu to Asn, Glu to His, Glu to Ser, Asp to Gln, Asp to Ser, Arg to Asn, Arg to Glu, Arg to His, His to Arg, His to Gln, His to Glu, lys to Asn, Lys to Ser, using the more divergent BLOSUM45 alignment. Said substitutions may be from a charged amino acid to an uncharged amino acid, or may be from an uncharged amino acid to a charged amino acid, wherein the amino acid which is changed from an uncharged amino acid to a charged amino acid may be adjacent to a charged amino acid of the opposite charge, whereby the charge may be shared between said charged amino acids, obviating or reducing the need for a counter ion.

In some embodiments it may be desirable to make said substitutions on portions of the protein which interact directly with the fluidic environment, as opposed to interacting with ssDNA to which said protein may be bound. In some embodiments it may be desirable to add additional positively charged amino acids in locations which interact and bind with said ssDNA in order to provide tighter binding.

Figure 11:
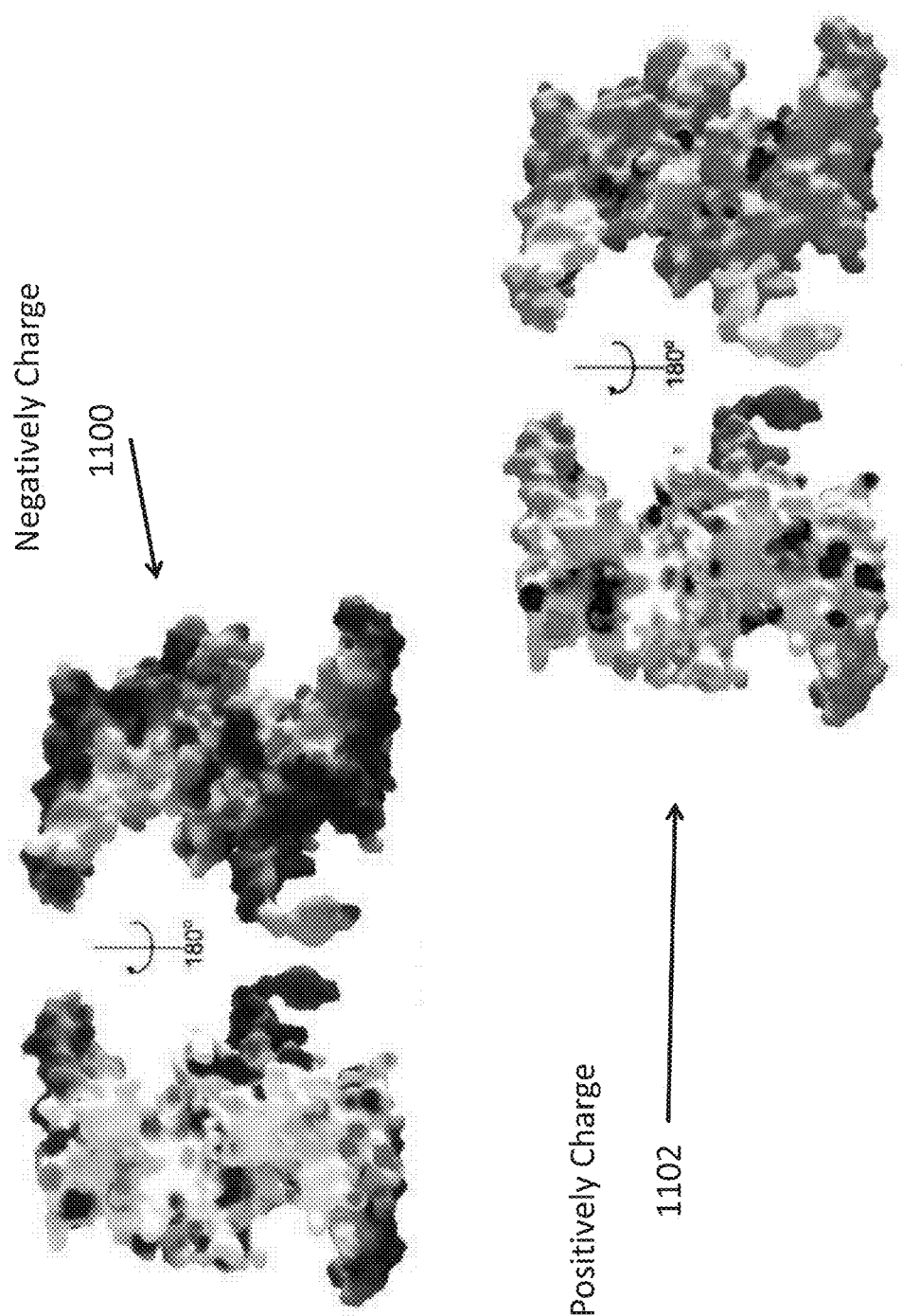
FIG. 11 illustrates the charge distribution of a DNA binding protein.

For example as seen in FIG. 11 (Hollis et al PNAS 98 17 9557), which shows in darker grey as part of 1102 the positively charged portions of a single SSB (normally ternary in vivo), which thereby shows the portions of said SSB which bind ssDNA. FIG. 11 also conversely shows in darker grey as part of 1100 the portions of said SSB which may be positively charged, and which may therefore cause additional counter ions to accumulate as the SSB binds to the ssDNA, causing an increased background current change due to either the influence of charge on the sensitive area of a NanoBridge, or by locally increasing the conductivity of the volume proximate the ssDNA. In some embodiments, a DNA binding protein, which may be a polymerase, or a protein with ssDNA or dsDNA binding affinity, may be mutated such that the binding of said protein(s) to a DNA strand(s) of interest results in a lower background current change than might occur if a native DNA binding protein(s) were to bind to said DNA strand(s) of interest. In some embodiments, the background current change occurs as a result of the binding of a mutated protein(s) to said DNA strand(s) of interest may result in no observable change in the background current relative to the background current without a protein(s) being bound to said DNA strand(s) of interest as a result of the reduced charge of the mutated protein which interacts with the fluid, or as a result of the mutated protein(s) reducing the number of counter ions which may be associated with said DNA strand(s) of interest as a result of increased charge interaction between said mutated protein(s) and said DNA strand(s) of interest. In other embodiments, the background current change occurs as a result of the binding of a mutated protein(s) to said DNA strand(s) of interest may result in a decrease in the background current relative to the background current without a protein(s) being bound to said DNA strand(s) of interest as a result of the reduced charge of the mutated protein which interacts with the fluid, or as a result of the mutated protein(s) reducing the number of counter ions which may be associated with said DNA strand(s) of interest as a result of increased charge interaction between said mutated protein(s) and said DNA strand(s) of interest.

Use of Nick Sites

In other embodiments, a primer may be provided which has a nick site. In still further embodiments, multiple adjacent primers may be provided, obviating the need for a nicking endonuclease. The primers may be complementary to a ligated primer, or may be complementary to a targeted section of DNA. The sequencing primers may comprise all or part of primers used for clonal generation via an amplification reaction, or may comprise regions which may be not used as part of the primers for amplification, or may comprise both regions used for primers in an amplification reaction, and a region which is not used for amplification reaction.

Control of Reagent Delivery to Trigger Reaction

In some embodiments, the quality of measurements the signal may be dependent on the sharpness of the reagent front hitting the sensor, and the collection time window size may be dependent on when the reagent contacts the sensor, particularly for detecting a transient pH change as a result of a base incorporation. The sharpness of the wavefront may be reduced, by for example, diffusion whilst the reagent is moved through fluidic lines, valves and the flow cell itself. To better control the timing and to minimize the diffusion, particularly to minimize the time needed to effectualize a reagent delivery an electric field repulsive charge may be utilized to hold the active reagents, for example the dNTPs may be held away from the sensor in the axis perpendicular to the plane of the sensor array during the initial delivery along the length of the flow cell from the input port to the output port. Later the electric field can be turned off or reversed to draw the reagents to the sensor. In some embodiments the electric field can be activated on different sections of the sensor array at different times to allow better control of the readout time window.

In some embodiments, the flow of reagents through the flow cell may be laminar, and reagent(s) delivered to/on the top of the reaction chamber will stay there with mixing occurring only due to diffusion in the axis perpendicular to the flow of the reagent. This may be used to retard incorporation until desired. In some embodiments both laminar and electric fields could be combined to control the delivery to the sensor.

In other embodiments the temperature can be kept low, such that polymerase activity is minimized while the reagents are delivered and then brought up to allow the reaction to start.

Reaction Triggering

Reactions can thereby be triggered by precise temperature control, thereby overcoming diffusion limitations. For example, in these embodiments the parallel reactions of the array may be almost simultaneous. Activation temperatures are known in the art and/or may be determined experimentally for any particular embodiment. The activation temperature for Klenow polymerase is approximately 4° C., and the activation temperature for Taq is approximately 60° C. In still other embodiments, the reaction may be triggered by introduction of a required reaction co-factor, which may be sequestered in nanoparticles or vesicles prior to the reaction, and released with the appropriate external stimulus (e.g., laser or temperature).

Bar Coding

In some embodiments of the current invention, as a part of the sample preparation process, "barcodes" may be associated with each sample. In this process, short oligos are added to primers, wherein each different sample utilizes a different oligo in addition to primer. The primers and barcodes are ligated to each sample as part of the library generation process. Thus during the amplification process associated with generating each colony, the primer and the short oligo are also amplified. As the association of the barcode is done as part of the library preparation process, it is possible to utilize more than one library, and thus more than one sample, in generating the clonal populations by using synthetic DNA barcodes which may be included as part of the primer, wherein a different synthetic DNA barcode may utilized for each library. In some embodiments, different library may be mixed as they are introduced to a flow cell, and the identity of each sample may be determined as part of the sequencing process.

Sample separation methods can be used in conjunction with sample identifiers. For example a chip could have 4 separate channels and use 4 different barcodes to allow the simultaneous running of 16 different samples. This permits the use of shorter barcodes while still providing unambiguous sample identification.

Reducing Phasing Errors

"Leading sequencing incorporation error" refers to sequences that get ahead of the dominant sequence through incorrect additions of nucleotides. Said incorrect additions may result from polymerase errors, particularly when high concentrations of dNTPs may be utilized in a noncompetitive reaction. Alternatively, said leading sequencing incorporation error may result from inadequate washing or nonspecific binding of dNTPs, which may be subsequently released and incorporated. "Lagging sequencing incorporation errors" refers to sequences that get behind the dominant sequence though missed additions of the correct nucleotide; this may occur due to non-optimal reaction conditions, steric hindrance, secondary structure, or other sources of polymerase inhibition. Longer cycle times can allow more opportunities for the polymerase to incorporate the wrong nucleotide. Similarly less accessible DNA may result in inadequate opportunities to incorporate the correct nucleotide. It is anticipated that temperature, step times, polymerase selection, nucleotide concentration, salt concentration and buffer selection may be optimized to minimize incorporation errors.

For example, a DNA sample may have a sequence of TGTTC in a first region after a region which is complementary to a primer. A fluidic cycle may first introduce dCTP, secondly followed by dTTP, thirdly followed by dATP, and fourthly followed by dGTP, interspersed with wash steps. In the first part of a fluidic cycle, dCTP molecules which flow in as part of said first cycle may not be properly washed out of a well structure. In a second part of a fluidic cycle, dTTP molecules which flow in as part of said second cycle may not be properly washed out a well structure. During the first and second part of the first fluidic cycle, no dNTPs should be incorporated. During a third part of a fluidic cycle, dATPs may be introduced and may be incorporated, as dATP is complementary to T, the first base of the sample. Any non-specifically bound dCTP molecules which cease to be non-specifically bound may also be incorporated during this third portion of a fluidic cycle. These unbound dCTP molecules may be incorporated after a dATP molecule is incorporated. After a dCTP molecule is incorporated, two more dATP molecules may subsequently be incorporated, which may result in some of the molecules of a monoclonal bead having leading sequencing phase errors. Thus some molecules of a monoclonal bead may become "out of phase".

When a polymerase is provided with a single nucleotide or nucleotide analog at a time, the error rate is typically significantly higher than when all four nucleotides or nucleotide analogs are provided. This may occur despite the enormous difference in the catalytic efficiency measured as $k_{pol}/K_{d,app}$, which may be four logs or more lower for a mismatched nucleotide vs. a matched nucleotide. Most of this is due to the difference in $K_{d,app}$. For example, Klenow polymerase has a misincorporation rate of one base in every $10^6$ to $10^8$ bases. In comparison, polymerase extension reactions by current commercial systems utilizing the incorporation of single native dNTPs may be limited to 100 to 1000 bases. The polymerase in these systems spends almost all of its time trying to misincorporate bases, leading to significant "leading" phase errors. Alternatively dephasing may result from a polymerase not incorporating a base in an incorporation fluid flow cycle due to the absence of said polymerase, followed by the presence of a polymerase in a subsequent incorporation fluid flow cycle, or from a sufficiently low combination of dNTP concentration and time for incorporation such that a base is not incorporated, resulting in "lagging" phase error. Even when a nucleotide added to the system is the next nucleotide to be added, the reaction time must be long enough to complete the reaction for a homopolymer, which may be eight or more nucleotides, or for DNA strands that may be less accessible from steric hindrance.

Competitive Reactions Using Non-Incorporable Nucleotides

In some embodiments of the current invention leading phase error can be reduced by making the reaction a competitive reaction, by providing all four nucleotides or nucleotide analogs, wherein three of the four nucleotides or nucleotide analogs may be unincorporable nucleotide analogs. As a result, on a bead or substrate wherein a base addition would not be correct, or after the correct one has been added, the polymerase will spend most of its time futilely trying to correctly incorporate an unincorporable nucleotide. The unincorporable nucleotide may be a PNA nucleotide, a LNA nucleotide, a ribo nucleotide, adenine monophosphate, adenine diphosphate, adenosine, deoxyadenosine, guanine monophosphate, guanine diphosphate guanosine, deoxyguanosine, thymine monophosphate, thymine diphosphate 5-Methluridine, thymidine, cytosine monophosphate, cytosine diphosphate cytodine, deoxycytodine, uracil monophosphate, uracil diphosphate, uridine, deoxyuridin, or other nucleotide analogs which may be bound by a polymerase, but may not be incorporated by a polymerase. Said unincorporable nucleotides or nucleotide analogs may be unlabeled, optically labeled, or charge labeled.

Reducing Both Lagging and Leading Phase Error

In some embodiments, the concentration of the incorporable dNTPs may be increased relative to the concentrations of incorporable dNTPs which would minimize dephasing without the use of unincorporable nucleotides or nucleotide analogs, in addition to adding unincorporable nucleotides or nucleobases, permitting a decrease in both the leading and lagging error rates.

Repeat with Optimal Conditions

In some embodiments it may be desirable to utilize ion concentrations which are lower than might be optimal for synthesis, in order to have an ion concentration sufficiently low for improved operation of the detector. This may result in phasing errors, and a shorter sequence length than desired. It may be desirable to have sequence lengths longer than possible with said low ion concentrations.

In one embodiment, the effective read length may increased by performing a sequencing reaction to the full length possible while utilizing said low ionic concentrations needed for optimal reading of said DNA extension reaction, melting off the extended primer strand, introducing new primers and dNTPs, and proceeding with the synthesis reaction while using optimal ion concentrations for synthesis, which may compromise sensor detection sensitivity, for a number of bases which may be statistically likely to be less than the number of bases which may have been previously sequenced, or for the same number of base addition cycles which were utilized in the previous primer extension, or for a number of base addition cycles which is larger than the number of base addition cycles previously sequenced, followed by changing the conditions to those appropriate for detection. Said process of melting off the extended primer strand, introducing new primers and dNTPs, and proceeding with the synthesis reaction while using optimal ion concentrations for synthesis, for a number of bases which may be statistically likely to be less than the number of bases which may have been previously sequenced, followed by changing the conditions to those appropriate for detection may be repeated multiple times, until the process no longer results in useful data. As the determination of how many synthesis steps to utilize may be statistical, the process may be reversed, performing a synthesis with conditions optimal for synthesis, followed by performing synthesis utilizing conditions appropriate for detection; this may then be followed by melting off the extended primer strands, introducing new primers, and utilizing ionic concentrations appropriate for detection.

Combinations of Concentrations

In order to optimize detection sensitivity, ion and or dNTP concentrations may be desirable which are below the concentrations which may be desirable for proper enzyme kinetics. This may result in longer incorporation times than desired, and/or more lagging phase error.

In some embodiments of the current invention, it may be desirable to utilize more than concentration of dNTPs during a single incorporation cycle. For example, it may be desirable to perform single incorporation cycles with low concentrations of dNTPs and/or ions so as to optimize the sensitivity and signal to noise of the sensors. Thus, a solution with a low concentration of dNTPs and/or ions may be flowed into a flow cell(s) so that measurements may be taken. This may be immediately followed by a solution with a concentration of dNTPs and/or ions which is optimal for incorporation into the extended primer, such that minimal de-phasing may occur. In an alternative embodiment, a high concentration of dNTPs may be flowed into a flow cell(s), so that a quick and optimal incorporation reaction may occur, providing fir minimal de-phasing. This may then be quickly followed by a reagent solution with low or no dNTPs and an appropriately low ion concentration such that an optimal sensor reading(s) may be taken.

In another embodiment of the current invention, a reagent solution with optimal concentrations of dNTPs and/or ions for quick incorporation of nucleotides may be flowed into a flow cell(s) to quickly incorporate a significant portion of the dNTPs into the various colonies as needed, followed very quickly by flowing into a flow cell(s) a reagent solution optimal for optimal sensor reading(s), followed by flowing into a flow cell(s) a reagent solution with concentrations of dNTPs and/or ions at concentrations appropriate for incorporation of nucleotides into the extended primers of the various primers. The first reagent solution may have a concentration of nucleotides which may be sufficiently high that were the reagent solution to be used for an extended time period, polymerase incorporation errors might occur at a noticeable level.

Match Conditions, dNTP Concentration to Incorporation Rate

As polymerase efficiencies may be different for each base, it may be desirable to use different concentrations of different dNTPs, use different buffers, different cation concentrations, different concentrations of polymerase, different types of polymerase, or any combination thereof to optimize the incorporation rate, minimize the amount of phase error, minimize the amount of incorporation error, and maximize the read length.

In one embodiment of the current invention, the concentration levels of the different nucleotides of unincorporable nucleotide analogs may be matched to the relative polymerase activity for each of the nucleotide or nucleotide analogs. For example dTTP binding rate has been measured to be different by a factor of over two with respect to the other nucleotides. The other three nucleotides may be much closer in their polymerase binding rates, but still vary by over 10 percent with respect to each other. It is likely that the difference may be even larger in comparing the polymerase binding rates for different unincorporable nucleotide analogs relative to native nucleotides.

Concentrations of Unincorporable vs. Incorporable dNTPs

In a further embodiment of the current invention, the concentrations of the unincorporable nucleotides needed for equivalent polymerase extension may be higher, equal, or lower than the concentration for optimal primer extension with minimal dephasing for the one or more incorporable nucleotides or nucleotide analogs which may be provided for a sequencing reaction not utilizing unincorporable nucleotides or nucleotide analogs, making the probability of misincorporation of nucleotides or nucleotide analogs lower than if the concentrations of unincorporable nucleotides analogs were provided such that polymerase extension efficiency were matched, or if the unincorporable nucleotide analogs were provided at concentrations with lower polymerase extension efficiency relative to the incorporable nucleotides or nucleotide analogs. Alternatively, the unincorporable nucleotide analogs may be provided at concentrations with lower polymerase binding rates relative to the incorporable nucleotides or nucleotide analogs, such that the reaction may proceed at a higher rate than would occur if the polymerase binding rates of the unincorporable nucleotides were the same or higher than the incorporable nucleotide analog binding rates.

In other embodiments, the concentration of the incorporable nucleotide or nucleotides provided may be varied such that the incorporation rates for the different dNTPs may be more equal. The concentrations may be modified as needed for different buffer conditions, pHs, polymerases, and interactions with any polymerase clamp complexes, or other moieties which may be utilized to stabilize the polymerase.

Use of Unincorporable Nucleotides to Stabilize Polymerase Binding

In some embodiments, unincorporable nucleotides may be used as part of a reagent set which is not intended to cause the incorporation of nucleobases. Such a reagent set may, for example, be intended to wash out a previous set of incorporable nucleobases, prior to introduction of a new set of incorporable nucleobases. Such a wash step may also include phosphatases to degrade triphosphate nucleobases to diphosphates or monophosphates, so that any remaining triphosphates may be degraded and will thus be unincorporable. Said unincorporable nucleobases may occupy a position complementary to the next base in the pocket of the polymerase, and may serve to effectively increase the processivity of the polymerase, as the thumb of the polymerase will remain closed, attempting to incorporate the unincorporable nucleobase, and reducing the disassociation of said polymerase from the DNA.

Unincorporable dNTPs and More Than One Incorporable dNTP

The above approaches may be utilized for reaction conditions wherein there may be three unincorporable nucleotide analogs and one incorporable nucleotide or nucleotide analog, or wherein there may be two unincorporable nucleotide analogs, and two incorporable nucleotides or nucleotide analogs, or wherein there may be one unincorporable nucleotide analog, and three incorporable nucleotide or nucleotide analog.

Stockpiling Polymerase

In other embodiments, lagging dephasing may be reduced by "stockpiling" polymerase enzymes on or near the DNA which is to be extended and sequenced, such that a number of polymerases may be available for each active polymerization site.

Native Binding of Polymerase to DNA

Said stockpiling may result from native binding of the polymerase to the DNA. Such binding may result normally, as for example when a Klenow polymerase is utilized, wherein the Klenow polymerase has intrinsic ssDNA and dsDNA binding.

Use of Non-Extendable Primers for Stockpiling Without Polymerase Exo Activity

Alternatively, in some embodiments, the DNA may be provided with 3' terminated random primers in addition to universal or targeted primers, wherein said universal or targeted primers may be not terminated, and wherein said polymerase may bind at the 3' terminated end of said random primers, as well as to the 3' end of said universal or targeted primers. As said random primers may be terminated, said random primers may not be extended, and thus may not contribute to the signal concomitant to extending the strand from said universal or targeted primers. In this embodiment, the polymerase may be lacking in 3' to 5' exonuclease activity, such that said random primers may be not degraded, resulting in a loss of stockpiling capacity.

In an alternative embodiment, random primers utilizing nucleotide analogs in at least the 3' terminus may be utilized instead of said 3' terminated random primers, wherein said nucleotide analogs may be utilized to generate random primers to which polymerase will bind, but will not extend said random primers comprising nucleotide analogs in the at least 3' terminus position. In this embodiment, the polymerase may potentially have 3' to 5' exonuclease activity if said 3' to 5' exonuclease activity is effectively inactive in removing said nucleotide analogs from said nucleotide analog containing random primers. In some embodiments, it may be desirable for ht $K_d$ to be shorter for a polymerase binding to said 3' terminated random primers, or random primers utilizing nucleotide analogs in the at least 3' terminus position. Said nucleotide analog containing random primers may chimeric, wherein said chimera may comprise native nucleotides and nucleotide analogs, multiple types of nucleotide analogs, or native nucleotides and multiple types of nucleotide analogs.

Use of Thiophosphates to Obviate Need for Exo– Polymerase

In a further embodiment, the random primers may be 3' terminated random primers, wherein the 3' terminus of said random primers may further comprise a thiophosphate nucleotide in the 3' (terminated) position, such that said random primers may be further resistant to 3' to 5' exonuclease activity. Said 3' thiophosphate primers may be commercially available from, for example, IDT (Integrated DNA Technologies). In this embodiment, native polymerases with 3' to 5' exonuclease activity such as phi29 may be utilized, without needing to mutate the polymerase to inactivate the exonuclease activity to prevent degradation of said random primers. Such thiophosphates may be alpha-S or alpha-R stereoisomers. Said random primers may also comprise 5' thiophosphates, such that 5' to 3' exonuclease activity may be inhibited. Alternatively, said random primers may comprise 3' inverted dT, which may act to prevent both polymerization and exonuclease activity with respect to said 3' position of said random primer. Dideoxynucleotides may be utilized as terminators. Said terminators may be reversible terminators, virtual terminators, terminators attached to the base of the nucleotides, or to any position of the sugar the nucleotides. The nucleotides in said random primers may be natural bases, or may be a synthetic base. Said random primers may comprise dNTPs, or may comprise chimeras in combination with PNA, RNA, LNA, 5-Nitroindole, deoxyInosine, or other non-natural dNTPs.

Stockpiling Off Template DNA

Stockpiled polymerases may also be bound to the surface of a bead, to the surface of a sensor, to interstitial regions between sensors, to groups, linkers, or polymers attached to said beads, sensors or interstitial regions. Such binding may be to additional strands of non extendable exonuclease resistant DNA, synthetic DNA or other linear polymers, or may be other binding groups such as antibodies, wherein the binding groups may bind directly to said polymer, or may bind to an intermediate protein which may complex with said polymerase.

$K_{off}$ Relationship to Insure Availability of Polymerase

The relationship in the relative kinetics between the $K_{off}$ of the polymerase from the active incorporation site, and the $K_{off}$ stockpile site(s) and the number of stockpiled polymerases, and the extension period must be appropriate in order to insure that a stockpiled polymerase will be able to replace a polymerase which has disassociated with the active incorporation site of a DNA strand in order to incorporate a base(s) and prevent lagging dephasing within a desired error rate. For example, if the $K_{off}$ is the same for both the active incorporation site, and the stockpile site(s) $K_{off}$ and $K_{on}$, and the $K_{off}$ is equivalent to 20 incorporation fluidic cycles, if one had 20 stockpiled polymerases, the odds that another polymerase will become available to bind to the active incorporation site is less than 50%. This can be improved by reducing the $K_{off}$ of the stockpile sites, and increasing the $K_{on}$ of the Stockpile sites, with the caveat that loss of polymerase to fluid flow may be an issue. The Koff may be reduced as a result of utilizing non natural bases, terminators, or the association of proteins which may normally reduce the processivity of the polymerase to the binding site.

Multiple Types of Polymerases to Insure Availability of Polymerase

The polymerase may be a single type of polymerase, or may be a combination of different types of polymerase. In general, commercialized more processive polymerases have lower incorporation error rates, and as such it may be desirable to mainly utilize highly processive polymerases. It may be desired to have one type of polymerase have a significantly longer $K_{off}$ than another type of polymerase. It may also be appropriate to have polymerase with a shorter Koff available to replace any more highly processive (longer $K_{off}$) polymerase that disassociates, such that a polymerase will be available to incorporate any bases as appropriate. As such, it may be appropriate for the Koff of the less processive polymerase to be less than the time period allocated for an incorporation fluidic cycle, in order to insure that polymerases will available for incorporation should a more processive polymerase become disassociated from the binding site of the extending primer(s).

Bind More Processive Polymerase First

In some embodiments, wherein it may be preferred to utilize two or more types of polymerase, it may be desirable to preferentially bind a more processive polymerase to the primer which is to be extended. It may thus be desirable to allow a more processive polymerase to bind to said primer which is to be extended prior to adding a less process polymerase, which may have ssDNA and or dsDNA binding moieties associated therewith. In other embodiments, it may be desirable to modify or mutate a polymerase such that a binding moiety may be added to said polymerase, such that the polymerase may bind directly to portions of ssDNA or dsDNA.

Replenish Stockpile of Polymerases

Said stockpile of polymerases may be replenished periodically. Said replenishment may occur with every incorporation cycle, or after an appropriate number of incorporation cycles have occurred. The number of cycles between replenishment may vary depending on the stockpiling method. For example, if the stockpiling method is storage on random primers, the number of stockpile locations reduces with the extension of the universal or targeted primer, as said random primers may be displaced by the polymerase, using either strand displacement, or 5' to 3' exonuclease digestion of the random primers. The number of stockpiled polymerases may be maintained, if for example, a second binding mechanism exists for binding to double stranded DNA.

Reduce Secondary Structure

In some embodiments, it may be desired to reduce secondary structure of single stranded DNA which may otherwise interfere with polymerase activity, resulting in lagging phase error. In one embodiment, a protein which binds to single stranded DNA may be utilized. Such proteins may include repair proteins such as bacterial RecA DNA repair proteins, HIV nucleocapsid proteins, T4 bacteriophage gene product 32, calf thymus UP1, Epstein-Barr virus BALF2, or commercialized single stranded binding proteins such as Epicentre *E. coli* single stranded binding protein, as well as many others.

Aid Polymerase Processivity with Helper Proteins

In some embodiments, said single stranded binding proteins may also serve to aid the processivity of the polymerase. In other embodiments other moieties may also aid in the processivity of the polymerase, such as Epstein-Barr virus BMRF1, triplex *S. Cerevisiae* proliferating cell nuclear antigen, T4 bateriophage gene product 45, thieoredoxin, *E. coli*

PolIII holoenzyme, eukaryotic clamp protein PCNA, or other DNA sliding clamp proteins, or other double stranded or single stranded DNA binding moieties.

Mutate Polymerase to Add Helper Proteins

In some embodiments, polymerase processivity may be enhanced by mutations to the polymerase, such as the addition of a helix-hairpin-helix domain to Phi29 polymerase, or the use of a chimerical polymerase as described by Salas et al in PNAS 107 16506, the addition of a thioredoxin binding domain, the addition of an archaeal sliding clamp, DNA binding protein Sso7d, a zinc finger domain, a leucine zipper, amongst other possibilities. In some embodiments, the polymerase may be further modified such that more than one processivity enhancement mutation may be utilized, such as mutations to add both double stranded and single stranded binding moieties at the respective ends of the polymerase. In some embodiments, such binding moieties may also be indirectly bound to the polymerase as for example adding a streptavidin moiety by mutating a polymerase, and adding via mutation a biotin moiety to a single stranded DNA binding moiety and or double stranded DNA binding moiety such as those mentioned above, wherein the polymerase may thence be bound to the single or double stranded DNA binding moiety utilizing streptavidin biotin binding, and further bound to the DNA through said single or double stranded binding moiety. In other embodiments, other binding moieties may be utilized to bind a polymerase to a single stranded or double stranded DNA binding moiety, wherein an additional moiety may be added via mutation to each of the polymerase and the single or double stranded binding moiety, wherein the additional moieties added to the polymerase and the single or double stranded binding moiety have a mutual binding affinity. In further embodiments, a moiety may be added via mutation to one of the polymerase, a single stranded DNA binding moiety and a double stranded DNA binding moiety, wherein the moiety added via mutation may then bind to another of a polymerase, a single stranded DNA binding moiety and a double stranded DNA binding moiety, such that a polymerase may thence be bound to a single or double stranded DNA binding moiety.

Alternative Detection Means

Detection methods which may be utilized for the above reaction conditions utilizing unincorporable nucleotide analogs may include any form of electronic sensing of incorporation or incorporation events, including ISFETs, CHEMFETs, NanoNeedles, NanoBridges, chemilumenescence detection, fluorescence detection, including detection of Qdots or other nonstandard fluorophores, and detection of intercalating fluorophores, detection using fluogenic moieties.

Rephasing

As polymerases may be imperfect, some phase error is inevitable within a colony that has an long extension reaction as a part of a colony based sequencing process; commercial sequencing read lengths have varied from 30 bases for initial systems from 454, Illumina and Applied Biosystems, to reports of as much as 500 bases or more for current 454 systems. But a significant limitation to read length for each of these systems results from de-phasing of the colony. As a result, it is desirable to find a method whereby the colony may be re-phased, so that the sequencing read length may be extended.

In some embodiments, any combination of rephasing techniques described herein may be utilized together in a single sequencing process, or is multiple sequencing processes, and any combination of phase error prevention techniques described herein may be utilized together in a single sequencing process, or is multiple sequencing processes, and any combination of rephasing and phase error prevention techniques described herein may be utilized together in a single sequencing process, or is multiple sequencing processes Better Washing of dNTPs Better washing, as permitted in a chamber-free magnetic retention structure may reduce leading sequencing phase error, by reducing the number of residual nucleotides which may include both unbound and nonspecifically bound nucleotides, which may later be inappropriately incorporated in an incorrect cycle.

Non-Four Base Pattern

In one embodiment of the current invention, the colony may be re-phased by providing sequencing by incorporation nucleotides in different orders than might be otherwise normally done. For example, if a system predominately has lagging phase error (as opposed to leading phase error), with for example a simple 1% lagging error per base (and all four different bases have similar lagging error rate), after 20 bases have been incorporated, just over 75% of the members of the colony may be in phase, while over 20% may be lagging by a single base. By the time 70 bases have been sequenced, less than half of the members of the colony will be in phase, 35% will be lagging by a single base, 13% will be lagging by two bases, and 3% will be lagging by three bases. So, for the following exemplary incorporation sequence example hereinafter referred to as 'SEQ ID 1', (SEQ ID NO:1), where the ideal position is the fourth base of SEQ ID NO:1, 50% of the colony will be in phase at the fourth base (T), 35% will be lagging one base (A), 13% will be lagging two bases (G), and 3% will be lagging three bases (C). If the previous order for incorporation of the bases had been CGAT, and a C is provided, the lagging error will continue, and will be slightly increased. If instead C is excluded the next base provided is G, the leading base will not be extended, while the portion of the colony which is lagging two bases at the first G shown will be extended; if an A is provided next, most of the colony will now be in phase. If a three base combination without C, for example GAT is provided one or more times, any phase error will be concentrated at C bases. Statistically some sequences may become more out of phase as a result, but most sequences may be made to be more in phase. Two base combinations may also be used in much the same manner to re-phase the colonies, and a mixture of two base and three base sets may be utilized. After re-phasing, the system may revert to utilizing four base combinations and rephasing can be repeated as frequently as necessary.

In other embodiments, four base combinations may not be utilized at all, but alternating three and two base sets may be utilized exclusively. In a further embodiment, four base combinations may be utilized in any combination of three and two base sets of nucleotides. In some embodiments, said base sets described may also include the use of unincorporable nucleotides. In other embodiments, the concentrations of the nucleotides and or unincorporable nucleotides utilized in two, three or four base combinations may vary from cycle to cycle, or from set to set.

Use of Terminators to Rephase

In other embodiments, reversible terminator dNTPs may be utilized. This approach may be most advantageous when the sequence being sequenced includes a homopolymer region. For example in the following sequence fragment . . . AGCTCCC, where the in phase portion of the colony has incorporated the T base, with most of the lagging sequence having incorporated the C, G and A bases as the final bases of the members of the colony, if a C' terminating nucleotide is provided, followed by the base combination AGT, AGT, then there may be a predominantly bimodal population, wherein the sequences . . . AGC' and . . . AGCTC' predominate. Said terminator may then be removed from the C' nucleotides, and another C' terminating nucleotide may be provided, resulting in two predominant sequences: . . . AGC and AGCTCC'. The C' terminated nucleotide may then be followed by the base combination AGT, AGT, resulting in the two populations: . . . AGCT and . . . AGCTCC'. The terminator may then be removed, and non-terminated C nucleotides may then be provided, resulting predominantly in a single sequence: . . . AGCTCCC.

This approach may be most effective for those systems which have a predominate source of error, such as, for example, a lagging error. Base combinations which may be used for re-phasing may be added individually, so that the complete sequence of incorporation may be determined, or may be added together, so that re-phasing may be accomplished with a small section of missing data. In some embodiments, reversible terminators may be utilized repeatedly during a sequencing process or method, and may be combined with incorporable or unincorporable nucleotides.

Use of Clamps to Rephase

In other embodiments, a "clamp" may be utilized to largely remove phase error. Such a clamp could be a PNA fragment, a DNA fragment, or other molecule, native or non-native, which binds specifically to a sequence of DNA. In a system which is utilized for targeted resequencing, specific oligos may be used as "clamps". The "clamps" may be provided at the same time that primer sequences may be provided, prior to when primer sequences may be provided, after primer sequences may be provided, before any sequencing reactions have been completed, or after some sequencing reactions have been completed. Multiple different targeted or untargeted clamps may be provided for each template.

Said clamp(s) may be random or targeted to specific regions of a DNA template. A DNA fragment or other clamp may be further stabilized by the use of histones, cationic protamines, recombinase, and other molecules known to stabilize duplex DNA. Sequence reactions may then proceed up to the point of the clamp(s). Additional incorporation reactions may be performed, utilizing single bases, two base combination, three base combinations, or four bases simultaneously. Said clamps may be positioned such that said clamps may be spaced such that a space of from one to 50 bases may exist between the 3' end of the primer and said clamp(s), or may be positioned such that one to 100 bases may exist between the 3' end of the primer and said clamp(s), or may be positioned such that 100 to 500 bases may exist between the 3' end of the primer and said clamp(s), or may be positioned such that one to 500 bases may exist between the 3' end of the primer and said clamp(s), or may be positioned such that one to 5000 bases or more may exist between the 3' end of the primer and said clamp(s), or may be positioned such that 500 to 5000 bases may exist between the 3' end of the primer and said clamp(s).

In some embodiments, the clamp may have a specific number of bases which may specifically hybridize, and may have additional bases which may serve to stabilize said clamp. If the sequence of said clamp is not targeted to a specific region (s), but is instead a non-targeted clamp, the sequence of said clamp may be selected using several criteria, including the stability of the clamp, the frequency of the selected clamp sequence in the genome of interest, or in genomes of a similar nature, or in a chromosome of interest, or in a transcriptome of interest. The hybridization stability of the complete clamp, including any non-specific bases such as deoxyinocine, 5-nitroindole, or abasic nucleotides, or may include any of the universal bases described by Jeon et al in U.S. Pat. No. 7,575, 902, which is hereby included in its entirety by reference, and may include the stability of the bases selected as specific bases for the clamp.

In some embodiments, said clamps may comprise 5, 6, 7, 8, 9, 10 or more specific bases. Said clamps may be utilized for a number of DNA colonies, wherein substantially all of the colonies may have different DNA sequences from other DNA colonies. In some embodiments a single clamp type, comprising a single set of specifically hybridizing dNTPs may be utilized. In other embodiments, multiple clamp types, wherein the number or order or spacing of specifically hybridizing bases may be different. For example, two different hexamer clamps may be utilized to decrease the average spacing, as measured in DNA bases, from the primer to the clamp, or between one clamp and the next clamp, that which would occur if only one of the two hexamer clamps were utilized, but may be larger than that which might occur were a single pentameric clamp to be utilized. In some embodiments, the spacing, as measured in DNA bases from the primer to clamp, or from clamp to clamp may be varied as a result of the choice of the sequence of the clamp, as there is significant variation (more than 20×) in the representation of different hexamers in the transcriptome (Anderson et al RNA V14(5)).

In some embodiments, said clamp(s) may then be removed by raising the temperature, changing the pH or ionic concentration, resulting in the denaturation of said clamp(s), but leaving the longer extended primer(s), which may subsequently be further extended after the removal of said clamp(s). In other embodiments, said clamp(s) may comprise a nick site(s) which may be subsequently nicked by an appropriate nickase or endonuclease, which may destabilize said clamp sufficiently to denature said clamp. In some embodiments, the clamp may comprise cleavable linker sites, wherein said cleavable linker site(s) may be chemically cleavable or photocleavable. In some embodiments, a base terminated at the 3' position may be provided as a part of said clamp(s). Said terminators may be subsequently removed after nucleotides have been added so as to effect rephasing. Said terminator may be removed using chemical or photochemical processes.

In some embodiments, a combination of different types of cleavable linker sites may be utilized for different clamps, so that said clamps with different linker types may be provided prior to beginning any sequencing, or after sequencing has commenced, and different cleavable mechanism may be utilized to denature said clamps in an order which permits multiple rephasing of said template DNA.

In some embodiments, a process including the adding of additional clamps after a sequencing and rephasing process has occurred. In further embodiments, said process of adding of additional clamps may be repeated multiple times, such as 2 to 5 times, 4 to 10 times, or more than 10 times.

In some embodiments, data may be collected as incorporations may be performed for all bases preceding a position adjacent to said clamp; in other embodiments, data may not be performed for all bases preceding a position adjacent to said clamp.

In some embodiments, said clamps may be utilized in combination with non-strand displacing polymerases, such that when said polymerase reaches said clamp through a polymerization process, said polymerase cannot displace said clamp. In further embodiments, the 5' base of said clamp may be linked utilizing a non native linker which cannot be cleaved by a 5' to 3' exonuclease activity which said polymerase may have. In an alternative embodiment, said polymerase may be a non-strand displacing polymerase and may further be lacking 5' to 3' exonuclease activity.

In a further embodiment, a strand displacing polymerase may be used in combination with a clamp which is resistant to strand displacement by said strand displacing polymerase. Said clamp may consist, particularly at the 5' end of said clamp, of non native bases which may be resistant to the strand displacement activity of a strand displacing polymerase. Such a base may comprise an abasic base, such as a base which has been depurinated, or synthetic bases such as PNAs, arabinosyl derivatives of nucleobases, ribonucleotides, 2'-O-alkylribonucleotides, 2'-O-methylribonucleotides, or bases with methylphosphonate linkages.

In some embodiments, the clamp may subsequently be utilized as a primer. Said clamp may include a reversible terminator at its 3' terminus, wherein the primer extension reaction may be continued until a clamp substantially prevents further extension, which may be followed be the removal of the terminator from said 3' terminus of a clamp, permitting a polymerase to initiate a primer extension reaction from said clamp/primer.

In some embodiments, a single clamp/primer may be utilized for a colony or a set of colonies wherein the distance between said primer and said clamp may be significantly more than the average sequencing length before dephasing normally would occur, for example, when it is desirable to utilize said clamp(s) for the purpose of determining the structure of the DNA e.g. creating a scaffold and removing sequence ambiguity due to repetitive sequences. In some embodiments, the distance between the primer and the clamp/primer may be twice as long as the average sequence "read length" before dephasing, or may be from twice as long to five times as long as the average sequence "read length" before dephasing, or may be from five times as long to twenty times as long as the average sequence "read length" before dephasing, or may be from twenty times as long to fifty times as long as the average sequence "read length" before dephasing. Additional clamp/primer(s) may optionally be utilized in this embodiment to extend the read length, and or elaborate further the structure of the DNA colony(s).

In other embodiments, a clamp/primer may be utilized for a colony or a set of colonies wherein the distance between said primer and said clamp/primer or from the clamp/primer to the next clamp/primer may be similar to the average sequencing length before dephasing normally would occur, for example, as would be desirable to extend the length of read of the average sequencing length. The average distance from the primer to the clamp/primer or from the clamp/primer to the next clamp/primer may be from less than half the distance from the primer to the clamp/primer or from the clamp/primer to the next clamp/primer to over twice the distance from the primer to the clamp/primer or from the clamp/primer to the next clamp/primer, or the average distance from the primer to the clamp/primer or from the clamp/primer to the next clamp/primer may be from half the distance from the primer to the clamp/primer or from the clamp/primer to the next clamp/primer to twice the distance from the primer to the clamp/primer or from the clamp/primer to the next clamp/primer.

Combining Clamp and Order

If there is any variation in the stopping point of incorporation as a result of interactions between the clamp, including any stabilizing moiety, and the polymerase (or ligase), a clamp re-phasing method may be combined with one of the methods previously described, which may be advantageously utilized as the sequence of the clamp is already known, permitting addition of bases other than the first base of the clamp sequence, potentially followed by bases other than the second base of the clamp sequence, or any stopping at any other known portion of the clamp sequence.

Types of Clamps

Sin some embodiments, probes may be utilized to prevent further extension of an extended primer. In order to permit short hybridization probes which may be utilized for rephasing, stabilizing compounds such as hydralazine, or antitumor antibiotic cc-1065 may be utilized. Similarly the probe may be a PNA or LNA probe, which may provide the dual function of providing tighter binding, and precluding the need to prevent the probe from being extended by polymerase, by using for example, a terminator at the 5' end of the probe. Additionally the probe may be a single plex, a duplex which may hybridize to the target DNA to create a more stable triplex, or may be a triplex, which may hybridize with the target DNA to form a quadraplex. In some embodiments the probe may be provided in two or more pieces, wherein one portion may be a hybridizing single plex, and a second portion may be hybridize to create a triplex. In some embodiments additional portions to the probe complex may be provided, allowing the formation of a quadraplex, or the formation of a duplex with more than two pieces in addition to the original template.

Driving Phase Error Type

In some embodiments the distribution between leading and lagging phase error may influenced such that one type of phase error may occur at a higher rate than the other type of phase error. In one embodiment the concentration of dNTPS may be limited, so that lagging phase error is more likely that leading phase error. In a further embodiment, rephasing may then be performed to correct for the more probable phases error type. In other embodiments, methods may be utilized which act to correct for both types of phase errors, wherein a method(s) to correction for one phase error type may be performed, and a method(s) for correction the other type of phase error may subsequently be performed. Said method(s) for phase correction may be repeated periodically through the sequence process. In some embodiments, the fluidic pattern for rephasing may be fixed; said fixed pattern may have a fixed number of fluidic sequencing cycles between performing rephasing methods, or the number of fluidic sequencing cycles may change during the sequencing process, for example, by reducing the number of fluidic sequencing cycles between performing rephasing methods.

Monitoring and Then Rephasing as Needed

In some embodiments data from a sequencing reaction may be monitored, and rephasing may be performed when it is observed to be needed, as for example, as seen by signal levels which may be less than expected for a single base, but would be expected if lagging phase error were present, or by the reduction of the signal level observed for single bases. Said observations may consider nominal sequence in determining whether a signal would statistically result from lagging phase error. Said observations may include a histogram of the signal levels for a sequencing fluidic cycle or a set of sequencing fluidic cycles.

Rephasing for Other Systems

In some embodiments rephasing may be performed for any clonal sequencing system, including those which utilize four incorporable nucleotides, as well as all of those described above with respect to minimizing dephasing.

Sequencing

In some embodiments, a device and method may be utilized whereby a single DNA molecule can be sequenced by a NanoNeedle biosensor. A polymerase enzyme may be attached to the sensor. A DNA sample with associated primers may then be caused to enter the volume with said polymerase attached sensors, utilizing for example, pressure induced flow, electro-osmotic induced flow and or migration, or similar means. A single molecule from Single Molecule the DNA sample may then be bound by a polymerase attached to a sensor in a sensor array. Additional single DNA molecules may also be bound by other polymerases bound to other sensors in the sensor array.

In order to permit repeated measurements of the same DNA sample, the DNA sample may be circularized, and the polymerase may be a strand displacing polymerase. Thus the DNA sample may be repeatedly sequenced by allowing the primer extension reaction to continue for many cycles completely around the circular DNA sample. The data for this strand can then be converted into a more accurate consensus sequence with reduced data processing. In a distinct advantage over a system which utilizes detection of fluorophores, the system of the current invention can utilize the full capability of the read length of the polymerase, unhindered by having the read length reduced by phototoxicity.

A single molecule is a case of a monoclonal population in which the population is 1. As such ideas that are relevant to monoclonal DNA typically also apply to the single molecule condition situation.

Figure 25:
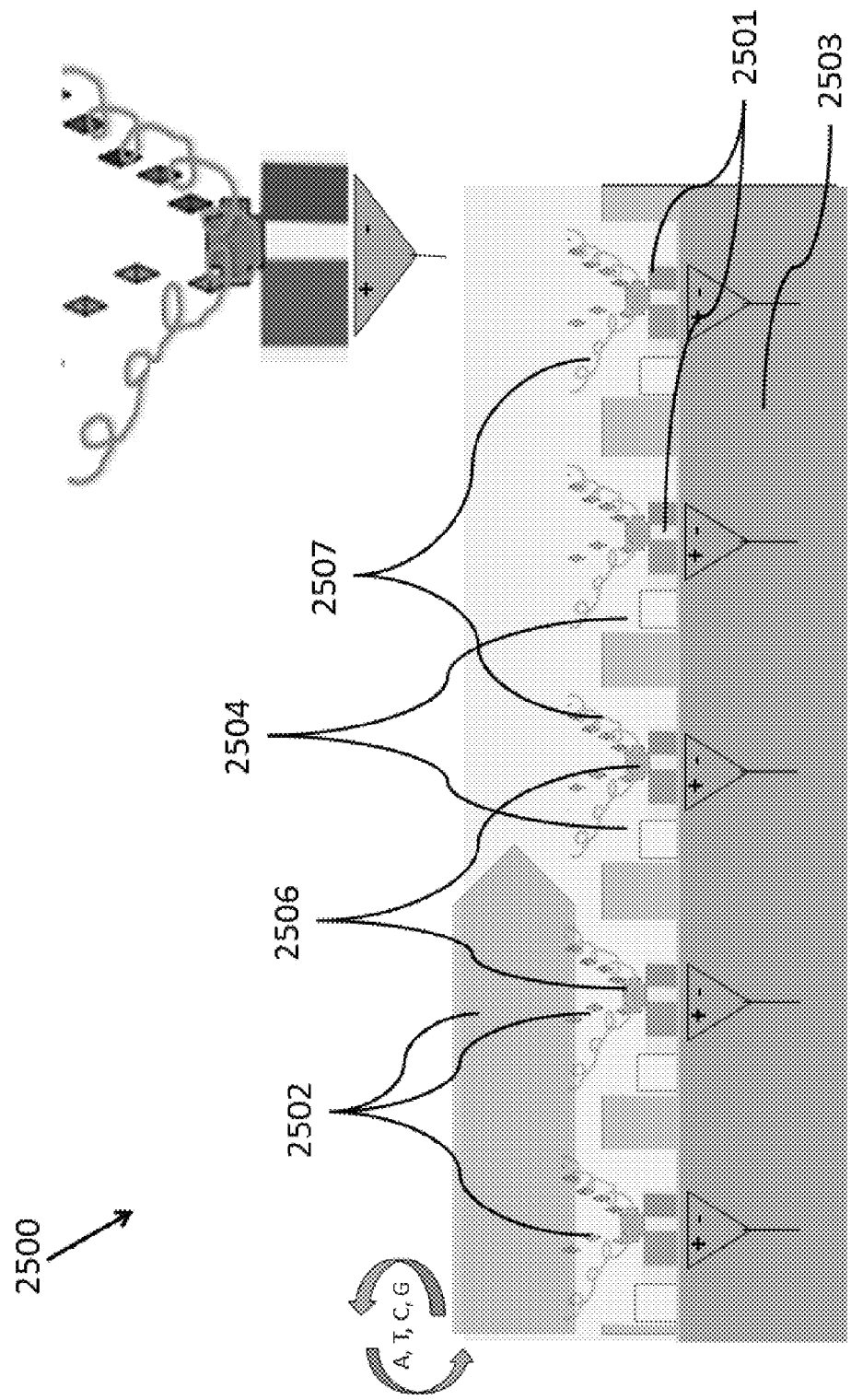
FIG. 25 schematically depicts an array of NanoNeedles utilized for single molecule sequencing.

FIG. 25 describes and illustrates a device and method whereby a single DNA molecule 2507 can be sequenced by a NanoNeedle biosensor array 2500. A polymerase enzyme 2506 may be attached to a sensor 2501. A DNA sample with associated primers may then be caused to enter the volume with said polymerase attached sensors, utilizing for example, pressure induced flow, electrophoretic induced flow and or migration, or similar means. A single molecule from the DNA sample 2507 may then be bound by a polymerase attached to a sensor 2501 in a sensor array 2500. Additional single DNA molecules 2507 may also be bound by other polymerases 2506 bound to sensors 2501 in the sensor array 2500.

In one embodiment, one of the four native dNTPs 2502 is then flowed into the channel volume 2504 with the sensors. If the dNTP is complementary to the next base in the sample DNA 2507, it may be bound and incorporated. The NanoNeedle sensor 2501 may then detect the resulting change in the local charge of the extended primer DNA, permitting detection of the incorporation event, at each appropriate position of the sensor array 2500. If the sample has more than one base in a row which is complementary to the type of dNTP 2502 which has been introduced into the channel volume 2504 with said sensors 2501, a second or subsequent binding and incorporation of a dNTP 2502 may be detected by said NanoNeedle sensors 2501. The dNTPs 2502 may then be washed out of the channel volume 2504 containing the sensors 2501.

In one embodiment, one of the four native dNTPs is then flowed into the volume with the sensors. If the dNTP is complementary to the next base in the sample DNA, it may be bound and incorporated. The NanoNeedle sensor may then detect the resulting change in the local charge, which may be as a result of the change in charge of the extended primer DNA, or may be as a result of other charge changes, permitting detection of the incorporation event, at each appropriate position of the sensor array. If the sample has more than one base in a row which is complementary to the type of dNTP which has been introduced into the volume with said sensors, a second or subsequent binding and incorporation of a dNTP may be detected by said NanoNeedle sensors. The dNTPs may then be washed out of the volume containing the sensors.

A different dNTP may then be flowed into the sensor array volume, permitting detection of incorporation events. Subsequent cycles of washing, introduction of each of the four dNTPs one at a time, and detection of incorporation events permit determination of the different sample DNA sequences.

In an alternative embodiment, non-natural dNTPs may be utilized.

In yet another embodiment, up to four different nucleotides may be delivered simultaneously, and determination as to which nucleotide is incorporated may determined by observation of the kinetics associated with the incorporation reaction.

In an alternative embodiment, the sample DNA may be bound to one of the polymerase, the sensor, or a region between the sensors sufficiently close to the sensor that the bound polymerase may bind the sample DNA after a primer has been introduced into the system and permitted to hybridize with the sample DNA. Subsequently, after completion of the primer extension and associated determination of the sample DNA sequence, the extended primer may be melted off by changing the temperature or pH of the solution, or both the temperature and pH of the solution in which the sample DNA is solvated. The sample may then be re-sequenced by re-introducing the primer and restoring the temperature or pH of the solution in which the sample DNA is solvated to the conditions appropriate for primer extension, including appropriate concentrations of nucleotides and cations.

In some embodiments, the nucleotides may be native dNTPs. In other embodiments, the dNTPs may be modified, with charge modifying structures. The charge modifying structures may be associated, bound or conjugated to the polyphosphate, and subsequently cleaved as part of the incorporation process, obviating the need for a separate process to cleave, separate, or remove the charge modifying structure.

In an alternative embodiment, the charge modifying structure may be utilized as a terminator and thus be associated, bound or conjugated to the 3' position of the sugar of the dNTP, and may thus act as a terminator. Detection may occur as a result of the process of incorporation, or may result from cleavage of the charge modifying structure.

In other embodiments, the charge modifying structure may be associated, bound or conjugated to the 2' or 4' positions of the dNTP sugar. In yet further embodiments, the charge modifying structure may be associated, bound or conjugated to the base of the nucleotide. The charge modifying structures may act as terminators, preventing the incorporation of additional dNTPs.

The linkage, association or conjugation may be broken as a result of a physical process, such as temperature change, or may be broken as a result of a chemical process, or may be as a result of a photochemical reaction.

Said linkage, association or conjugation may be broken after each nucleotide incorporation, or several nucleotides may be incorporated, and the number of nucleotides which were incorporated may be determined as a result of measuring the amount of charge which was added as a result of said incorporation(s).

A different dNTP may then be flowed into the sensor array volume, permitting detection of incorporation events. Subsequent cycles of washing, introduction of each of the four dNTPs one at a time, and detection of incorporation events permit determination of the different sample DNA sequences.

In an alternative embodiment, non-natural dNTPs may be utilized.

In yet another embodiment, all four nucleotides may be present, and determination as to which nucleotide is incorporated may determined by observation of the kinetics associated with the incorporation reaction.

In a further embodiment, two or three nucleotides at a time may be utilized, allowing the addition of multiple bases at a time, and a correspondingly large signal. After completing the extension of the primer, with associated data collection, the extended primer may be melted off, new primer added, and the process of extension may be performed again using a different order of combinations of dNTPs. This process determines which dNTPs do not follow the completion of a previous set of dNTPs, along with information as to the length of the incorporation, wherein said length determination need not be exact.

Reversibly terminated dNTPs may be utilized as part of the dNTP pools. If reversibly terminated dNTPs may be used, all four dNTPs may be provided, wherein one or more of the dNTPs is a reversibly terminated dNTP.

In some embodiments, reverse phase alignment may be performed, wherein a polymerase with 3' to 5' exonuclease activity is utilized with a dNTP pool that is missing at least one dNTP. The polymerase with 3' to 5' exonuclease activity will remove bases back to the next dNTP in the provided dNTP pool, at which point equilibrium will be reached, and no further nucleotides will be removed. This may be performed in order to remove any bases which have been incorporated due to leading phase error. In other embodiments, one or more base type may be incorporated which does not permit exonuclease activity, such as a thiophosphate nucleotide. Exonuclease activity may then be utilized by the removal of unincorporable nucleotides, improving the kinetics for exonuclease activity. In other embodiments, initial incorporations may performed with an exo– polymerase, followed by the use a exo+ polymerase or another nuclease to remove any bases back to a thiophosphate nucleotide or other nucleotide which is resistant to nuclease activity.

The amount of charge present on the DNA, or change in conductivity due to changes in the counter ions, or an increased quantity of hydroxide with concomitant change in pH may be measured during the reaction, or may be measured after the completion of the reaction.

In a further embodiment, blunt end ligation may be performed with ligands that have different binding reagents on the 3' and 5' ends of said ligands. The electrodes of the NanoNeedle may be conjugated with the complementary reagents for binding e.g. the 3' end of the ligands may have a thiol group, and one electrode may be fabricated of gold, while the 5' end of the ligands may have a PNA sequence, and second electrode may have the complement to said PNA sequence. The strand of DNA may then be electrophoretically and or dielectrophoretically concentrated to the area of the NanoNeedle, wherein said DNA strand may then bind with one end associated with one electrode, and the other end associated with the second electrode of the NanoNeedle. Polymerase and primer may be bound to the DNA strand, or may be introduced later. Measurement of incorporation events may then result from direct measurement of the impedance of the DNA combined with the much larger conductivity of the counter ions associated with the DNA.

In an alternative embodiment, other molecules and assays may be utilized, most particularly those which allow detection of kinetics of single molecule reactions, such as other enzymatic reactions.

Software Correction\Standards.

Normalization from Adjacent Empty Sensors

A common practice for FET pH sensors is to utilize a reference electrode; some designs for arrays of FET pH sensors utilize a reference channel for each detection channel; others have reference channels for a set of detection channels. But the local pH of the detector is influenced by the presence of the DNA colony, and changes as the length of the second strand of DNA is extended by the polymerization reaction. In utilizing a chemistry whereby a single type of nucleotide is introduced to the flow sell at a time, many detector channels will not have a reaction taking place at that detector; in fact most detector channels will not have a reaction occurring. Thus in one embodiment of the current invention, neighboring detectors may be utilized as reference channels, providing the data analysis algorithms an opportunity to measure the pH or ion concentration as it changes in detectors which are neighboring detectors to a detector which has a polymerization reaction occurring. This may permit detection of pH or ion concentration levels, or other sources of noise local to the detector of interest, and may also permit detection of crosstalk, allowing monitoring and modification of the crosstalk deconvolution function.

Normalization from Adjacent Beads

In another embodiment of the current invention, adjacent beads or sensor regions which do not have an incorporation reaction in the current fluid cycle may be used as a reference. As on average most beads or sensor regions will not have an incorporation reaction when sequencing large populations of different sequences, these locations without an incorporation reaction may be utilized as additional references. As references, beads or sensor regions without an incorporation reaction may also provide better references relative to empty sensors or null beads, as DNA polymerase, and beads will be present in the volume of interest, and any variation in surface chemistry and resulting background counter ion concentration will likely be better matched. It is likely that different colonies on beads or sensor regions may have colony DNA and/or extended primers of different lengths from the lengths of colony DNA and/or extended primers associated with other beads and or sensor regions, and thus may have different amounts of charge present which may interact with the sensor.

Thus in some embodiments of the current invention, software may need to compensate for the relative length of DNA and/or extended primers associated with sensors and the resultant different charge and signal levels, as well as the location of the beads or colony relative to the sensor, which may influence. The software may keep a record of the signal levels associated with each sensor prior to introduction of a bead to said sensor, signal levels after introduction of a bead but prior to introduction of a primer and or a polymerase(s), signal levels after introduction of a primer and or a polymerase(s) but prior to introduction of a first nucleotide in a sequencing by synthesis reaction, signal levels associated with colonies without primers, signal levels associated with colonies, which may have different lengths of DNA, and the signal levels associated with colonies with hybridized primers, which may have different lengths of DNA. The software may keep track of how many bases have been added to each primer. The signal levels may be an absolute level, or a relative level between different sensors. The software may use a number of other adjacent, or proximate sensors as references to determine the signal level for an individual sensor, compensating for the length of the DNA for each set of colonies, the length of the extended primers, and the signal level which may be generated as a result of positioning of the beads or colonies relative to the sensor. The software may also compensate for the relative position of the sensors relative to the transition between a reagent volume which does not have dNTPs and a reagent volume which does have dNTPs. The software may further compensate for variations in dNTP concentration as a function of diffusion and or dNTP concentration depletion, as a result of incorporation of into extended primers. The amount of diffusion may be characterized from earlier data from the same chip, which may be in the same sequencing run, or from a previous sequencing run, or from sequencing data from a previous chip utilized on the same instrument, or from data from other chips utilized on other instruments. The expected level of depletion may be determined based on data generated as the transition between a reagent volume which does not have dNTPs and a reagent volume which does have dNTPs moves through a flow cell.

Normalization Using Control Beads

In some embodiments of the current invention, control beads may be utilized which have a known sequence, or with different known sequences. The known sequence(s) may have homopolymer runs of different known length, and may be utilized to calibrate the response of the system to better determine the length of homopolymer runs of unknown length. The known sequences may also be useful in determining the level of signal or background signal, as the length of the extended primer and whether an incorporation event has occurred will be known in advance. The control beads may be utilized to differentiate instrument problems from sample prep problems. The control beads with known sequences may be generated outside of the system, and introduced with colonies of DNA attached thereon, or control DNA may be mixed with or introduced prior to or after the sample DNA to generate DNA colonies on beads or otherwise associated with the sensors. In some embodiments, signal levels may be monitored and stored in a manner similar to that described herein for use with normalization from adjacent beads.

Crosstalk Correction

In a manner similar to optical aberration, the diffusion of species being detected by the detectors will cause crosstalk between different detectors. In one embodiment of the current invention, deconvolution of data taken from different sensors on the array may be performed in a manner similar to that used to deconvolve the point spread function from an optical system. The deconvolution function used may depend in part on the temperature of the flow cell at the time of detection, as well as the flow rate through the flow cell, which may tend to cause more crosstalk "downstream" of a particular colony. The deconvolution function which is utilized for said deconvolution may be a fixed deconvolution function, or may be derived as part of a best fit algorithm.

Phase Error Correction

In one embodiment of the current invention, compensation may be performed to reduce for phase error by using earlier and/or later data to determine expected background levels for each cycle for each location. Expected phase error for each base, for each base in the sequence context, and the amount of lagging and leading error previously determined may be utilized to assist in determining the actual base. This error correction may also take into account phase errors from neighbors, as well as the influence of neighbors on the signals received from each sensor.

Signal Level Normalization

In some embodiments, a method may be utilized whereby the sensor array may be made to self calibrating, allowing calibration for such variables as amplification efficiency, bead size and loading, bead placement on the sensor, etcetera. In general, in amplifying a DNA sample to create a monoclonal population of DNA on a bead, a first primer may be ligated to the sample DNA prior to said amplification reaction. In the sequencing process, a second primer is provided which is complementary to said first primer which has been ligated to said DNA sample. Said second primer may be several bases shorter than said first primer. Thus each monoclonal bead has a known initial sequence at a density independent of amplification efficiency, which will be the section of said first primer which is not matched by said complementary second primer. This may permit prior knowledge as to the base sequence, and may include calibration sequences such as known length homopolymer runs.

In an alternative embodiment, such calibration may occur after a sequencing reaction is complete, or alternatively after a number of bases have been sequenced in a sequencing reaction. Statistically, most fluidic cycles in a sequencing reaction will not result in a base incorporation at an individual bead. The next most common result from a fluidic cycle will be the incorporation of a single base. Thus the data set may be analyzed, and appropriate signal levels may be set for each bead.

In a further embodiment, ongoing compensation/calibration may be implemented as the signal level for a base incorporation in a fluidic cycle reduces during a sequencing process, and the background for a not having a base incorporation in a fluidic cycle as a result of factors such as loss of some of the clonal population on the bead, sequencing phase lead, or sequencing phase lag of some of the clonal population on the bead or other factors. Thus a signal level may calculated as to how much signal may be expected for a fluidic cycle which has a single base incorporation, no base incorporation, or multiple bases incorporated due to a homopolymer run, at each point in a sequencing process.

Combined Long and Short Reads

In some embodiments it may be desirable to utilize a system capable of more than one method of sequencing, wherein one method, process or subsystem for sequencing provides information of one type, and a second method, process or subsystem sequencing may provide information of a second type. For example, in some embodiments it may be desirable to provide one method wherein the type of information may elucidate the structure of the DNA sample, enabling sequence reads which may span the length of repeat sequences, such as simple sequence repeats, short tandem repeats, microsatellites, minisatellites, variable number tandem repeats, interspersed repeats such as LINE repeats, SINE repeats such as Alu repeats, direct repeats, or inverted repeats, or other types of repeat sequences which may prevent proper complete assembly of a genome or other desired sequence or sequences of DNA. In some embodiments, it may be desirable to utilize a method, process or subsystem for sequencing which may, for example, elucidate the structure of DNA, wherein it may not be necessary to determine the sequence with high accuracy. In some embodiments it may be desirable to have association of reads which may be separated many bases apart, as is done in some systems, for example by mate pair sequencing or strobe sequencing. In some embodiments it may be desirable to utilize a method, process or subsystem for sequencing which provides sequencing reads which have very high accuracy to detect, for example, single nucleotide polymorphisms, but for which a long sequencing length of read is unneeded. In some embodiments, it may further be desirable to utilize a method, process or subsystem for sequencing provides the ability to provide many short reads with low accuracy, as may be needed, for example, for whole transcriptome analysis.

In some embodiments, it may be desirable to utilize different methods for a single sample, enabling, for example, detection of both single nucleotide polymorphisms and structural rearrangements from a single sample. In some embodiments, it may be desirable within a single system to separate purified nucleic acids into two or more aliquots, which may then have different corresponding library preparation methods, subsystems, or processes which may include amplification, and may utilize different amplification methods, subsystems and processes as appropriate for the different desired sequencing methods, subsystems, or processes. The size, concentration, or volume of the different aliquots may be similar, the same or different, and may be different as appropriate for the different sequencing and/or library preparation method(s), subsystem(s), or process(es) which may be utilized to effect the different desired sequencing results. In some embodiments, said method may be different for different aliquots, but the subsystems utilized may be the same, and or the subsystem utilized for the different methods may be the same subsystem, wherein first one method is utilized, and then a second or more subsequent method(s) may be performed utilizing the same subsystem. For example, it may be desirable to utilize different fragment lengths for different sequencing methods, wherein, for example, long fragments may be desirable for determining sequence structure, whereas short(er) fragments may be desirable for determination of single nucleotide polymorphisms. Thus it may be desirable to fragment different aliquots of the sample to different average fragment lengths, wherein the average fragment length of one aliquot may be longer, potentially significantly longer than another aliquot. In some embodiments, the method of fragmentation may be the same, and may utilize for example, a sonicator, but the time the sonicator applies energy to said aliquots and/or the power level of the sonicator applied to said aliquots may be different, such that the level of fragmentation of the sample in said two or more aliquots may be different, potentially substantially different, and the resultant fragment length may be different, potentially significantly different. In other embodiments, it may be desirable to utilize a single system to generate long fragments and short fragments; in a further embodiment, it may be desirable to fragment DNA to size appropriate for long fragments, remove an aliquot, and further fragment remaining DNA to a size appropriate for said short fragments.

In other embodiments, one aliquot of nucleic sample may be genomic DNA for which single nucleotide polymorphisms may be to be determined, and a second aliquot may be RNA for which a transcriptome may be desired. Amplification methods, subsystems, or processes may be different for the genomic DNA and the RNA, wherein a conversion from RNA to cDNA may be effected, and wherein the amplification protocol may be different for the different aliquots, as the accuracy needed for amplification for single nucleotide polymorphisms may be much higher than the accuracy needed for conversion of RNA to cDNA and subsequent amplification of said cDNA. In some embodiments it may, for example, be desirable to utilize lower concentrations and or less expensive reagents for amplification of cDNA for transcriptome analysis than for amplification of genomic DNA for single nucleotide polymorphism analysis. In further embodiments, it may be desirable, for example, to utilize shorter cycle times for amplification of cDNA for transcriptome analysis than for amplification of genomic DNA for single nucleotide polymorphism analysis, which may speed time to answer allowing for transcriptome analysis to commence utilizing the same sequencing subsystem which may be utilized subsequently by said genomic DNA single nucleotide polymorphism analysis. Any other combinations of separation of nucleic material for subsequent analysis utilizing different sequencing methods, subsystems or processes may be envisioned.

In some embodiments, different types of sequencing detection methods, subsystems or processes may be utilized. For example, one subsystem might utilize single molecule sequencing as described by Church et al in U.S. Pat. No. 5,795,782, Haneck et al in U.S. Pat. No. 8,137,569 Korlach et al in U.S. Pat. No. 7,361,466, and Clark et al in US2011/0177498, which may be hereby incorporated by reference in their entirety, which may have low accuracy and may have very long sequence reads, while another subsystem might utilize optical or electrochemical detection of sequencing by synthesis as described by McKernan et al in US2009/0181385, Balasubramanian in U.S. Pat. No. 6,833,246, Nyren et al in U.S. Pat. No. 6,210,891, Bridgeham et al in U.S. Pat. No. 7,282,370, Williams et al in U.S. Pat. No. 7,645,596, Rothberg et al in U.S. Pat. No. 7,948,015, Toumazou et al in U.S. Pat. No. 8,114,591, and Miyahara et al in U.S. Pat. No. 7,888,013, which may be hereby incorporated by reference in their entirety. Thus in some embodiments, a single system might have at least two different detection subsystems, wherein said two different detection subsystems may utilize different sequencing methods, sequencing detection methods, or sequencing processes, and wherein said different sequencing methods, sequencing detection methods, or sequencing processes may be performed at the same time either for the same sample or for different samples, or may be performed at different times for the same sample or different samples.

Other Uses of Detector

In alternative embodiments, other molecules and assays may be utilized, including those which allow detection of kinetics of single molecule reactions, such as other enzymatic reactions.

Hybridization

In some embodiments of the current invention, other reactions may be utilized and sensed utilizing the sensors. In some embodiments, the reaction may a hybridization reaction, whereby a bead or particle with a hybridization probe attached thereto may be caused to be held in place above a sensor, and the change in charge proximate a sensor or sensors resultant from a hybridization reaction may be measured. In an alternative embodiment, the hybridization probes may be attached on or proximate to the sensors, whereby the change in charge resultant from the progression of a hybridization reaction may be measured. In some embodiments of the current invention, an electric field may be utilized to concentrate DNA from the reagent solution into the volume wherein the hybridization probes may be attached, which may be on a bead or particle, or may be on or proximate to said sensors. Said electric field may be a DC field, an AC field, or a combination thereof.

Real Time PCR

In some embodiments of the current invention, a real time PCR reaction may be monitored by utilizing the sensor or sensors to monitor the change in conductivity or change in charge present, resultant from the incorporation of dNTPs into amplicons, and or the release of pyrophosphate and hydronium ions with higher mobility's. In an alternative embodiment, an isothermal reaction may be utilized to amplify the targeted DNA, wherein the sensors detect the resultant change in conductivity from the incorporation of dNTPs into amplicons. In other embodiments of the current invention, the sensors may be utilized to monitor the progression of an Immuno-PCR reaction, wherein a sandwich assay captures an antigen, and the detector antibody has a probe DNA oligo attached thereto, whereby a realtime PCR assay may then detect and quantitate the presence and quantity of antigen, by the detection of the change in conductivity or charge as previously described. In another embodiment of the current invention, an isothermal reaction may be utilized for the detection and quantitation of the antigen of interest.

Protein Detection with Aptamers

In some embodiments, protein detection may be effectualized by direct measurement of the reaction, by measurement of a sandwich assay, or by measurement utilizing an aptamer, or by other appropriate methods wherein a change in counter ions or a change in charge associated with the target which may be bound, attached or associated with the sensor.

In another embodiment of the current invention, a nucleic acid aptamer which is bound to or proximate to the sensor or sensors may be used to detect the presence and quantity of a target. The aptamer may bind to the target, changing the charge which may be detected by said sensor as previously described. In alternative embodiment, the aptamer may be attached on or proximate to said sensor or sensors, and an increase in the conductivity may be detected as a result of binding of a target thereto.

Electronics

Output Ports

In some embodiments of the current invention, the sensor device, which may be a NanoBridge, or a NanoNeedle, may generate output data which is digital. Said digital output may comprise any of a number of output physical/Data link/protocol formats, including USB2, USB3, Firewire, Gige, single link or dual link DVI, HDMI, S/PIF, ADAT lightpipe, AES3, MADI-X, I$^2$S, AC'97, MC'97, McASP, S-Video, ATM, SONET, SDH, UTP, STP, AUI, HDLC, 802.1, ARP, VLAN, HDLC, ATM, Frame Relay, Q in Q, PPP, BSC, DDCMP, Banyan, CDMA2000, DECnet, CDPD, FUNI, CDMA, X.25, GPRS, GR-303, H.323, NFS, ISDNSS7, TCIP, UMTS, WAP, XNS, MDLP, Infiniband, amongst many others.

Said output may be in compressed format, such as an MPEG 1, MPEG 2, MPEG4, DVA, AVI, MOV, MPG, Video CD, RM, WMA, WMV, WAV, FLC, FLI, BMP, PCX, TGA, TIF, JPG, PCT, GIF, Flash, QuickTime, MP3, or sequences thereof.

Said sensor device may be configured to have more than one digital I/O connection, and may have more than one output format; for example, one digital connection may be used to control the operation of said sensor, whilst one or more digital connection may be utilized to send data from the sensor to additional device which may be part of an instrument of which the sensor is a part. Said additional device may be a data storage, device, or may be a computational device. Said additional device may be a GPU, or a set of GPUs such as a GPU array.

Direct Data Transfer

Said data may be transferred directly from said sensor to a hard disk, directly from said sensor to a solid state drive, or directly from said sensor to a GPU, or directly from said sensor to a GPU cluster, GPU blade, or GPU server, a CPU, or the memory associated with a GPU, or CPU. In some embodiments, an instrument or system may have more than one sensor. In such an instrument or system, data may be accumulated from more than one sensor, and thence sent directly to a hard disk, a solid state drive, a GPU, a GPU blade, a GPU server, a GPU cluster, a CPU or the memory associated with a GPU or CPU.

In some embodiments, a single sensor may have more than one digital output. In other embodiments the digital output may be configured to directly connect to another part of the system, such as a solid state drive or a memory associated with a GPU or CPU, wherein two or more parts of the system may be a part of a MCM (Multi Chip Module), or SIP (System in package). Said MCM may be a laminated MCM, a deposited MCM, a ceramic substrate MCM or a chip stack MCM. The sensor may be a part of the MCM, or may be separate from said MCM. Said sensor may be configured such that said sensor may be removed and a second sensor may be utilized. Said sensor may be interconnected using a socket; said socket may be a zero insertion force socket for a PGA (Pin Grid Array), a LGA (Lan Grid Array) socket, or a slotket.

Said data may be compared with data in a CAM (Content Addressable Memory), or a CAM memory which permits a selectable number of errors in DNA mapping, such as a ternary CAM. Said CAM memory may have multiple levels in a manner similar to that of TLB (Translation Lookaside Buffers), wherein one level of said CAM or TLB may be faster and smaller than another level of said CAM or TLB.

Output Amplifier Structure

To improve the sensitivity of either the NanoNeedle or the Nanobridge, a local amplifier may be provided. The amplifier may be either a BJT or an FET. The sensor can be fabricated as a narrow structure, and can be etched under the structure so that both sides are accessible to changes in pH, conductivity or local charge. The surface of the device may be rough, permitting greater surface area for binding of sample molecules. Electric confinement of ions may be effected as will be described further hereafter.

In some embodiments of the current invention, the image sensor array may utilize amplifier designs similar to those in CMOS active pixel image arrays; these may include three transistor, four transistor, five transistor, or six transistor circuits, depending on the signal to noise needed, and whether a global shutter equivalent is desired if a integrating circuit is utilized. Said amplifier structure may be arranged in a one to one correspondence with said image sensor array, potentially providing significantly better signal to noise than might otherwise be possible utilizing a common amplifier for multiple sensors.

While various embodiments have been described above, it should be understood that they have been presented by way of example only, and not limitation. Where methods and/or schematics described indicate certain events, and/or flow patterns, and/or chemical reactions occur in a certain order, the ordering of certain events and/or flow patterns and/or chemical reactions may be modified. While the embodiments have been particularly shown and described, it will be understood that various changes in form and or detail may be made.

Although various embodiments have been described as having particular features and/or combinations of components, other embodiments may be possible having a combination of any features and/or components as discussed above.

What is claimed is:

1. A system for sensing a biological reaction in a solution, comprising:
    a bead in said solution bound or attached to at least one biological reactant, wherein said biological reactant comprises a nucleic acid template;
    a pair of electrodes in contact with said solution and positioned such that, during sensing by said pair of electrodes, said pair of electrodes are each within the Debye layer of said bead when said bead is immobilized in proximity to said pair of electrodes;
    a bead capture feature that immobilizes said bead in proximity to said pair of electrodes; and
    a device that (i) receives electrical signals from said pair of electrodes when said pair of electrodes is within the Debye layer of said bead, and (ii) using said electrical signals, determines change(s) in impedance resulting from a biological reaction with said nucleic acid template.

2. The system of claim 1, wherein one electrode of said pair of electrodes is on a device substrate, a dielectric layer is on said device electrode, and a second electrode of said pair of electrodes is on said dielectric layer.

3. The system of claim 1, wherein said pair of electrodes is part of an array of electrode pairs.

4. The system of claim 3, wherein said array comprises a 2D array of electrode pairs.

5. The system of claim 1, wherein said solution is an aqueous solution.

6. The system of claim 5, wherein said aqueous solution has an ionic concentration of less than $10^{-8}$ molar.

7. The system of claim 1, wherein said solution is a miscible mixture of an aqueous solution and an organic solution.

8. The system of claim 7, wherein said miscible solution has an ionic concentration less than $10^{-7}$ molar.

9. The system of claim 1, wherein one or more of the electrodes of said pair of electrodes is shaped to conform to the shape of said bead.

10. The system of claim 9, wherein said one or more electrodes of said pair of electrodes are shaped at least in part in an arc with a diameter similar to the diameter of said bead.

11. The system of claim 1, wherein at least one of said pair of electrodes is within at least 0.1 Debye lengths of said bead.

12. The system of claim 1, wherein said pair of electrodes comprises a first electrode and a second electrode separated by a dielectric layer, and wherein said device further comprises a substrate adjacent to said first electrode.

13. The system of claim 12, wherein said first electrode is below a center line of said bead, and said second electrode is above a center line of said bead.

14. The system of claim 1, wherein said electrodes are planar.

15. The system of claim 1, wherein an individual electrode of said pair of electrodes has a Debye layer.

16. The system of claim 1, wherein said device receives electrical signals from said pair of electrodes when said bead is immobilized in proximity to said pair of electrodes.

17. The system of claim 1, wherein said bead capture feature immobilizes said bead in proximity to said pair of electrodes by an immobilizing force.

18. The system of claim 17, wherein said immobilizing force is selected from the group consisting of a magnetic force and an electrical force.

19. The system of claim 17, wherein said bead capture feature comprises a magnet, and wherein said immobilizing force includes a magnetic force.

20. The system of claim 1, wherein said bead capture feature is selected from the group consisting of a magnetic structure and a depression.

21. The system of claim 1, wherein said bead capture feature is part of a magnetic array.

* * * * *

UNITED STATES PATENT AND TRADEMARK OFFICE
CERTIFICATE OF CORRECTION

Page 1 of 1

PATENT NO. : 9,399,217 B2
APPLICATION NO. : 13/481858
DATED : July 26, 2016
INVENTOR(S) : Hesaam Esfandyarpour et al.

It is certified that error appears in the above-identified patent and that said Letters Patent is hereby corrected as shown below:

In the Specification

Column 1, Lines 17-23, please delete:
"STATEMENT REGARDING FEDERALLY SPONSORED RESEARCH AND DEVELOPMENT
This invention was made with government support under grant "Qualifying Therapeutic Discovery" grant awarded by IRS. The U.S. government may have certain rights in the invention."

Signed and Sealed this
Thirteenth Day of April, 2021

Drew Hirshfeld
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 1

<210> SEQ ID NO 1
<211> LENGTH: 14
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
```

```
<222> LOCATION: (1)..(3)
<223> OTHER INFORMATION: n is a, c, g, or t

<400> SEQUENCE: 1
nnncgatcga tcga                                                        14
```